US008772446B2

(12) United States Patent
Adam et al.

(10) Patent No.: US 8,772,446 B2
(45) Date of Patent: Jul. 8, 2014

(54) BIFUNCTIONAL CHELATING AGENTS

(75) Inventors: Mike Adam, Surrey (CA); Eszter Boros, Vancouver (CA); Cara L. Ferreira, Surrey (CA); Chris Orvig, Vancouver (CA); Eric William Price, Vancouver (CA)

(73) Assignee: Nordion (Canada) Inc., Ottawa, Ontario (CA)

( * ) Notice: Subject to any disclaimer, the term of this patent is extended or adjusted under 35 U.S.C. 154(b) by 260 days.

(21) Appl. No.: 13/030,766

(22) Filed: Feb. 18, 2011

(65) Prior Publication Data
US 2011/0313130 A1 Dec. 22, 2011

Related U.S. Application Data

(60) Provisional application No. 61/306,256, filed on Feb. 19, 2010, provisional application No. 61/394,739, filed on Oct. 19, 2010.

(51) Int. Cl.
*A61K 38/12* (2006.01)
*C07K 5/00* (2006.01)

(52) U.S. Cl.
USPC ............ 530/317; 530/399; 530/405; 530/409

(58) Field of Classification Search
USPC .......... 424/1.53, 9.36, 9.364; 530/317, 391.1, 530/391.5, 405, 409
See application file for complete search history.

(56) References Cited

U.S. PATENT DOCUMENTS

| 5,021,567 A | 6/1991 | Johnson et al. |
| 8,309,058 B2 | 11/2012 | Mazzanti |

FOREIGN PATENT DOCUMENTS

| JP | H01-113349 | 5/1989 |
| WO | WO 2007/031640 A1 | 3/2007 |

OTHER PUBLICATIONS

Carlos Platas-Iglesias et al., Lanthanide Chelates Containing Pyridine Units with Potential Application as Contrast Agents in Magnetic Rersonance Imaging, Chem, Eur, J. 2004, 10, 3579-3590.*
Nicholas Chatterton et al., The effect of pyridinecarboxylate chelating groups on the stability and electronic relaxation of gadolinium complexes, Dalton Transcantion, 2005, 1129-1135.*
Marta Mato-Iglesias et al., "Pyridine and Phosphonate Containing Ligands for Stable Lanthanide Complexation. An Experimental and Theoretical Study to Assess the Solution Structure", Dalton Transactions, Oct. 13, 2006, vol. 45, 5404-5415.
Nicholas Chatterton et al., "The Effect of Pyridinecarboxylate Chelating Groups on the Stability and Electronic Relaxation of Gadolinium Complexes", Dalton Transactions, Feb. 10, 2005, vol. 6, 1129-1135.
Carlos Platas-Iglesias et al., "Lanthanide Chelates Containing Pyridine Units with Potential Application as Contrast Agents in Magnetic Resonance Imaging", Chem. Eur. J. 2004, vol. 10, 3579-3590.
Raquel Ferreirós-Martinez et al., "Selective Chelation of Cd(II) and Pb(II) versus Ca(II) and Zn(II) by Using Octadentate Ligands Containing Pyridinecarboxylate and Pyridyl Pendants", Inorganic Chemistry, Oct. 30, 2009, vol. 48, 10976-10987.
Eszter Boros et al., "Acyclic Chelate with Ideal Properties for $^{68}$Ga PET Imaging Agent Elaboration", J.A.C.S. Articles, Oct. 19, 2010, vol. 132, 15726-15733.
Zhaoxia Yang et al., "New Tetraazacrown Ethers Containing Two Pyridine, Quinoline, 8-Hydroxyquinoline, or 8-Aminoquinoline Sidearms", J. Org. Chem., Apr. 13, 1999, vol. 64, 3162-3170.
C. Mouralian et al., "Mobilization of Iron from Cells by Hydroxyquinoline-Based Chelators," vol. 71, 214-222 (2005).
Claire Marchal et al., "Lanthanide-Based Coordination Polymers Assembled by a Flexible Multidentate Linker: Design, Structure, Photophysical Properties, and Dynamic Solid-State Behavior," vol. 15, No. 21, 5273-5288 (2009).
Jul. 17, 2013 Communication from EPO enclosing European Search Report and European Search Opinion.
Japanese Notification of Reasons for Refusal dated May 12, 2014, issued in counterpart Japanese Application No. 2012-553161.

* cited by examiner

*Primary Examiner* — Michael G Hartley
*Assistant Examiner* — Jagadishwar Samala
(74) *Attorney, Agent, or Firm* — Arent Fox LLP

(57) ABSTRACT

A bifunctional chelating agent of the formula (I):

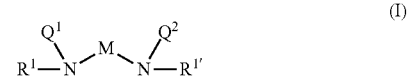

wherein the variables $R^1$, $R^{1'}$, $Q^1$, $Q^2$ and M are as defined in the description of the present application. Also described is a complex of the above chelating agent to an ion of a stable or radioactive metal; a conjugate of the complex covalently attached to a biological carrier; and a pharmaceutical composition containing the conjugate.

17 Claims, 21 Drawing Sheets

BIFUNCTIONAL CHELATING AGENTS

CROSS-REFERENCE TO RELATED APPLICATION

This application claims benefit to U.S. Provisional Application No. 61/306,256, filed Feb. 19, 2010, and U.S. Provisional Application No. 61/394,739, filed Oct. 19, 2010. The disclosure of the prior application is hereby incorporated herein in its entirety by reference.

FIELD OF INVENTION

The present invention relates to bifunctional chelating agents, to complexes of these chelating agents with metal ions, and to conjugates of these complexes with biological carriers. More particularly, the present invention relates to chelates for radiometals useful in molecular imaging and therapy, in particular, to radioisotopes of gallium such as $^{66}$Ga, $^{67}$Ga, and $^{68}$Ga.

BACKGROUND OF THE INVENTION

Diagnostic imaging and therapeutic radiopharmaceuticals play an important role in modern medicine. Many of the important radionuclides used in current applications are metals positioned in the main group or lanthanide series.[1] This family of metals possesses diversity in nuclear and chemical properties that can be harnessed for both diagnostic and therapeutic applications. In nearly all cases, these metal ions are inherently toxic in a simple salt form and must be sequestered into an organic chelating compound (ligand) in order to render them biologically compatible. Furthermore, the ligand architecture is vitally important for creating a linking group for attachment to a biological targeting molecule.

Chelates are widely employed to isolate metal ions from environmental factors that would interfere with the intended use of the metal ions. This is commonly seen in the field of nuclear medicine, where radioactive isotopes of metals, i.e., radiometals, are used for molecular imaging and therapy due to their decay characteristics such as half-life and emission profile and due to their chemical properties such as lipophilicity and coordination behaviour.

Chelating agents for the main group and lanthanide metal ions have been the subject of intense fundamental and applied research for many years driven in part by advancements in medicine.[2] For example, the emergence of magnetic resonance imaging (MRI) as a new diagnostic modality brought with it the need for paramagnetic metal-based contrast agents to enhance image quality, for this application gadolinium from the lanthanide series is preferred.[3] As a result, there has been an exponential acceleration in the design and synthesis of new ligand systems that can hold up to the rigors of in vivo applications for MRI.[4] Equally important is the fact that these same ligand systems are being recruited for other members of the lanthanide series ($^{153}$Sm, $^{177}$Lu, $^{166}$Ho) and $^{90}$Y which possess highly desirable nuclear properties making them useful in radiopharmaceutical agents.[5] The adaptability of similar ligands for all lanthanide ions is due to the very uniform and predictable properties intrinsic to the lanthanide series. The critical prerequisites of chelate complexes for metallic radioisotopes intended for human use is that they remain stable in the body (no dissociation of the metal) and that they can be prepared reasonably fast. This latter point is more applicable to nuclear applications where isotope half-life is a critical consideration in the formulation process. Chelate effectiveness is assessed in terms of thermodynamic stability and kinetic inertness. One often desirable property of chelates for biomedical applications is high thermodynamic stability. However, these ligand systems usually require longer reaction times and additional energy input is needed to form the final complex.

Gallium is a main group metal that comprises three radioactive isotopes useful in nuclear medicine. $^{66}$Ga is a positron-emitter with a half-life of 9.5 h; $^{67}$Ga, a gamma-emitter with a half-life of 3.26 d; $^{68}$Ga, a positron-emitter with a half-life of 68 min. Positron-emitters are useful for positron-emission tomography (PET) imaging; gamma-emitters, for single-photon-emission computed tomography (SPECT) imaging.

The chelates that are currently commonly used to bind gallium radiometals to biological targeting molecules are dominated by 1,4,7,10-tetraazacyclododecane-1,4,7,10-tetraacetic acid (DOTA) and 1,4,7-triazacyclononane-1,4,7-triacetic acid (NOTA) and their derivatives. However, several studies have indicated that the conditions for the reactions of gallium with DOTA and NOTA could be improved by enabling formation of the coordination complexes in shorter times at ambient temperatures. These improvements are particularly critical to the widespread adoption of $^{68}$Ga as a radiometal of choice for nuclear medicine because of its relatively very short half-life of 68 min.

Chelates comprising picolinyl groups attached to a nitrogen atom[6,7], ethylenediamine (en)[8,9,10,11,12,13,14], cyclohexane-1,2-diamine[15,16], and 1,4,7-triazacyclononane[17,18,19,20,21] have been reported in the scientific literature and have been the subject of patent applications.[22,23] These chelates have been designed to coordinate lanthanide ions, which are relatively large metal ions that in some instances possess large magnetic moments and are useful as magnetic-resonance-imaging contrast agents. Thus, the chelate comprising en has four picolinyl groups attached to each of the two en nitrogen atoms to give a decadentate (10-coordinate) chelate whereas the chelate comprising 1,4,7-triazacyclononane has three picolinyl groups attached one each to the three 1,4,7-triazacyclononane nitrogen atoms to give a nonadentate (9-coordinate) chelate. Classes of chelates comprising these particular chelates have been the subject of patent applications.

A chelate comprising two picolinyl groups attached one each to the two nitrogen atoms of en, hereafter called dedpa, and also of cyclohexane-1,2-diamine has been reported in the scientific literature[24]. Complexes of said chelate dedpa with the metal ions $Zn^{2+}$, $Cd^{2+}$, and $Pb^{2+}$ were synthesized and found to comprise a hexadentate chelate bound to the metal ions to form an octahedral coordination environment. The present invention relates to chelates based on dedpa that can form complexes with radiometals useful in molecular imaging and therapy, more specifically for forming complexes with gallium radiometals for molecular imaging, because gallium radiometals prefer an octahedral coordination environment. An added advantage of using chelates based on dedpa for forming complexes with gallium radiometals is that gallium radiometals exist under physiological conditions as tripositive ions ($Ga^{3+}$) that form stronger coordination complexes than $Zn^{2+}$, $Cd^{2+}$, or $Pb^{2+}$ because of the increased charge of the ion.

SUMMARY OF THE INVENTION

The present invention relates to bifunctional chelating agents, to complexes of these chelating agents with metal ions, and to conjugates of these complexes with a biological carrier. More particularly, the present invention relates to chelates for radiometals useful in molecular imaging and therapy, in particular, to radioisotopes of gallium such as $^{66}$Ga, $^{67}$Ga, and $^{68}$Ga.

The present invention provides a bifunctional chelating agent of the formula (I):

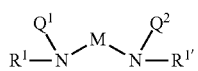
(I)

wherein:
-M- is

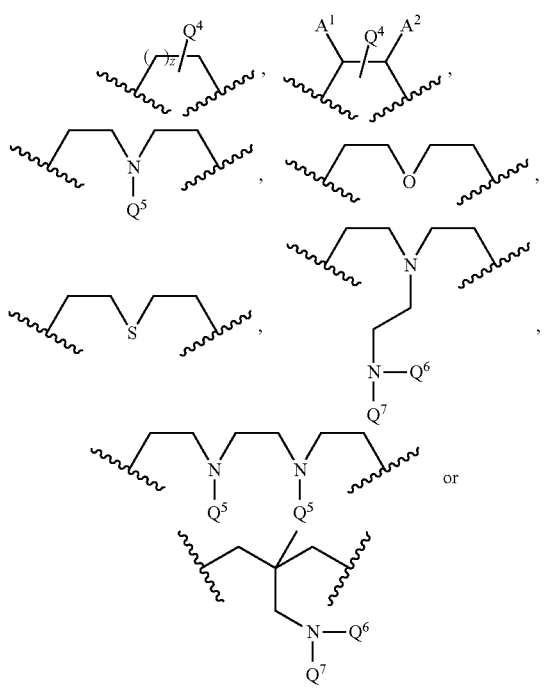
or $Q^1$, $Q^2$ and $Q^4$ are independently H or R;
$Q^3$ is H, —(CHR$^2$)$_w$COR$^3$ or —(CHR$^2$)$_w$PO$_2$R$^4$R$^5$;
$Q^5$ is H, R or R$^{1'''}$;
$Q^6$ is H or R$^{1'''}$;
$Q^7$ is H or R;
A$^1$ and A$^2$ form together with the atoms to which they are attached a C$_6$-C$_{10}$-aryl, C$_6$-C$_{10}$-heteroaryl, C$_3$-C$_{10}$-cycloalkyl or C$_3$-C$_{10}$-heterocyclyl group;
R is —C(O)-L,

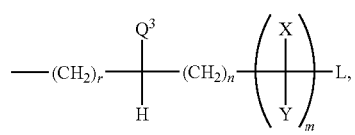

—(CHR$^2$)$_p$COR$^3$ or
—(CHR$^2$)$_p$PO$_2$R$^4$R$^5$, provided that at least one of $Q^1$, $Q^2$, $Q^4$, $Q^5$ and $Q^7$ is R;

R$^1$, R$^{1'}$ and R$^{1'''}$ are independently

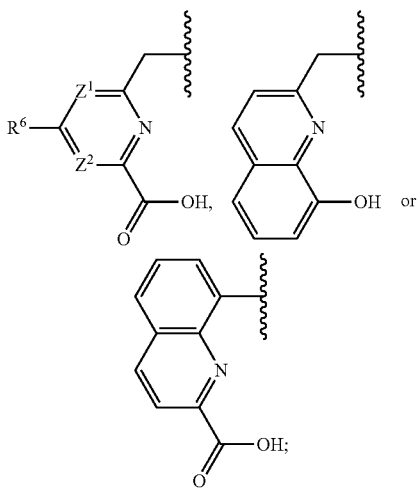

each R$^2$ is independently hydrogen; C$_1$-C$_4$ alkyl or (C$_1$-C$_2$alkyl)phenyl;
each R$^3$, R$^4$ and R$^5$ are independently OH, an —O-protecting group, such as —O—(C$_1$-C$_2$ alkyl) phenyl or —O—C$_{1-4}$alkyl, or a leaving group;
R$^6$ is H; OH; an alkyl-LG or alkoxy-LG, wherein LG is a leaving group; a boronate ester or a leaving group;
X and Y are each independently hydrogen or may be taken with an adjacent X and Y to form an additional carbon-carbon bond;
Z$^1$ and Z$^2$ are independently CH or N;
m is an integer from 0 to 10 inclusive;
n is 0 or 1;
p is 1 or 2;
r is 0 or 1;
w is 0 or 1;
z is 1, 2 or 3;
L is a linker/spacer group covalently bonded to, and replaces one hydrogen atom of the carbon atom to which it is joined, said linker/spacer group being represented by the formula (II):

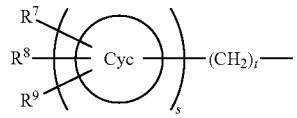
(II)

wherein:
s is an integer of 0 or 1;
t is an integer of 0 to 20 inclusive;
R$^7$, R$^8$ and R$^9$ are independently H; an electrophilic, nucleophilic or electron-rich moiety that allows for covalent attachment to a carrier comprising a biotargeting group, a lipophilic moiety or a biosensor; a protected form or a precursor of the electrophilic, nucleophilic or electron-rich moiety; or a synthetic linker having an electrophilic, nucleophilic or electron-rich moiety that allows for covalent attachment to a carrier comprising a biotargeting group, a lipophilic moiety or a biosensor, or a protected form or a precursor of the electrophilic, nucleophilic or electron-rich moiety of the synthetic linker, and Cyc represents a cyclic aliphatic moiety, aromatic moiety, aliphatic heterocyclic moiety, or aromatic heterocyclic moiety, each of said moieties optionally substituted with one or more groups, which do not interfere with binding to a carrier comprising a biotargeting group, a lipophilic moiety or a biosensor;

or a pharmaceutically acceptable salt thereof, provided that the chelating agent is not 6,6',6'',6'''-((ethane-1,2-diylbis(azanetriyl))tetrakis(methylene))tetrapicolinic acid, 6,6'-((ethane-1,2-diylbis((phosphonomethyl)azanediyl))bis(methylene))dipicolinic acid, 6,6'-((ethane-1,2-diylbis((carboxymethyl)azanediyl))bis(methylene))dipicolinic acid or 6,6'-((ethane-1,2-diylbis((pyridin-2-ylmethyl)azanediyl))bis(methylene))dipicolinic acid.

In one example, the bifunctional chelating agent is of the formula (Ia):

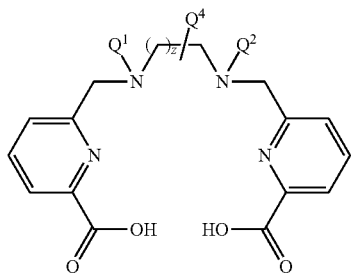

(Ia)

wherein $Q^1$, $Q^2$ and $Q^4$ are as defined above.

The present invention also provides the following examples of the bifunctional chelating agent of formulas (I) and (Ia) defined above:

$Q^1$ and $Q^2$ are each H and $Q^4$ is

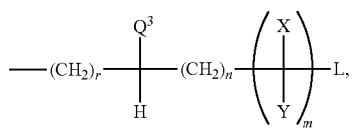

wherein L, X, Y, $Q^3$, m, n and r are as defined above.

$Q^1$ and $Q^2$ are each H and $Q^4$ is

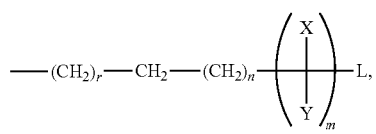

wherein L, X, Y, m, n and r are as defined above.

wherein $Q^1$ and $Q^2$ are each H and $Q^4$ is

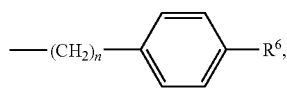

wherein $R^6$ and n are as defined above.

at least one of $Q^1$ and $Q^2$ is

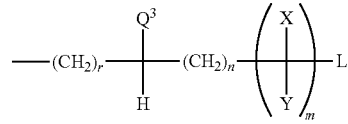

and $Q^4$ is H, wherein L, X, Y, $Q^3$, m, n and r are as defined above.

at least one of $Q^1$ and $Q^2$ is

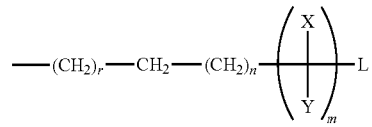

and $Q^4$ is H, wherein L, X, Y, m, n and r are as defined above.

at least one of $Q^1$ and $Q^2$ is

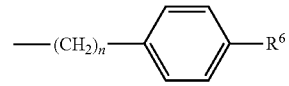

and $Q^4$ is H, wherein $R^6$ and n are as defined above.

at least one of $Q^1$ and $Q^2$ is —$(CHR^2)_p COR^3$ and $Q^4$ is H, wherein $R^2$, $R^3$ and p are as defined above.

at least one of $Q^1$ and $Q^2$ is —$(CHR^2)_p COR^3$ and $Q^4$ is H, wherein $R^3$ is a leaving group and $R^2$ and p is as defined above.

at least one of $Q^1$ and $Q^2$ is —$CH_2COR^3$ and $Q^4$ is H, wherein $R^3$ is as defined above.

at least one of $Q^1$ and $Q^2$ is —$CH_2COR^3$ and $Q^4$ is H, wherein $R^3$ is a leaving group.

at least one of $Q^1$ and $Q^2$ is —$CH_2C{\equiv}CH$ and $Q^4$ is H.

$Q^1$ and $Q^2$ are —$(CHR^2)_p COR^3$ and $Q^4$ is R, wherein $R^2$, $R^3$, and p are as defined above.

The present invention also pertains to the bifunctional chelating agents defined above, wherein $R^6$ is $NO_2$, $NH_2$, isothiocyanato, semicarbazido, thiosemicarbazido, maleimido, bromoacetamido or carboxyl.

In another aspect, the present invention provides a complex comprising the bifunctional chelating agent defined above or a pharmaceutically acceptable salt thereof, and an ion of a stable or radioactive form of a metal selected from a group consisting of Ga, In, Tl, La, Ce, Pr, Nd, Pm, Sm, Eu, Gd, Tb, Dy, Ho, Er, Tm, Yb, Lu, Sc, Y, Ti, Zr, Cr, Mn, Tc, Re, Fe, Ru, Co, Rh, Ir, Ni, Pd, Pt, Cu, Zn, Cd, Hg, Al, Ge, Sn, Pb, Sb, Bi, Te, Po, Mg, Ca, Sr, Ba, Ra, Ac, Th and U.

In a further aspect, the present invention provides a complex comprising the bifunctional chelating agent defined above or a pharmaceutically acceptable salt thereof, and an ion of a stable or radioactive form of a metal selected from a group consisting of $^{66}$Ga, $^{67}$Ga, $^{68}$Ga, $^{111}$In, $^{201}$Tl, $^{142}$Pr, $^{149}$Pm, $^{153}$Sm, $^{153}$Gd, $^{159}$Gd, $^{166}$Ho, $^{175}$Yb, $^{177}$Lu, $^{47}$Sc, $^{90}$Y, $^{89}$Zr, $^{51}$Cr, $^{99m}$Tc, $^{188}$Re, $^{186}$Re, $^{57}$Co, $^{101m}$Rh, $^{62}$Cu, $^{64}$Cu, $^{67}$Cu, $^{117m}$Sn, $^{203}$Pb, $^{212}$Pb, $^{212}$Bi, $^{213}$Bi, $^{223}$Ra, and $^{225}$Ac.

In another aspect, the present invention provides a conjugate of a bifunctional chelating agent of the formula (I) or (Ia) defined above with a carrier comprising a biotargeting moiety, a lipophilic group or a biosensor.

In a further aspect, the present invention provides a conjugate of a bifunctional chelating agent of the formula (I):

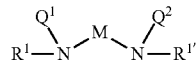
(I)

with a carrier comprising a biotargeting moiety, a lipophilic group or a biosensor,
wherein:
-M- is

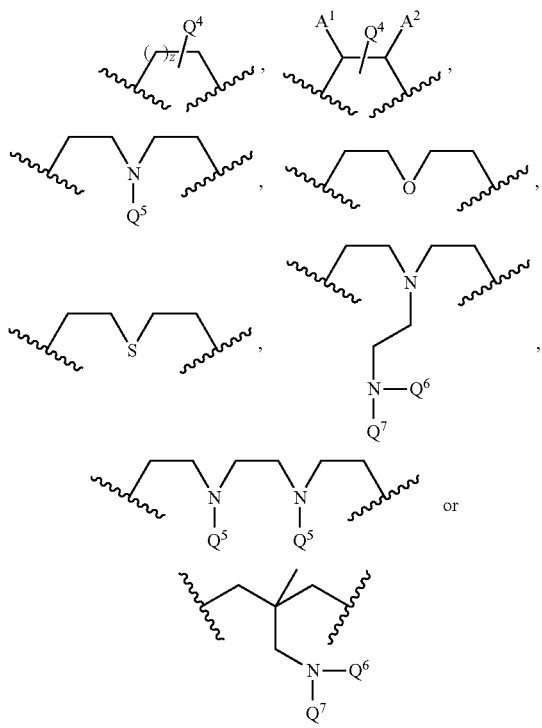

$Q^1$, $Q^2$ and $Q^4$ are independently H or R;
$Q^3$ is H, —$(CHR^2)_wCOR^3$ or —$(CHR^2)_wPO_2R^4R^5$;
$Q^5$ is H, R or $R^{1'''}$;
$Q^6$ is H or $R^{1'''}$;
$Q^7$ is H or R;
$A^1$ and $A^2$ form together with the atoms to which they are attached a $C_6$-$C_{10}$-aryl, $C_6$-$C_{10}$-heteroaryl, $C_3$-$C_{10}$-cycloalkyl or $C_3$-$C_{10}$-heterocyclyl group;
R is —C(O)-L,

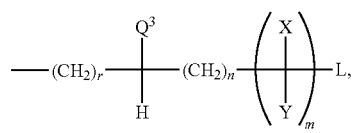

—$(CHR^2)_pCOR^3$ or —$(CHR^2)_pPO_2R^4R^5$, provided that at least one of $Q^1$, $Q^2$, $Q^4$, $Q^5$ and $Q^7$ is R;

$R^1$, $R^{1'}$ and $R^{1'''}$ are independently

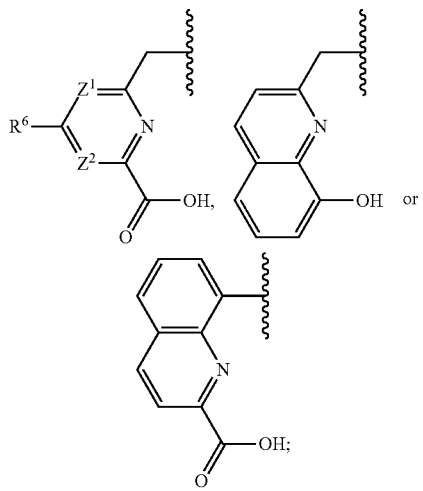

each $R^2$ is independently hydrogen; $C_1$-$C_4$ alkyl or ($C_1$-$C_2$alkyl)phenyl;
each $R^3$, $R^4$ and $R^5$ are independently OH, an —O-protecting group, such as —O—($C_1$-$C_2$ alkyl) phenyl or —O—$C_{1-4}$alkyl, or a leaving group;
$R^6$ is H; OH; an alkyl-LG or alkoxy-LG, wherein LG is a leaving group; a boronate ester or a leaving group;
X and Y are each independently hydrogen or may be taken with an adjacent X and Y to form an additional carbon-carbon bond;
m is an integer from 0 to 10 inclusive;
$Z^1$ and $Z^2$ are independently CH or N;
n is 0 or 1;
p is 1 or 2;
r is 0 or 1;
w is 0 or 1;
z is 1, 2 or 3;
L is a linker/spacer group covalently bonded to, and replaces one hydrogen atom of the carbon atom to which it is joined, said linker/spacer group being represented by the formula (II) or (III):

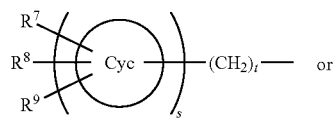
(II)

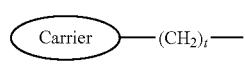
(III)

wherein:
s is an integer of 0 or 1;
t is an integer of 0 to 20 inclusive;
$R^7$, $R^8$ and $R^9$ are independently H; an electrophilic, nucleophilic or electron-rich moiety that allows for covalent attachment to a carrier comprising a biotargeting group, a lipophilic moiety or a biosensor; a protected form or a precursor of the electrophilic, nucleophilic or electron-rich moiety; or a synthetic linker having an electrophilic, nucleophilic or electron-rich moiety that allows for covalent attachment to a carrier comprising a biotargeting group, a lipophilic moiety or a biosensor, or a protected form or a precursor of the electrophilic, nucleophilic or electron-rich moiety of the synthetic linker, and Cyc represents a cyclic aliphatic moiety, aromatic moiety, aliphatic heterocyclic moiety, or aromatic heterocyclic moiety, each of said moieties optionally substituted with one or more groups, which do not interfere with binding to a carrier comprising a biotargeting group, a lipophilic moiety or a biosensor;

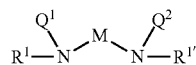

is a moiety comprising a biotargeting group, a lipophilic group or a biosensor, and or a pharmaceutically acceptable salt thereof.

The biotargeting group of the conjugate defined above may be a protein, antibody, antibody fragment, hormone, peptide, growth factor, antigen or hapten.

In a further aspect, the present invention provides a complex comprising (i) a conjugate of a bifunctional chelating agent of the formula (I):

$$R^1-N(Q^1)-M-N(Q^2)-R^{1'} \quad (I)$$

with a carrier comprising a biotargeting moiety, a lipophilic group or a biosensor,
wherein:
-M- is

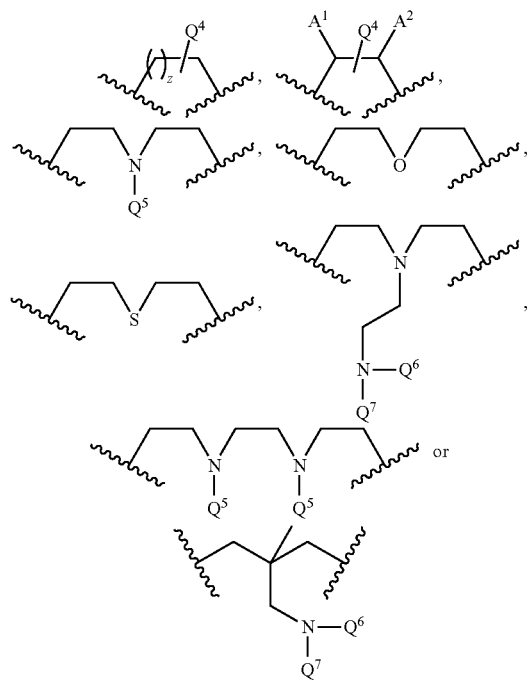

$Q^1$, $Q^2$ and $Q^4$ are independently H or R;
$Q^3$ is H, $-(CHR^2)_w COR^3$ or $-(CHR^2)_w PO_2R^4R^5$;
$Q^5$ is H, R or $R^{1'''}$;
$Q^6$ is H or $R^{1'''}$;
$Q^7$ is H or R;

$A^1$ and $A^2$ form together with the atoms to which they are attached a $C_6$-$C_{10}$-aryl, $C_6$-$C_{10}$-heteroaryl, $C_3$-$C_{10}$-cycloalkyl or $C_3$-$C_{10}$-heterocyclyl group;

R is $-C(O)$-L,

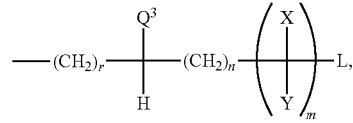

$-(CHR^2)_p COR^3$ or $-(CHR^2)_p PO_2R^4R^5$, provided that at least one of $Q^1$, $Q^2$, $Q^4$, $Q^5$ and $Q^7$ is R;

$R^1$, $R^{1'}$ and $R^{1''}$ are independently

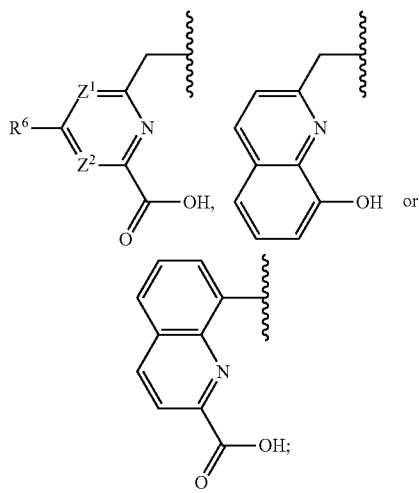

each $R^2$ is independently hydrogen; $C_1$-$C_4$ alkyl or ($C_1$-$C_2$alkyl)phenyl;

each $R^3$, $R^4$ and $R^5$ are independently OH, an —O-protecting group,
such as —O—($C_1$-$C_2$ alkyl) phenyl or —O—$C_{1-4}$alkyl, or a leaving group;

$R^6$ is H; OH; an alkyl-LG or alkoxy-LG, wherein LG is a leaving group; a boronate ester or a leaving group;

X and Y are each independently hydrogen or may be taken with an adjacent X and Y to form an additional carbon-carbon bond;

m is an integer from 0 to 10 inclusive;
$Z^1$ and $Z^2$ are independently CH or N;
n is 0 or 1;
p is 1 or 2;
r is 0 or 1;
w is 0 or 1;
z is 1, 2 or 3;

L is a linker/spacer group covalently bonded to, and replaces one hydrogen atom of the carbon atom to which it is joined, said linker/spacer group being represented by the formula (II) or (III):

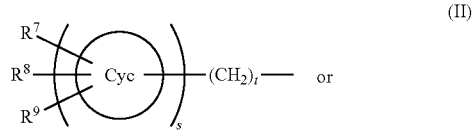

-continued

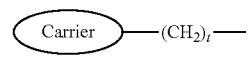
(III)

wherein:
s is an integer of 0 or 1;
t is an integer of 0 to 20 inclusive;
$R^7$, $R^8$ and $R^9$ are independently H; an electrophilic, nucleophilic or electron-rich moiety that allows for covalent attachment to a carrier comprising a biotargeting group, a lipophilic moiety or a biosensor; a protected form or a precursor of the electrophilic, nucleophilic or electron-rich moiety; or a synthetic linker having an electrophilic, nucleophilic or electron-rich moiety that allows for covalent attachment to a carrier comprising a biotargeting group, a lipophilic moiety or a biosensor, or a protected form or a precursor of the electrophilic, nucleophilic or electron-rich moiety of the synthetic linker, and
Cyc represents a cyclic aliphatic moiety, aromatic moiety, aliphatic heterocyclic moiety, or aromatic heterocyclic moiety, each of said moieties optionally substituted with one or more groups, which do not interfere with binding to a carrier comprising a biotargeting group, a lipophilic moiety or a biosensor;

is a moiety comprising a biotargeting group, a lipophilic group or a biosensor, and
or a pharmaceutically acceptable salt thereof, and
(ii) an ion of a stable or radioactive form of a metal selected from a group consisting of Ga, In, Tl, La, Ce, Pr, Nd, Pm, Sm, Eu, Gd, Tb, Dy, Ho, Er, Tm, Yb, Lu, Sc, Y, Ti, Zr, Cr, Mn, Tc, Re, Fe, Ru, Co, Rh, Ir, Ni, Pd, Pt, Cu, Zn, Cd, Hg, Al, Ge, Sn, Pb, Sb, Bi, Te, Po, Mg, Ca, Sr, Ba, Ra, Ac, Th and U.

The present invention also relates to the complex defined above, wherein the ion is an ion of a radioactive metal selected from a group consisting of $^{66}$Ga, $^{67}$Ga, $^{68}$Ga, $^{111}$In, $^{201}$Tl, $^{142}$Pr, $^{149}$Pm, $^{153}$Sm, $^{153}$Gd, $^{159}$Gd, $^{166}$Ho, $^{175}$Yb, $^{177}$Lu, $^{47}$Sc, $^{90}$Y, $^{89}$Zr, $^{51}$Cr, $^{99m}$Tc, $^{188}$Re, $^{186}$Re, $^{57}$Co, $^{101m}$Rh, $^{62}$Cu, $^{64}$Cu, $^{67}$Cu, $^{117m}$Sn, $^{203}$Pb, $^{212}$Pb, $^{212}$Bi, $^{213}$Bi, $^{223}$Ra, and $^{225}$Ac.

The present invention also relates to the complex defined above, wherein the biotargeting moiety is a protein, antibody, antibody fragment, hormone, peptide, growth factor, antigen or hapten.

In a further aspect, the present invention provides a conjugate comprising one of the complexes defined above covalently attached to a biological carrier.

In an example of the above-defined conjugate, the biological carrier is a protein, antibody, antibody fragment, hormone, peptide, growth factor, antigen or hapten.

In a further aspect, the present invention provides a conjugate comprising one of the complexes defined above covalently attached to a biological carrier, such as a protein, antibody, antibody fragment, hormone, peptide, growth factor, antigen or hapten.

In another aspect, the present invention provides a pharmaceutical composition comprising the conjugate defined above, and a pharmaceutically acceptable carrier.

In a further aspect, the present invention provides a method of therapeutic treatment of a mammal having cancer which comprises administering to said mammal a therapeutically effective amount of the pharmaceutical composition defined above.

The present invention also relates to the complex and conjugate defined above, wherein the chelating agent is not 6,6',6'',6'''-((ethane-1,2-diylbis(azanetriyl))tetrakis(methylene)) tetrapicolinic acid, 6,6'-((ethane-1,2-diylbis((phosphonomethyl)azanediyl))bis(methylene))dipicolinic acid, 6,6'-((ethane-1,2-diylbis((carboxymethyl)azanediyl))bis(methylene))dipicolinic acid or 6,6'-((ethane-1,2-diylbis((pyridin-2-ylmethyl)azanediyl))bis(methylene))dipicolinic acid.

DETAILED DESCRIPTION OF THE INVENTION

Figure 1:
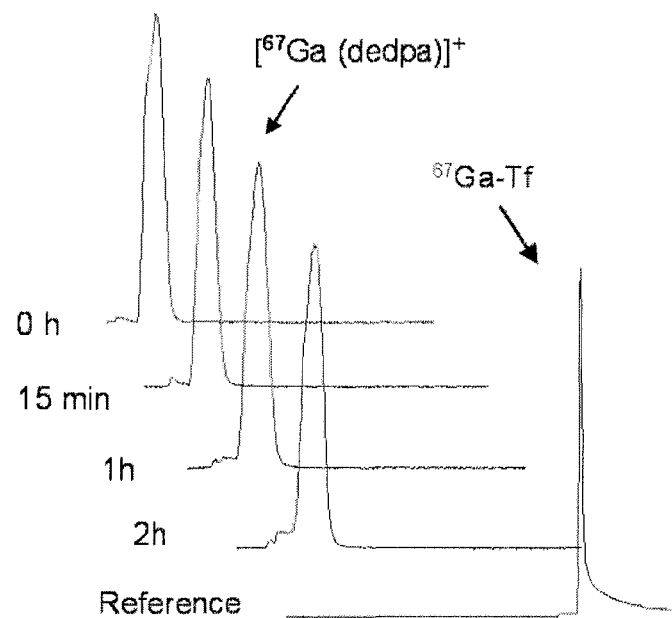
FIG. 1 illustrates HPLC traces of $^{67}$Ga(dedpa)$^+$ vs. apo-transferrin in competition; for reference the trace of $^{67}$Ga-transferrin is shown (gradient: A: NaOAc buffer, pH 4.5, B: MeOH. 0-100% B linear gradient 20 min).

The present invention relates to bifunctional chelating agents, to complexes of these chelating agents with metal ions, and to conjugates of these complexes with a biological carrier. More particularly, the present invention relates to chelates for radiometals useful in molecular imaging and therapy, in particular, to radioisotopes of gallium such as $^{66}$Ga, $^{67}$Ga, and $^{68}$Ga.

For the purposes of promoting an understanding of the principles of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

As used herein, "complex" refers to a complex of the compound of the invention, e.g. Formula (I), complexed with a metal ion, where at least one metal atom is chelated or sequestered.

The complexes of the present invention can be prepared by methods well known in the art. Thus, for example, see Chelating Agents and Metal Chelates, Dwyer & Mellor, Academic Press (1964), Chapter 7. See also methods for making amino acids in Synthetic Production and Utilization of Amino Acids, (edited by Kameko, et al.) John Wiley & Sons (1974). An example of the preparation of a complex involves reacting a bicyclopolyazamacrocyclophosphonic acid with a paramagnetic metal ion under aqueous conditions at a pH from 5 to 7. The complex formed is by a chemical bond and results in a stable paramagnetic nuclide composition, e.g. stable to the disassociation of the paramagnetic nuclide from the ligand.

A "conjugate" refers to a metal-ion chelate that is covalently attached to a carrier, such as a carrier comprising a biotargeting group, a lipohilic group or a biosensor.

The term "alkyl" refers to a straight- or branched chain saturated hydrocarbon group having from 1 to about 20 carbon atoms, including groups having from 1 to about 7 carbon atoms. Examples of alkyl groups include, without limitation, methyl, ethyl, n-propyl, i-propyl, n-butyl, s-butyl, t-butyl, n-pentyl and s-pentyl.

The term "aliphatic heterocyclic moiety" means a non-aromatic mono- or bi-cyclic radicals of three to eight ring atoms in which one or two ring atoms are heteroatoms selected from N, O, or $S(O)_n$ (where n is an integer from 0 to 2), the remaining ring atoms being C.

The term "cyclic aliphatic moiety" means a non-aromatic mono- or bi-cyclic radical of three to eight ring atoms.

The term "aryl" or "aromatic moiety" means a monovalent cyclic aromatic moiety consisting of a mono-, bi- or tricyclic aromatic ring wherein each member of the ring is carbon. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, and diphenylisopropylidenyl.

The term "heteroaryl" or "aromatic heterocyclic moiety" means a monocyclic or bicyclic radical having at least one aromatic ring containing one, two, three or four ring heteroatoms, the remaining ring atoms being carbon, with the understanding that the attachment point of the radical to the remainder of the molecule is on the aromatic ring moiety containing the heteroatom(s). Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, furanyl, pyridyl, pyrrolyl, pyrazolyl, pyrimidyl, quinolinyl, isoquinolinyl, benzofurylbenzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like.

The term "heteroatom" means an atom selected from the group consisting of N, O, P and S.

As used herein, the term "biological targeting group", "biological targeting molecule", "biological targeting moiety", "biotargeting group" or "biological carrier" refers to any biological targeting vector, such as a protein, peptide, peptidomimetic, an antibody, an antibody fragment, a hormone, an aptamer, an affibody molecule, a morpholino compound, a growth factor, an antigen, a hapten or any other carrier, which functions in this invention to recognize a specific biological target site. Antibody and antibody fragment refers to any polyclonal, monoclonal, chimeric, human, mammalian, single chain, dimeric and tetrameric antibody or antibody fragment. Such biological carrier, when attached to a functionalized complex, serves to carry the attached ion to specific targeted tissues.

The term "bifunctional chelating agent" or "bifunctional chelator" refers to compounds that have a chelant moiety capable of chelating a metal ion and a moiety covalently bonded to the chelant moiety that is capable of serving as a means to covalently attach to a biological carrier for example, a molecule having specificity for tumor cell epitopes or antigens, such as an antibody or antibody fragment. Such compounds are of great utility for therapeutic and diagnostic applications when they are, for example, complexed with radioactive metal ions and covalently attached to a specific antibody. These types of complexes have been used to carry radioactive metals to tumor cells which are targeted by the specificity of the attached antibody see, for example, Meares et al., Anal. Biochem. 142, 68-74 (1984); Krejcarek et al., Biochem. Biophys. Res. Comm. 77, 581-585 (1977).

The bifunctional chelating agents described herein (represented by Formula I) can be used to chelate or sequester a metal ion to form metal-ion chelates (also referred to herein as "complexes", as defined above). The complexes, because of the presence of the functionalizing moiety (represented by $R^6$ in Formula I), can be covalently attached to a biologically active material, such as dextran, molecules that have specific affinity for a receptor, affibody molecules, morpholino compounds or antibodies or antibody fragments. The term "antibody" refers to a polyclonal antibody, a monoclonal antibody, a chimeric antibody, a heteroantibody, or a fragment thereof. Antibodies used in the present invention may be directed against, for example, cancer, tumors, bacteria, fungi, leukemias, lymphomas, autoimune disorders involving cells of the immune system, normal cells that need to be ablated such as bone marrow and prostate tissue, virus infected cells including HIV, parasites, mycoplasma, differentiation and other cell membrane antigens, pathogen surface antigens, toxins, enzymes, allergens, drugs and any biologically active molecules. Some examples of antibodies are HuM195 (anti-CD33), CC-11, CC-46, CC-49, CC-49 F(ab')$_2$, CC-83, CC-83 F(ab')$_2$, and B72.3, 1116-NS-19-9 (anti-colorectal carcinoma), 1116-NS-3d (anti-CEA), 703D4 (anti-human lung cancer), and 704A1 (anti-human lung cancer). The hybridoma cell lines 1116-NS-19-9, 1116-NS-3d, 703D4, 704A1, CC49, CC83 and B72.3 are deposited with the American Type Culture Collection, having the accession numbers ATCC HB 8059, ATCC CRL 8019, ATCC HB 8301, ATCC HB 8302, ATCC HB 9459, ATCC HB 9453 and ATCC HB 8108, respectively.

Antibody fragment includes Fab fragments and F(ab')$_2$ fragments, and any portion of an antibody having specificity toward a desired epitope or epitopes.

Complexes of the present invention, which include a radioisotopic metal ion having a relatively short half-life, such as Ga-68, can be conjugated with biological carriers having relatively short or relatively long biological clearance times from a subject. For radioimaging, however, such complexes are typically conjugated to biological carriers having a biological clearance time that is within the lifetime of the short-lived radioisotope so that the systemic background signal produced by unbound conjugated complex can be sufficiently reduced in time to permit imaging of the conjugated complex bound to the target site of the biological carrier.

Examples of "biological carriers" or "biotargeting carriers", which can be conjugated to complexes of the present invention, include peptides or molecular constructs, such as mini-bodies, nano-bodies or affi-bodies. Specific examples of peptides having relatively short clearance times are described in Maecke H R and Reubi J C 2008 Peptide based probes for cancer imaging. J. Nucl. Med. 49:1735-38; Krenning, E P, de Jong M, Kooij P P, Breeman, W A, Bakker W H et. al. 1999 Radiolabelled somatostatin analogue(s) for peptide receptor scintigraphy and radionuclide therapy. Ann. Oncol. 10 Supp12:S23-29; Haubner R and Decristoforo C. 2009 Radiolabelled RGD peptides and peptidomimetics for tumour targeting. Front. Biosci. 14:872-86; Ananias H J, de Jong M, Dierckx R A, et al. 2008 Nuclear imaging of prostate cancer with gastrin-releasing-peptide-receptor targeted radiopharmaceuticals. Curr. Pharm. Des. 14(28) 3033-47; Breeman W A, Kwekkeboom D J, de Blois E, de Jong M, et al. 2007 Radiolabelled regulatory peptides for imaging and therapy. Anticancer Agents Med. Chem. 7(3):345-57; Schroeder R P, van Weerden W M, Bangma C,. et al. 2009 Peptide receptor imaging of prostate cancer with radiolabelled bombesin analogues. Methods 48(2):200-4, the disclosures of which are incorporated by reference herein.

Complexes of the present invention can also be conjugated to non-biological carriers, such as carriers comprising lipophilic groups, such as phenyl groups having one, two or three alkoxy groups, for example, one, or more than one 1-methoxyphenyl, 1,3-dimethoxyphenyl, or 1,3,5-trimethoxyphenyl group, to increase the lipophilicity of the complexes to which they are conjugated. Other non-limiting examples of lipophilic groups include $C_1$-$C_6$-alkyl, $C_1$-$C_6$-alkoxy-$C_1$-$C_6$-alkyl, acetal and $C_1$-$C_6$-alkyl-crown ether groups (e.g., —CH$_2$-12-crown-4, —CH$_2$-15-crown-5 and —CH$_2$-18-crown-6 groups). The resulting conjugates are useful for imaging myocardial blood flow.

Alternatively, complexes of the present invention can be conjugated to carriers comprising a biosensor, such as a nitroimidazole group for targeting hypoxia. Examples of such nitromidazole groups are shown by the following formula.

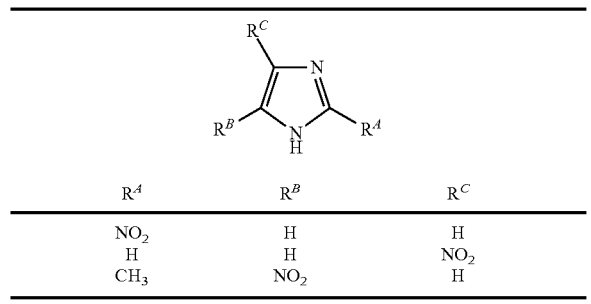

| $R^A$ | $R^B$ | $R^C$ |
|---|---|---|
| NO$_2$ | H | H |
| H | H | NO$_2$ |
| CH$_3$ | NO$_2$ | H |

Conjugated carriers comprising nitroimidazole derivatives are reduced to a chemical form that is trapped in hypoxic tissue so that a radio-tracer complexed to the chelator of the conjugate builds in concentration selectively compared to normal tissue.[25]

When using the term "radioactive metal chelate/antibody conjugate" or "conjugate", the "antibody" is meant to include whole antibodies and/or antibody fragments, including semi-synthetic or genetically engineered variants thereof Such antibodies normally have a highly specific reactivity.

The antibodies or antibody fragments which may be used in the conjugates described herein can be prepared by techniques well known in the art. Highly specific monoclonal antibodies can be produced by hybridization techniques well known in the art, see for example, Kohler and Milstein Nature, 256, 495-497 (1975); and Eur. J. Immunol., 6, 511-519 (1976). Such antibodies normally have a highly specific reactivity in the antibody targeted conjugates, antibodies directed against any desired antigen or hapten may be used. Preferably the antibodies which are used in the conjugates are monoclonal antibodies, or fragments thereof having high specificity for a desired epitope(s).

As used herein, "pharmaceutically-acceptable salt" means any salt or mixture of salts of a complex or conjugate of formula (I) which is sufficiently non-toxic to be useful in therapy or diagnosis of animals, preferably mammals. Thus, the salts are useful in accordance with this invention. Representative of those salts formed by standard reactions from both organic and inorganic sources include, for example, sulfuric, hydrochloric, phosphoric, acetic, succinic, citric, lactic, maleic, fumaric, palmitic, cholic, palmoic, mucic, glutamic, gluconic, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium or 1-deoxy-1-(methylamino)-D-glucitol, alkali metal ions, alkaline earth metal ions, and other similar ions. Particularly preferred are the salts of the complexes or conjugates of formula (I) where the salt is potassium, sodium or ammonium. Also included are mixtures of the above salts.

The present invention may be used with a physiologically acceptable carrier, excipient or vehicle therefor. The methods for preparing such formulations are well known. The formulations may be in the form of a suspension, injectable solution or other suitable formulations. Physiologically acceptable suspending media, with or without adjuvants, may be used.

An "effective amount" of the formulation is used for diagnosis or for therapeutic treatments of diseases. The dose will vary depending on the disease and physical parameters of the animal, such as weight. In vivo diagnostics are also contemplated using formulations of this invention.

The chelates of the present invention are useful for binding radioisotopes to biological targeting molecules in order to produce constructs for molecular imaging and therapy, more specifically to produce constructs comprising gallium radioisotopes for molecular imaging.

Other uses of some of the chelates of the present invention may include the removal of undesirable metals (i.e. iron) from the body, attachment to polymeric supports for various purposes, e.g. as diagnostic agents, and removal of metal ion by selective extraction.

The free acid of the compounds of formula (I) may be used, also the protonated form of the compounds, for example when the carboxylate is protonated and/or the nitrogen atoms, i.e. when the HCl salt is formed.

The complexes so formed can be attached (covalently bonded) to an antibody or fragment thereof and used for therapeutic and/or diagnostic purposes. The complexes and/or conjugates can be formulated for in vivo or in vitro uses. A preferred use of the formulated conjugates is the diagnosis of diseased states (e.g., cancer) in animals, especially humans.

Biotargeted radiopharmaceuticals that employ the chelating agent (ligand) of the present invention to secure a metal radionuclide can be prepared by two methods: 1) Pre-complexation—the metal ligand complex (chelate) can first be prepared followed by covalent attachment of the chelate to a biotargeting group, for example a monoclonal antibody; 2) Post-complexation—a covalent conjugate between the ligand and the biotargeting molecule can be prepared in a first step followed by introduction and complexation of the metal radionuclide. Both methods have merits and shortcomings. Method 1 is appealing from the standpoint that forcing conditions can be utilized to facilitate complexation however subsequent attachment of the complex to a targeting vector requires more elaborate chemical transformation that can be difficult to perform rapidly in a hospital setting. In contrast, method 2 is desirable since it allows the more intricate chemistry required for conjugation of the ligand and targeting vector to be performed in controlled environment without time constraints introduced by the radionuclide. The complexation step can then be conducted onsite at the hospital pharmacy by clinical technicians however this step can be problematic since the ligand bound conjugate is much more sensitive to rigorous conditions that favor rapid and complete complexation.

Of the two approaches for preparing biotargeted radiopharmaceuticals, the post-complexation strategy is clearly the most desirable if appropriate ligands and/or conditions can be devised that facilitate rapid and complete incorporation of the radionuclide. In addition, structural and conformational components can be introduced that can minimize kinetic barriers to complexation. For example, molecular architecture which can enhance pre-organization of the ligand binding site toward the necessary conformational requirements of the metal ion should produce faster complexation kinetics.

The bifunctional chelating agents described herein (represented by formula I) are designed to form thermodynamically stable and kinetically inert complexes with the main group series of metals. Complexation kinetics can be modulated by altering backbone structural rigidity, electronic character of the coordinate donor atoms, and conformational accessibility of the metal binding site.

While not wishing to be bound by theory, it is believed that kinetic advantages associated with the present invention are a function of structural modifications that lead to preferred molecular geometries (pre-organization) which match ligating requirements of the metal. In this manner the ligand-metal binding event is accelerated without the need for harsh reaction conditions.

In the context of bifunctional chelating agents, the generation of optimal pre-organized ligand structures conducive to rapid complexation kinetics is significantly influenced by the judicious placement of the linking group. In this manner, the linking group can be engineered to assume a position distant from the metal binding site during the initial stages of the metal docking process followed by the adoption of a secondary conformation induced by complexation that effectively shields the metal from reversible dissociation pathways. The positional orientation of the linking group also affects the electronic nature of the coordinate donor atoms and their juxtaposed lone pair electrons which are critical for satisfying the geometric requirements of the metal ion.

The present invention also includes formulations comprising the conjugates of this invention and a pharmaceutically acceptable carrier, especially formulations where the pharmaceutically acceptable carrier is a liquid.

The present invention is also directed to a method of therapeutic treatment of a mammal having cancer which comprises administering to said mammal a therapeutically effective amount of the formulation of this invention.

Thus, the present invention may be practiced with the conjugate of the present invention being provided in a pharmaceutical formulation, both for veterinary and for human medical use. Such pharmaceutical formulations comprise the active agent (the conjugate) together with a physiologically acceptable carrier, excipient or vehicle therefore. The methods for preparing such formulations are well known. The carrier(s) must be physiologically acceptable in the sense of being compatible with the other ingredient(s) in the formulation and not unsuitably deleterious to the recipient thereof. The conjugate is provided in a therapeutically effective amount, as described above, and in a quantity appropriate to achieve the desired dose.

Complexes of the chelating agents of the present invention with a suitable metal ion, and conjugates of these complexes can be used in diagnostic medical imaging procedures. For example, complexes of the present invention formed with a positron-emitter and the corresponding conjugates of these complexes are useful for positron-emission tomography (PET) imaging. In addition, complexes of the present invention formed with a gamma-emitter and the corresponding conjugates are useful for single-photon-emission computed tomography (SPECT) imaging. Furthermore, complexes of the present invention formed with a paramagnetic metal ion, such as $Gd^{+3}$, $Mn^{-2}$ or $Fe^{+3}$, and corresponding conjugates of these complexes can act as contrast agents in magnetic resonance imaging (MRI), and complexes of the present invention formed with a lanthanide metal ion such as, $Tb^{3-}$, $Eu^{3+}$, $Sm^{3+}$ or $Dy^{3+}$, and the corresponding conjugates can be used in fluorescent imaging.

This invention is used with a physiologically acceptable carrier, excipient or vehicle therefore. The formulations may be in the form of a suspension, injectable solution or other suitable formulations. Physiologically acceptable suspending media, with or without adjuvants, may be used.

The formulations include those suitable for parenteral (including subcutaneous, intramuscular, intraperitoneal, intratumoral, and intravenous), oral, rectal, topical, nasal, or ophthalmic administration. Formulations may be prepared by any methods well known in the art of pharmacy. Such methods include the step of bringing the conjugate into association with a carrier, excipient or vehicle therefore. In general, the formulation may be prepared by uniformly and intimately bringing the conjugate into association with a liquid carrier, a finely divided solid carrier, or both, and then, if necessary, shaping the product into desired formulation. In addition, the formulations of this invention may further include one or more accessory ingredient(s) selected from diluents, buffers, binders, disintegrants, surface active agents, thickeners, lubricants, preservatives, and the like. In addition, a treatment regime might include pretreatment with non-radioactive carrier.

Injectable compositions of the present invention may be either in suspension or solution form. In the preparation of suitable formulations it will be recognized that, in general, the water solubility of the salt is greater than the acid form. In solution form the complex (or when desired the separate components) is dissolved in a physiologically acceptable carrier. Such carriers comprise a suitable solvent, preservatives such as benzyl alcohol, if needed, and physiologically compatible buffers. Useful solvents include, for example, water, aqueous alcohols, glycols, and phosphonate or carbonate esters. Such aqueous solutions contain no more than 50 percent of the organic solvent by volume. Examples of suitable buffers include the sodium, potassium or ammonium salts of weak acids, for example carbonates, phosphates, glycinates or arginates, N-methylglucosaminate or other amino acids, Tris, HEPES, MOPS, THAM or EPPS.

Injectable suspensions are compositions of the present invention that require a liquid suspending medium, with or without adjuvants, as a carrier. The suspending medium can be, for example, aqueous polyvinylpyrrolidone, inert oils such as vegetable oils or highly refined mineral oils, polyols, or aqueous carboxymethylcellulose. Suitable physiologically acceptable adjuvants, if necessary to keep the complex in suspension, may be chosen from among thickeners such as carboxymethylcellulose, polyvinylpyrrolidone, gelatin, and the alginates. Many surfactants are also useful as suspending agents, for example, lecithin, alkylphenol, polyethyleneoxide adducts, naphthalenesulfonates, alkylbenzenesulfonates, and polyoxyethylene sorbitan esters.

Examples of methods for preparing the chelators of the present invention having picolinic acid moieties are illustrated in Scheme 1. In one example, diamino compound 5 is first alkylated with two equivalents of tert-butyl 6-(bromomethyl)picolinate 2 to form dipicolinate ester 6, which can be either deprotected to form dipicolinic acid derivative 8 or alkylated with an alkyl halide or allowed to react with an acyl halide to form the alkylated or amidated derivative 7, which is then deprotected to form alkylated (amidated), dipicolinic acid derivative 9. Intermediate 6 can alternatively be formed by reacting diamino compound 5 with two equivalents of methyl 6-formylpicolinate 4 to form a diimine intermediate, which is reduced using $NaBH_4$. Another approach of producing intermediate 7 is to allow two equivalents of 2 or 4 to react with an alkylated or amidated form of Compound 5 (Compound 10). Reactant 2 can be formed by bromination of tert-butyl 6-methylpicolinate 1. Reactant 4 can be prepared by reducing dimethyl pyridine-2,6-dicarboxylate 3 to the corresponding monoalcohol using $NaBH_4$ followed by oxidation of the alcohol to an aldehyde using $SeO_2$.

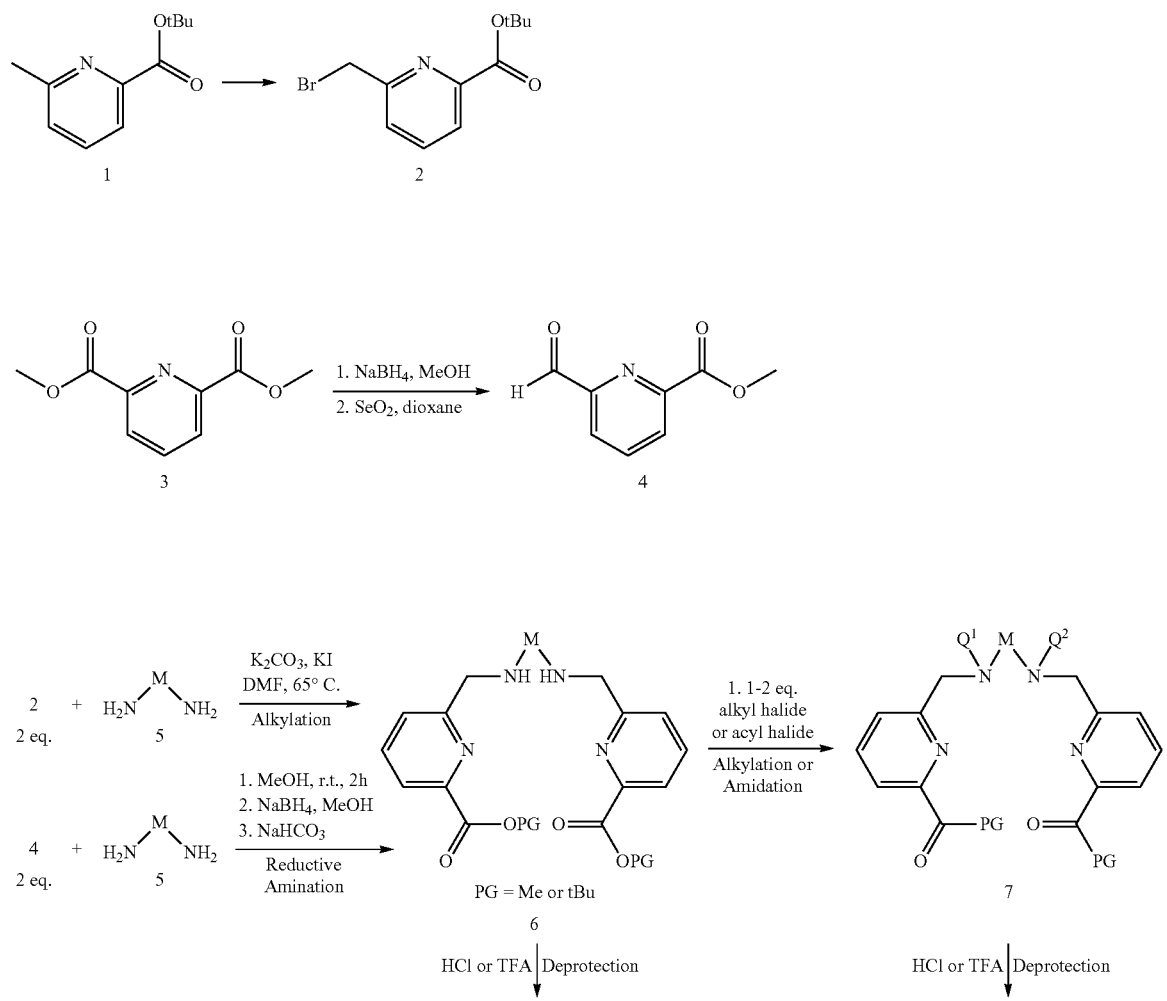

Scheme 1. General Synthetic scheme for forming the bifunctional chelators of the present invention

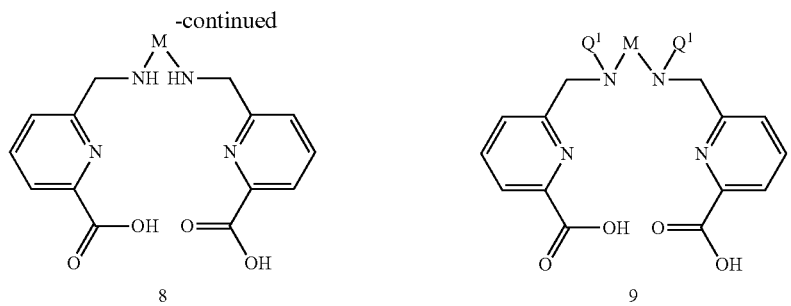

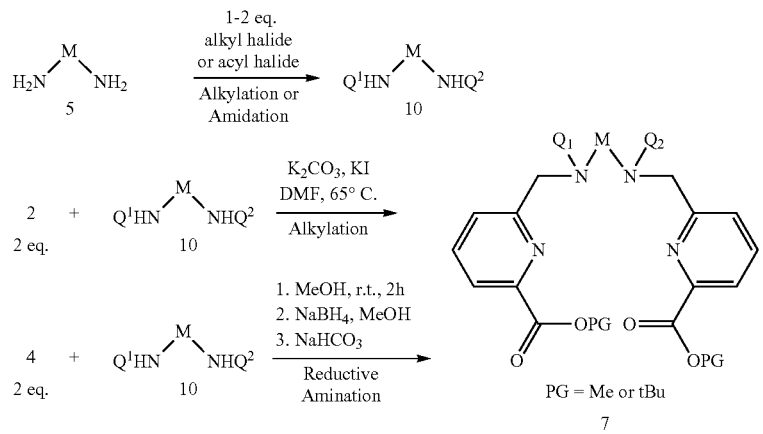

Scheme 2 illustrates examples of methods for preparing the chelators of the present invention having picolinic acid groups and derived from 2-(aminomethyl)-2-methylpropane-1,3-diamine (14a) and N1,N1-bis(2-aminoethyl)ethane-1,2-diamine (14b). Diamino compound 14 is first alkylated with two to three equivalents of tert-butyl 6-(bromomethyl)picolinate 2 to form di- or tri-picolinate ester 15, which can be either deprotected to form di- or tri-picolinic acid derivative 17 or further alkylated with an alkyl halide or allowed to react with an acyl halide to form an alkylated or amidated derivative, which is subsequently deprotected to form alkylated (amidated), di- or tri-picolinic acid derivative 16.

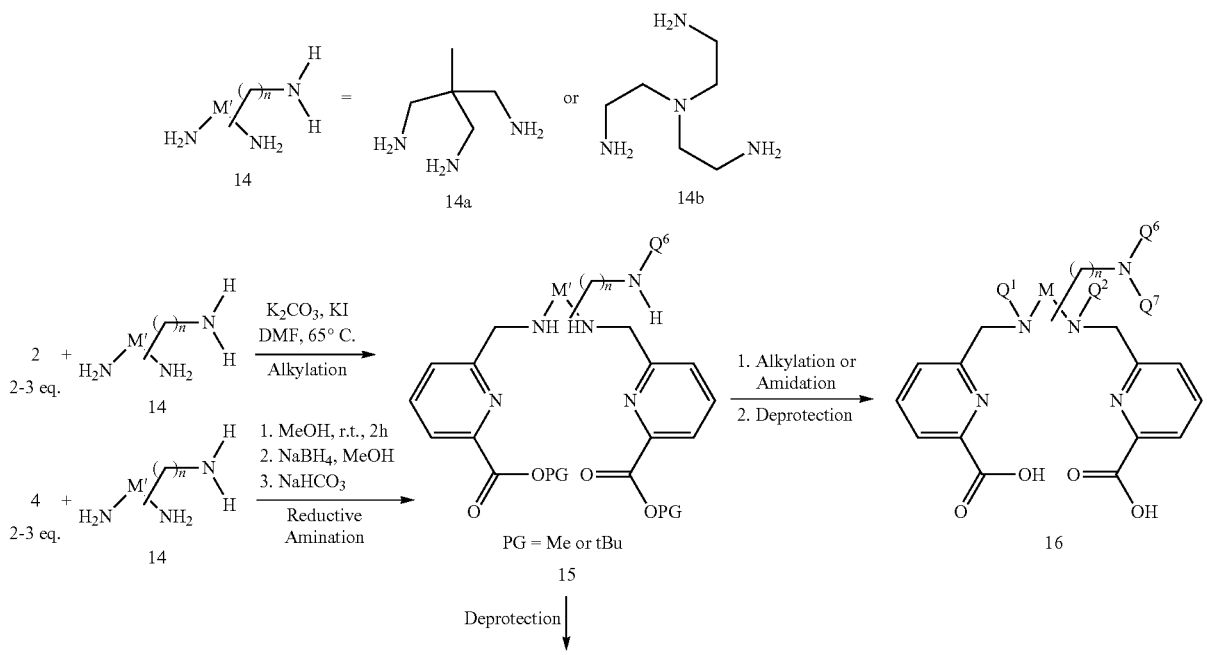

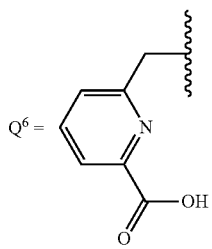
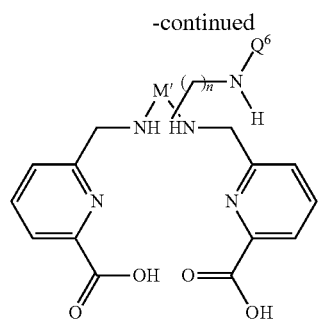

The chelates of the present invention having picolinic acid moieties and derived from alkylene diamine groups can be prepared by the synthetic approach illustrated in Scheme 3, which initially involves selective single alkylation of the primary amines of an alkylene diamine (18f), a backbone-substituted alkylene diamine (18a), a mono- or di-, N-alkylated alkylene diamine (18d-e) or a backbone-substituted and mono- or di-, N-alkylated alkylene diamine (18b-c) with a 6-(bromomethyl)picolinate derivative protected with a base stable, acid labile carboxy-protecting group, such as tert-butyl 6-(bromomethyl)picolinate (2), which can be formed by bromination of tert-butyl 6-methylpicolinate (1), to form alkylated product (19a-f) (See T. Pandiyan et al., Inorg. Chim. Acta, 2003, 343, 79-89, the disclosure of which is incorporated by reference herein). The chelates of the present invention having pyrimidine-2-carboxylic acid groups, pyrimidine-4-carboxylic acid groups or 1,3,5-triazine-2-carboxylic acid groups can be prepared starting from tert-butyl 4-(bromomethyl)pyrimidine-2-carboxylate, tert-butyl 2-(bromomethyl)pyrimidine-4-carboxylate, and tert-butyl 4-(bromomethyl)-1,3,5-triazine-2-carboxylate, respectively. Similarly, the chelates of the present invention having quinolinyl-8-ol groups or quinoline-2-carboxylic acid groups can be prepared starting from 2-(bromomethyl)-8-(tert-butoxy)quinoline and tert-butyl 7-bromoquinoline-2-carboxylate, respectively.

Compounds (18b) and (18c) may be prepared by selective single alkylation of the primary amines of diamine (18a) using 1 or 2 equivalents of an alkylating agent R-L, where L is a leaving group. Compounds (18e) and (18d) may be similarly prepared starting from diamine (18f). The functional group of the R group of diamine (18a) may need to be protected prior to the alkylation reaction used to prepare compound (18b) or (18c) to prevent any undesirable side reactions taking place between the functional groups of the substituent R of diamine (18a) and the alkylating agent R-L. The protecting group can be removed after a later conjugation step involving a carrier, such as a carrier comprising a biological targeting moiety, which is used to form the conjugated bifunctional chelate of the present invention. Examples of suitable protecting groups for use in the method of the present invention may be found in Kocienski, P. J. Protecting Groups, 3rd ed.; Georg Thieme Verlag: New York, 2005, the disclosure of which is incorporated by reference herein.

When compound 18a, 18b or 18e is used as a starting material for forming a bifunctional chelating agent, any free secondary amines in the resulting dipicolinic acid derivative (19a, 19b or 19e) may then be protected with a suitable protecting group, for example, an acid-labile protecting group, such as a t-butyl carbamate (BOC) protecting group, to prevent undesired couplings taking place in a subsequent conjugation reaction involving a carrier (See Tarbell et al., Procl. Natl. Acad. Sci., 1972, 69, 730, the disclosure of which is incorporated.)

In the case where one or more of the substituents of the alkylene diamine moieties of (19a-e) are ester groups, the synthetic method of the present invention for forming a conjugated bifunctional chelator would include a step of hydrolysing these ester groups under basic conditions, using a suitable base such as LiOH, to form the corresponding acids (See Corey et al., Tetrahedron Lett., 1977, 3529, the disclosure of which is incorporated by reference herein.)

Coupling of (19a-e) or the corresponding acids with a biological carrier of interest may then be carried out to form a stable linkage, such as an amide linkage, between the chelating agent (19a-e) and the carrier. (See Nakajima et al., Bioconjugate Chem., 1995, 6, 123, the disclosure of which is incorporated by reference herein.)

Finally, if necessary, deprotection of the carboxylic acid protecting groups of the picolinyl moieties is carried out to afford the final bifunctional chelate. (See Chandrasekaran et al., J. Org. Chem., 1977, 42, 3972, the disclosure of which is incorporated by reference herein.)

Scheme 3. Synthetic scheme for forming the bifunctional chelators of the present invention derived from an alkylene diamine moiety

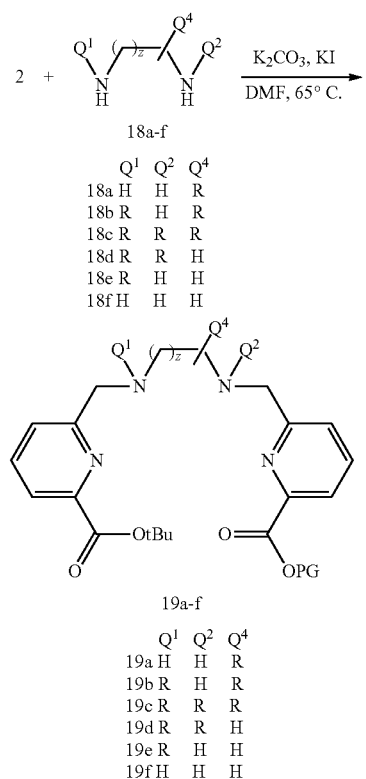

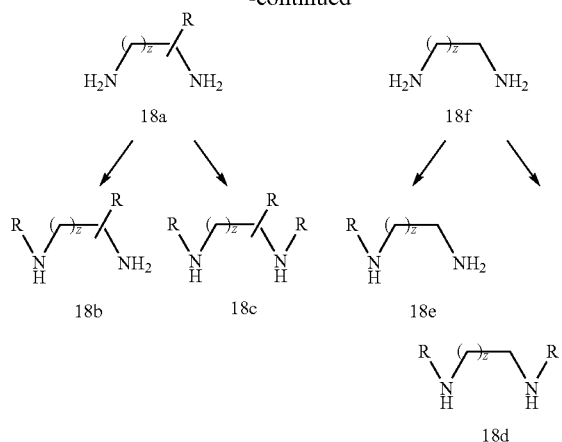

Scheme 4 illustrates examples of methods for preparing the chelators of the present invention having picolinic acid groups and derived from N1-(2-aminoethyl)ethane-1,2-diamine 19 (n=1) and N1,N1'-(ethane-1,2-diyl)bis(ethane-1,2-diamine) 19 (n=2). To produce chelators having the primary amino groups and a secondary amino group of the starting polyamino compound 19 alkylated with a picolinic acid group, the primary amino groups of Compound 19 are first protected with benzyl groups and then the resulting dibenzylated compound 20 is allowed to react with 3-4 equivalents of an alkylating group containing a picolinic acid ester group ($R^{1a''}$—Br) to produce protected intermediate 21. The benzyl groups of this compound are then removed using 10 mol % Pd/C to produce intermediate 22 having protected picolinic acid groups. The ester groups of intermediate 22 can either be hydrolyzed to produce chelate 22a or intermediate 22 may be allowed to react with 1-4 equivalents of an alkyl halide or acyl halide to produce the protected bifunctional chelate 23, which can subsequently be deprotected to produce bifunctional chelate 23a.

In an alternate example, only the primary amino groups of starting compound 19 are alkylated with a picolinyl acid ester moiety to produce intermediate 19a. Intermediate 19a may then be deprotected to produce chelate 19b or reacted with 1-4 equivalents of an alkyl halide or an acyl halide and the resulting poly-alkylated (amidated) protected intermediate deprotected to produce bifunctional chelator 19c.

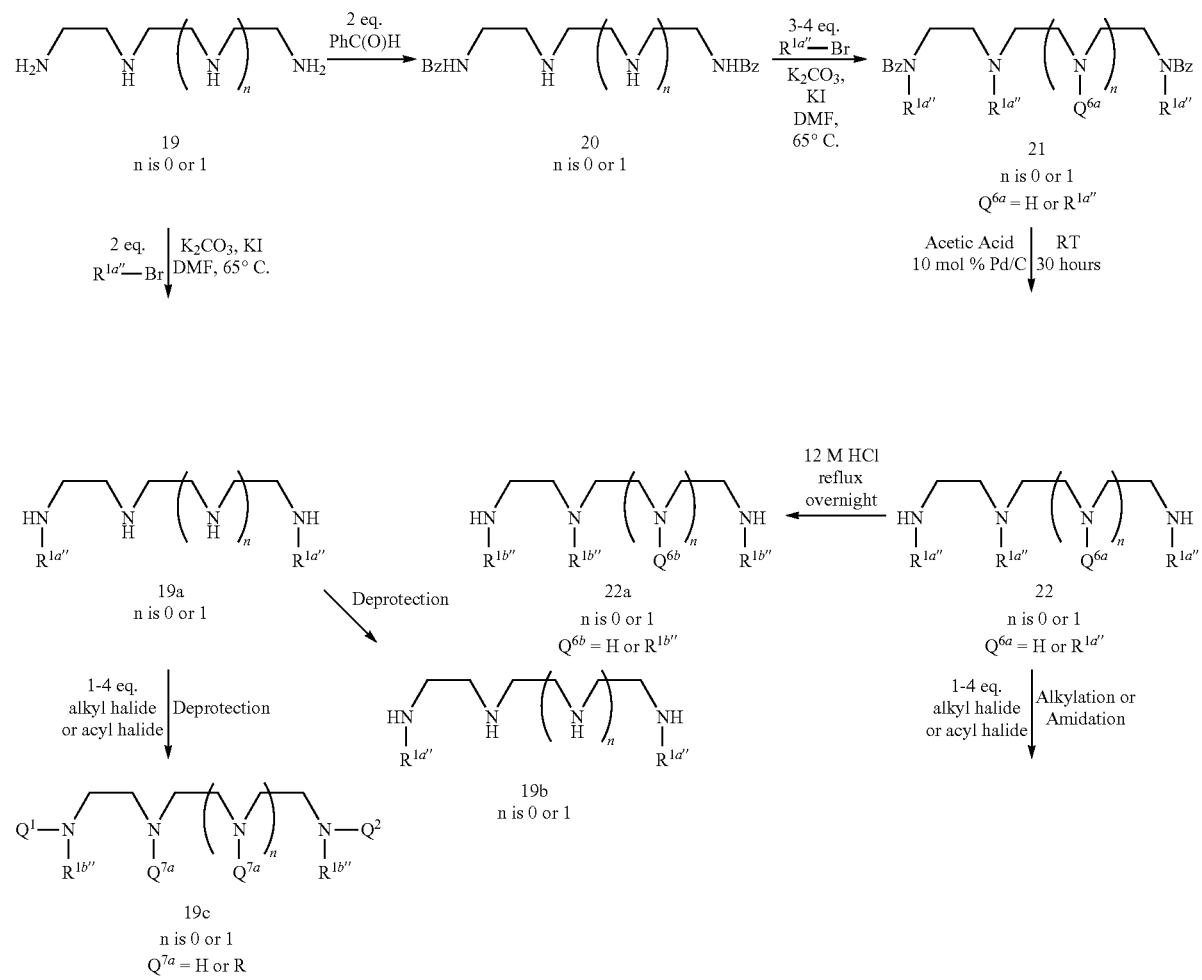

Scheme 4. Example of synthetic scheme for forming bifunctional chelators of the present invention derived from N1-(2-aminoethyl)ethane-1,2-diamine and N1,N1'–(ethane-1,2-diyl)bis(ethane-1,2-diamine) having two or more pendant picolinic acid groups

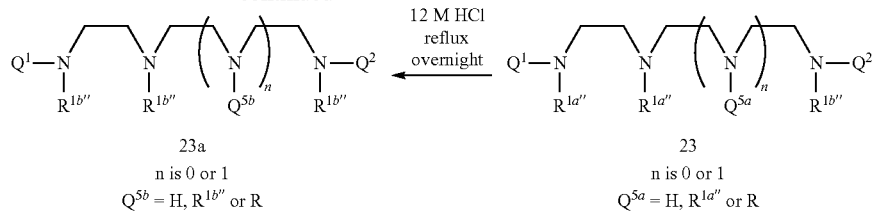

23a
n is 0 or 1
$Q^{5b}$ = H, $R^{1b''}$ or R 23
n is 0 or 1
$Q^{5a}$ = H, $R^{1a''}$ or R

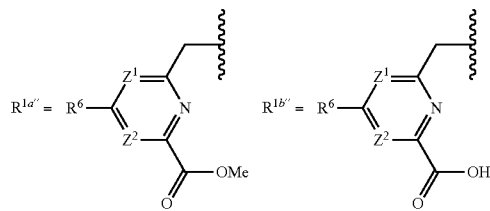

Scheme 5 shows examples of synthetic schemes for forming chelators of the present invention, which include pendant 2-methylquinolin-8-ol and quinoline-2-carboxylic acid groups for chelation. To form bifunctional chelating agents having pendant methyl 8-hydroxyquinoline-2-carboxylate groups (27), the alcohol group of methyl 8-hydroxyquinoline-2-carboxylate 24 is first protected using TBSC to produce protected intermediate methyl 8-((tert-butyldimethylsilyl)oxy)quinoline-2-carboxylate 25. The ester group of Compound 25 is then converted to an aldehyde group through a reductive step using $NaBH_4$ to produce an alcohol, which is oxidized to aldehyde 26 using $SeO_2$. Reaction of diamino compound 5 with two equivalents of aldehyde 26 by way of reductive amination following by deprotection of the alcohol results in chelate 27, which may be further reacted, if necessary, to form a bifunctional chelator. Chelators of the present invention having pendant quinoline-2-carboxylic acid groups can be formed by first converting alcohol 24 to bromide 28 using $NBS/PPh_3$. Alkylation of diamino compound 5 with bromide 28 is then conducted under Buchwald/Hartwig reaction conditions to afford chelator 29, which may be further alkylated, if necessary, to form a bifunctional chelator of the present invention.

Scheme 5. Example of synthetic schemes for forming chelators having pendant 2-methylquinolin-8-ol and quinoline-2-carboxylic acid groups.

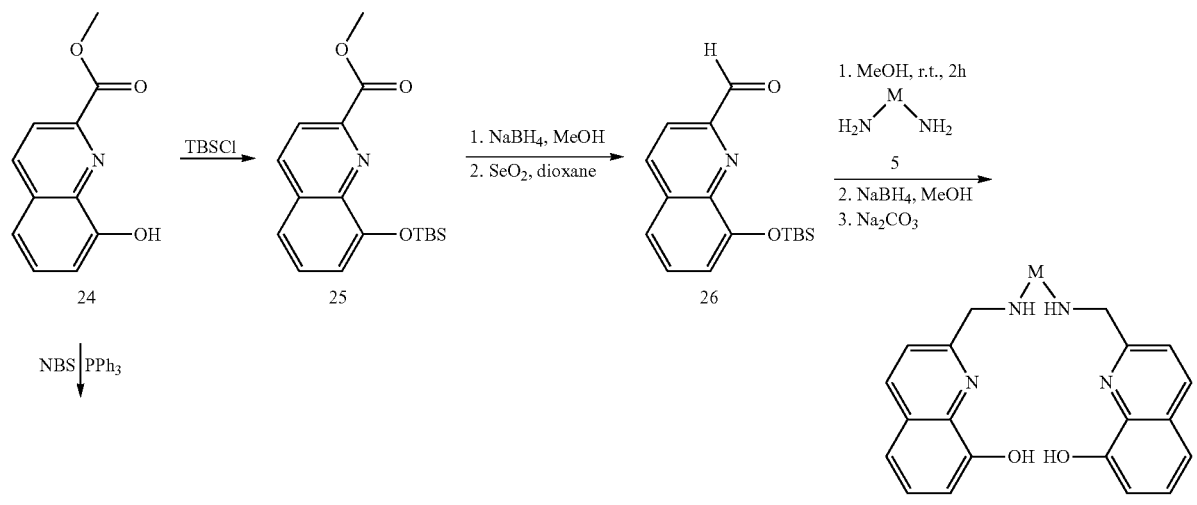

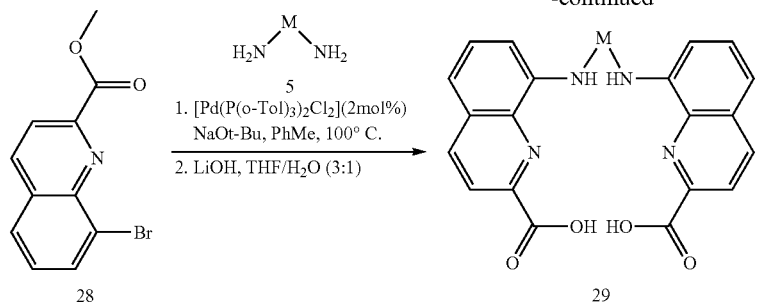

Scheme 6 illustrates examples of forming conjugates from chelators of the present invention. In one example, the amino groups of a chelator 6a are alkylated with 2 equivalents of a carrier molecule having a pendant bromide group (30) and the picolinate ester moieties of the resulting intermediate are then hydrolyzed to form di-N-alkylated conjugate 31. In another example, a chelator having a pendant carboxylic acid group (32) is coupled with a carrier having a pendant amino group (33) to form an amide linkage and the picolinate ester moieties of the resulting intermediate are subsequently hydrolyzed to form conjugate 34. Alternatively, a chelator having a pendant isothiocyanate group (37) can be coupled to carrier 33 to form a conjugate having a thiourea linkage (38).

Chelator 37 can be produced starting from a di-N-benzylated chelator having a Ph-NO$_2$ group moiety disposed along the alkylene diamine backbone (35a). Hydrogenation of chelator 35a using a Pd(OH)$_2$ catalyst results in the reduction of the Ph-NO$_2$ group and deprotection of the secondary amino groups of that compound. The ester groups of the resultant intermediate are then hydrolyzed under basic conditions to afford a molecule having a Ph-NH$_2$ group and picolinic acid groups (36), which is subsequently converted to Compound 37 by reaction with SCCl$_2$. Compound 35a is produced by alkylating dibenzylated alkylenediamine 35 with 2 equivalents of methyl 6-(bromomethyl)picolinate.

Scheme 6. Examples of synthetic schemes for forming conjugates from bifunctional chelators of the present invention.

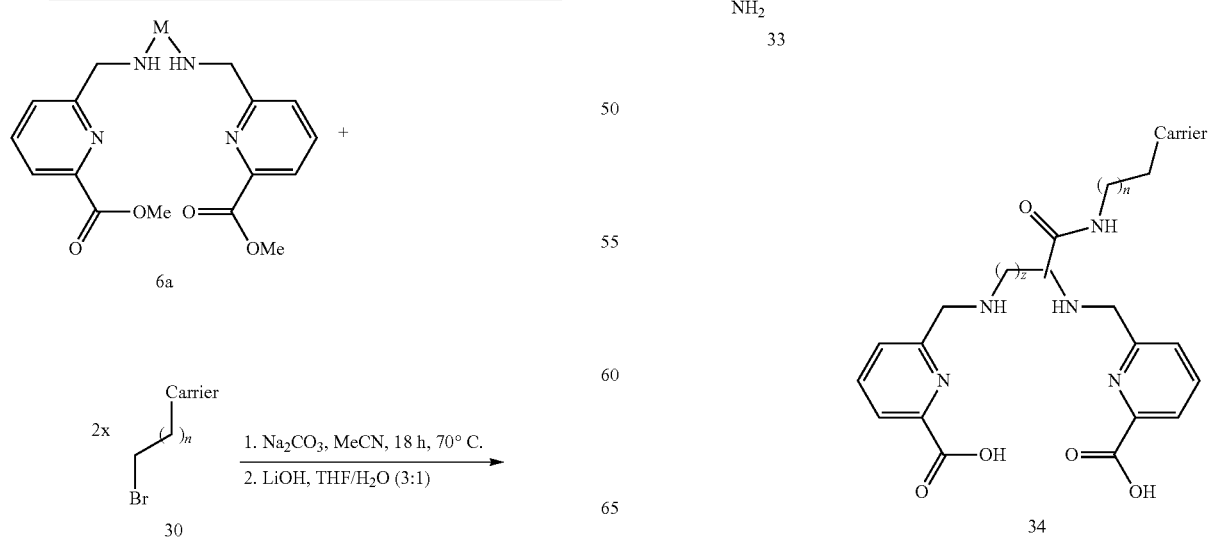

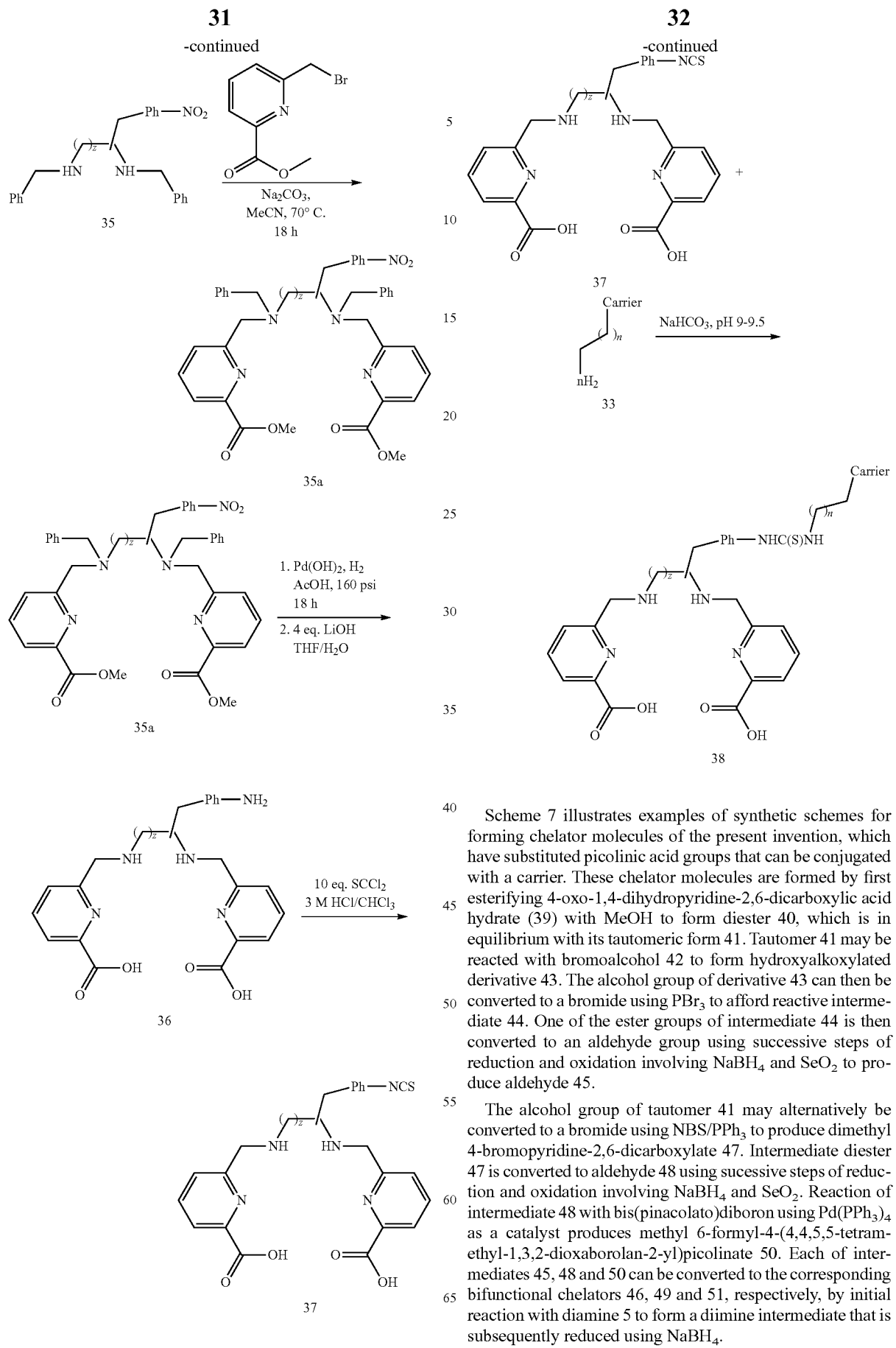

Scheme 7 illustrates examples of synthetic schemes for forming chelator molecules of the present invention, which have substituted picolinic acid groups that can be conjugated with a carrier. These chelator molecules are formed by first esterifying 4-oxo-1,4-dihydropyridine-2,6-dicarboxylic acid hydrate (39) with MeOH to form diester 40, which is in equilibrium with its tautomeric form 41. Tautomer 41 may be reacted with bromoalcohol 42 to form hydroxyalkoxylated derivative 43. The alcohol group of derivative 43 can then be converted to a bromide using $PBr_3$ to afford reactive intermediate 44. One of the ester groups of intermediate 44 is then converted to an aldehyde group using successive steps of reduction and oxidation involving $NaBH_4$ and $SeO_2$ to produce aldehyde 45.

The alcohol group of tautomer 41 may alternatively be converted to a bromide using $NBS/PPh_3$ to produce dimethyl 4-bromopyridine-2,6-dicarboxylate 47. Intermediate diester 47 is converted to aldehyde 48 using sucessive steps of reduction and oxidation involving $NaBH_4$ and $SeO_2$. Reaction of intermediate 48 with bis(pinacolato)diboron using $Pd(PPh_3)_4$ as a catalyst produces methyl 6-formyl-4-(4,4,5,5-tetramethyl-1,3,2-dioxaborolan-2-yl)picolinate 50. Each of intermediates 45, 48 and 50 can be converted to the corresponding bifunctional chelators 46, 49 and 51, respectively, by initial reaction with diamine 5 to form a diimine intermediate that is subsequently reduced using $NaBH_4$.

Scheme 7. Examples of synthetic schemes for forming chelators of the present invention, which include picolinic acid groups having pendant groups useful for conjugation with a carrier comprising a targeting group.
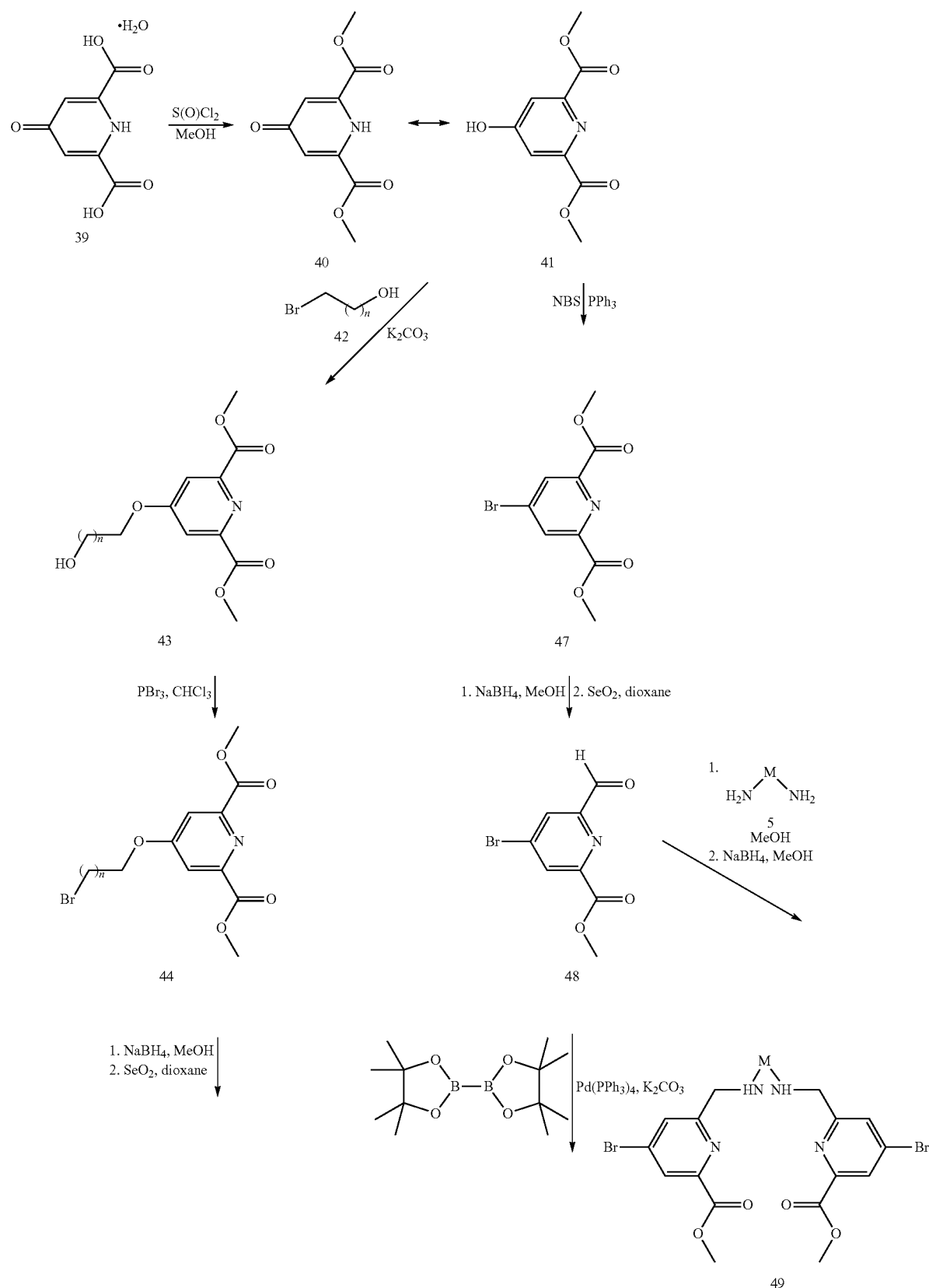

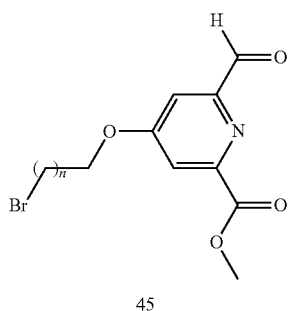

45

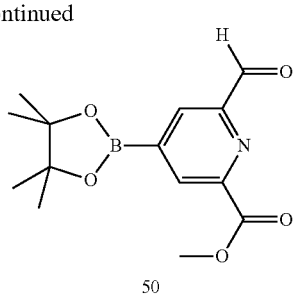

50

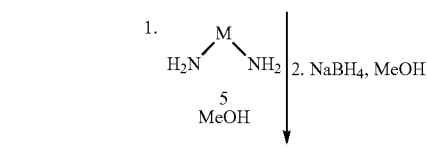

46

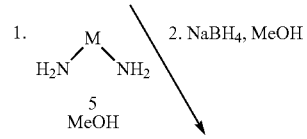

51

Scheme 8 illustrates the synthetic steps involved in conjugating the chelators shown in Scheme 7 to a carrier molecule. Chelator 46, which has a pendant alkyl bromide group, is directly coupled to a carrier having a free amino group by way of a nucleophilic displacement reaction. The resulting intermediate conjugate is deprotected under basic conditions to afford conjugate 52.

Chelator 51 having picolinyl moieties substituted with boronate ester moieties can be coupled to a carrier molecule having a pendant bromide group (53) using a Pd(PPh$_3$)$_4$ catalyst. The resulting intermediate conjugate is deprotected under basic conditions to produce conjugate 54.

Finally, conjugate 49, which has picolinyl moieties substituted with bromide groups, can be linked to a carrier having a free amino group under Buchwald-Hartwig reaction conditions. Deprotection of the intermediate conjugate under basic conditions affords conjugate 56.

Scheme 8. Examples of synthetic schemes for forming conjugates from bifunctional chelators having functionalized picolinic ester groups of the present invention

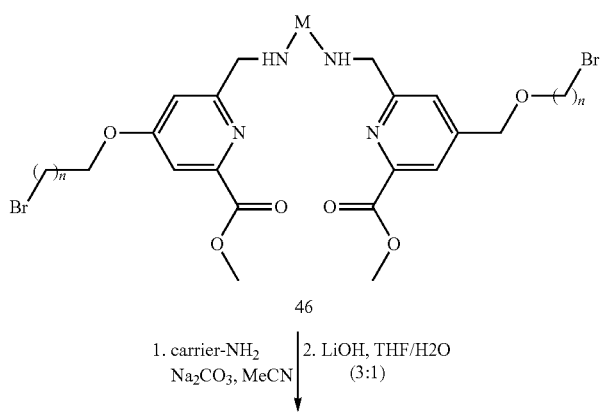

46

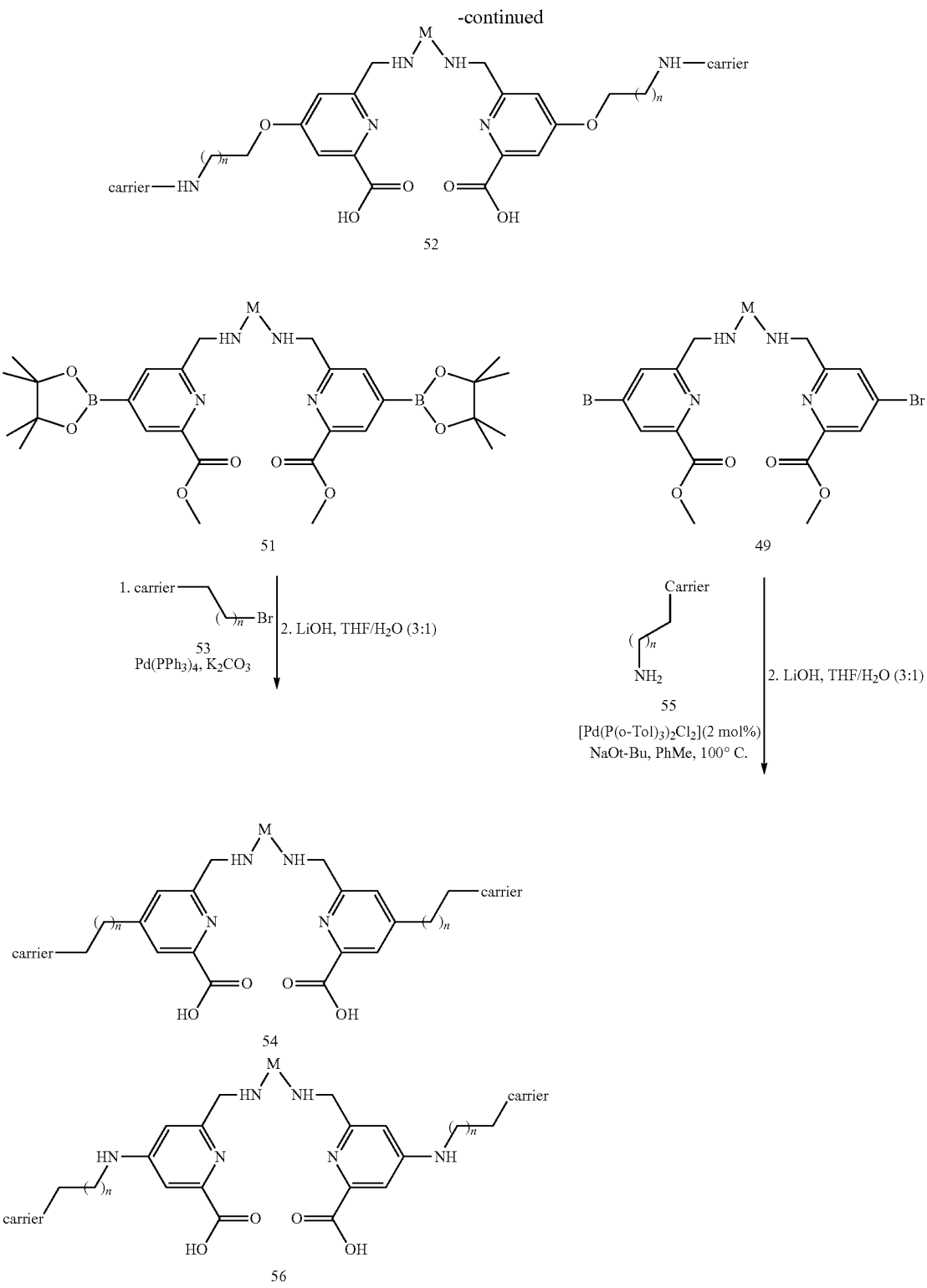

An example of a synthetic method for preparing a conjugated, di-, N-substituted bifunctional chelating agent of the present invention is illustrated in Scheme 9 and involves selectively alkylating di-, N-alkylated alkylene derivative (18d') with tert-butyl 6-(bromomethyl)picolinate (2) in the presence of K₂CO₃ to afford alkylated product (18d'). Hydrolysis of the ester substituents of the alkylene moiety of (18d') is then conducted using LiOH in THF/H₂O (THF=tetrahydrofuran) to afford the corresponding diacid product 57, which is then coupled with a biological carrier to form intermediate (58). Intermediate (58) is subsequently deprotected using TFA to produce conjugated bifunctional chelator (59).

Scheme 9. Example of synthetic scheme for forming conjugated, di-, N-derivatized bifunctional dedpa.

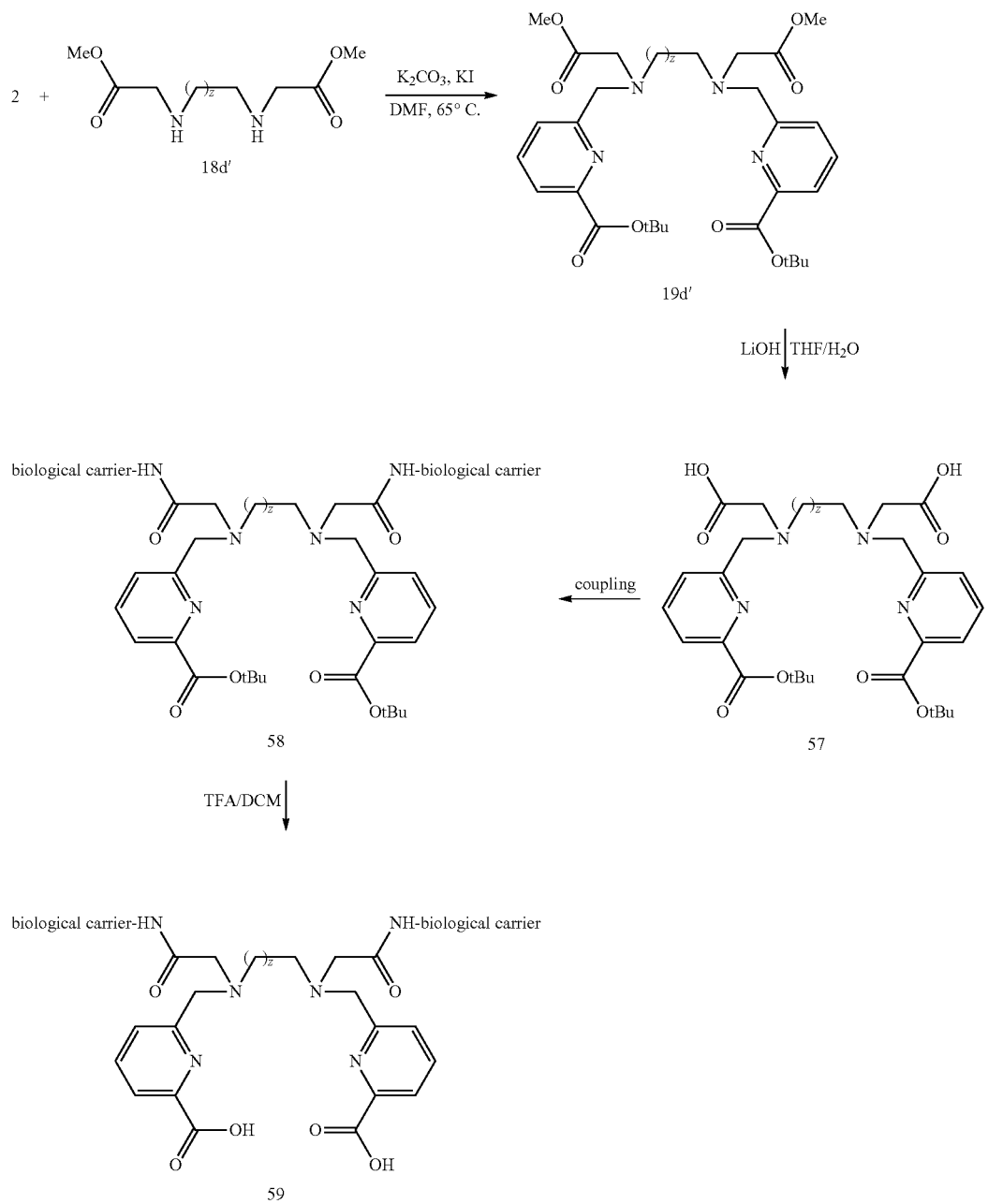

Scheme 10 illustrates an example of a method for forming a conjugated, backbone-substituted bifunctional chelator of the present invention. The synthetic method involves:

(i) Amidation of each of the primary amino groups of an alkylene diamine group substituted on its carbon backbone with p-nitrobenzyl group (18a') with t-butyl carbamate (BOC) protecting groups to afford diamide derivative 60. A specific example of 18a' is (1-(p-nitrobenzyl)ethylenediamine), which can be produced according to the procedure described in A. K. Mishra et al., New J. Chem., 2003, 1054-1058, the disclosure of which is incorporated by reference herein.

(ii) Alkylation of each secondary amino group of diamide 60 to produce the dialkylated product 60.

(iii) Palladium catalyzed reduction of the nitro group of 61 to produce benzylamine 62 (See Ali et al., 1996, Bioconjugate Chem., 7, 576-583, the disclosure of which is incorporated by reference herein.)

(iv) Coupling of benzylamine 62 with a free carboxylate group of a biological carrier to form a protected intermediate bioconjugate (See Nakajima et al., Bioconjugate Chem., 1995, 6, 123, the disclosure of which is incorporated by reference herein), and (v) Simultaneous deprotection of both acid-labile protection groups of the intermediate bioconjugate to form bifunctional chelator 63 (See Chandrasekaran et al., J. Org. Chem., 1977, 42, 3972, the disclosure of which is incorporated by reference herein.)

Scheme 10. Example of synthetic scheme for forming a backbone monofunctionalized bifunctional dedpa

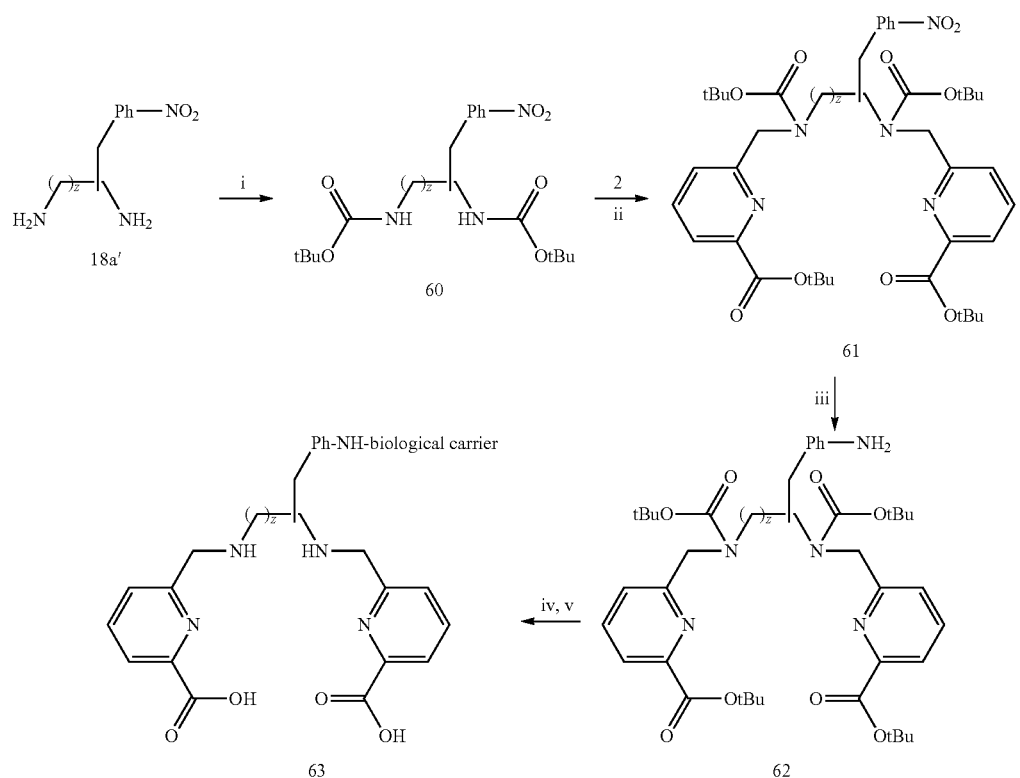

Although the synthetic schemes described above relate to the production of racemic ligands or chelators, it is to be understood that these schemes can be easily modified to produce enantiomerically pure or enantiomerically enriched ligands having the (L) or (D)-configuration by using enantiomerically pure or enantiomerically enriched starting materials, or by including one or more resolution steps within these schemes, which are generally known in the art.

As used herein, the terms "degree of complexation" and "percent complexation" are used interchangeably and are defined to mean the percentage of the ion that is successfully complexed with the bifunctional chelant. Here percent complexation is expressed as radiochemical yield, which is the yield of radiolabeled complex expressed as a fraction of the radioactivity originally present. The value of radiochemical yield obtained when making the ion complexes of the present reaction can be greater than 90% or greater than 95%, as measured by reverse phase chromatography (HPLC).

The conjugates of the present invention can be prepared by first forming the complex and then attaching to the biological carrier. Thus, the process involves preparing or obtaining the ligand, forming the complex with an ion and then adding the biological carrier. Alternatively, the process may involve first conjugation of the ligand to the biological carrier and then the formation of the complex with an ion. Any suitable process that results in the formation of the ion-conjugates of this invention is within the scope of the present invention.

The complexes, bifunctional chelates and conjugates of the present invention are useful as diagnostic agents in the manner described. These formulations may be in kit form such that the two components (i.e., ligand and metal, complex and antibody, or ligand/antibody and metal) are mixed at the appropriate time prior to use. Whether premixed or as a kit, the formulations usually require a pharmaceutically acceptable carrier.

Tissue specificity may also be realized by ionic or covalent attachment of the chelate of formula (I) (where $R^6$ is $NH_2$, isothiocyanato, semicarbazido, thiosemicarbazido, maleimido, bromoacetamido or carboxyl group) to a naturally occurring or synthetic molecule having specificity for a desired target tissue. One possible application of this approach is through the use of chelate conjugated monoclonal antibodies which would transport the chelate to diseased tissue enabling visualization. The surgeon could then illuminate soft tissue with a UV light source coupled with an appropriate detector, if necessary, and surgically remove the indicated tissue.

The use and the synthesis of $H_2$dedpa (originally named $H_2$bpce) have been previously reported with divalent metals showing reasonable chelation properties.[26] Under mild reaction conditions (room temperature, aqueous buffer, pH 4), $H_2$dedpa coordinated $^{67}$Ga (a longer-lived Ga isotope that can serve as a model for $^{68}$Ga) quantitatively within 10 minutes (as does NOTA[27]). DOTA however, requires heating for quantitative reaction yields.[28] Concentration dependent coordination of $H_2$dedpa at concentrations as low as $10^{-7}$M to both $^{68}$Ga and $^{67}$Ga showed quantitative conversion to the desired product. When coordinating to $^{68}$Ga, high specific activities (as high as 9.8±0.1 mCi nmol$^{-1}$) were obtainable in 99% radiochemical yield without any purification steps. This is the highest specific activity measured for any chelator with $^{68}$Ga, when neither heating nor $^{68}$Ga pre-purification are used.[29]

Figure 9:
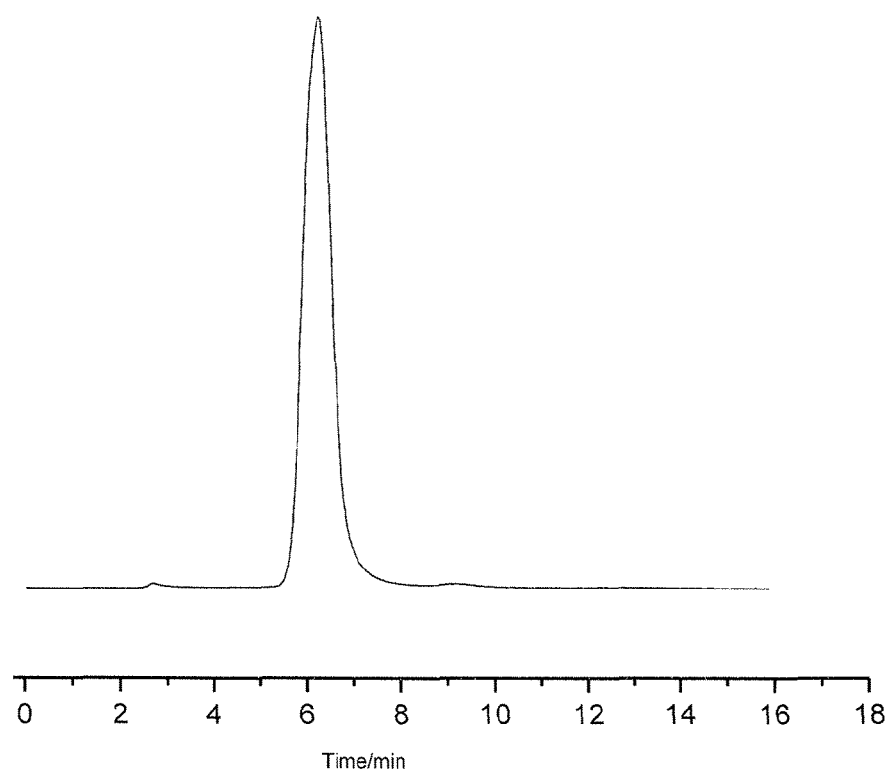
FIG. 9 illustrates the labelling trace of $^{67}$Ga(dedpa)$^+$ on HPLC.
Figure 12:
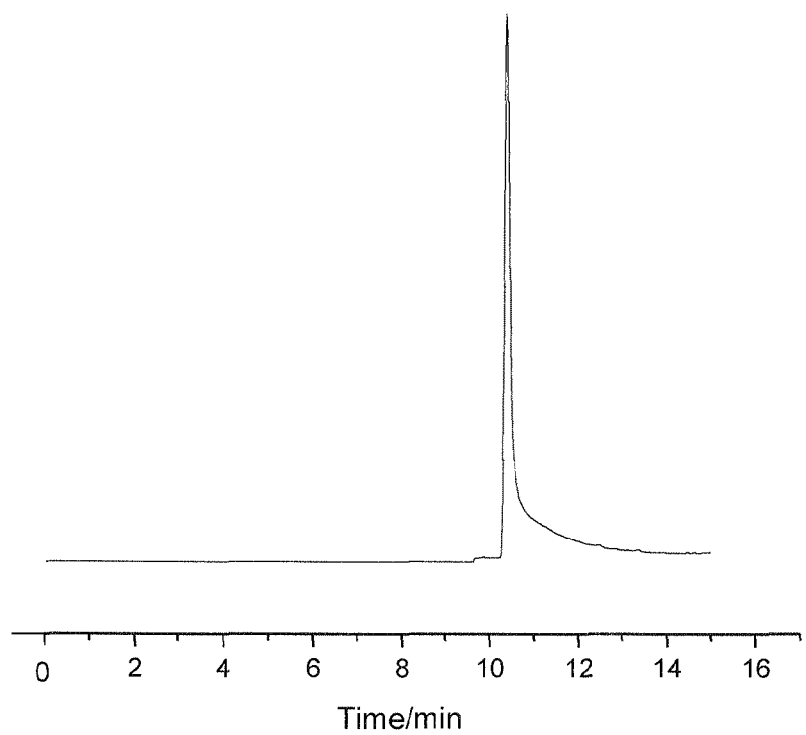
FIG. 12 illustrates the HPLC chromatogram for $^{67}$Ga-transferrin.
Figure 13:
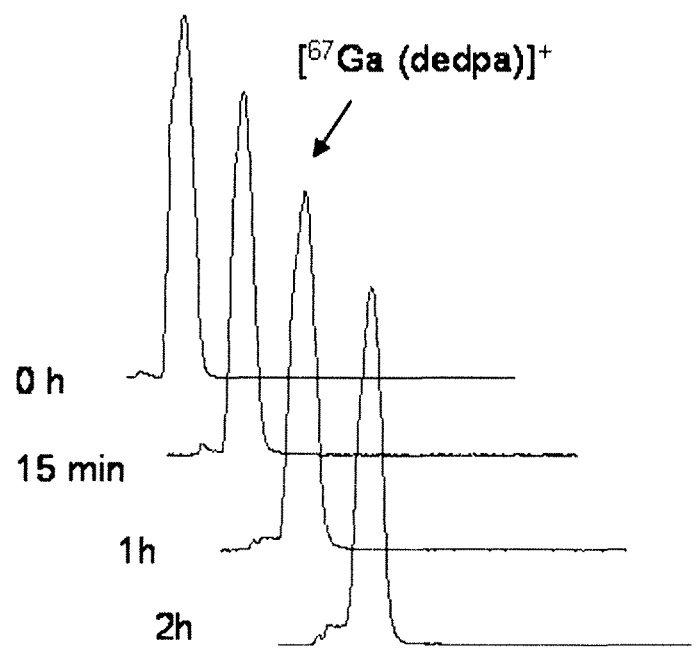
FIG. 13 illustrates stacked labelling traces of $^{67}$Ga(dedpa)$^+$ of 2-h stability experiment against apo-transferrin.
Figure 14:
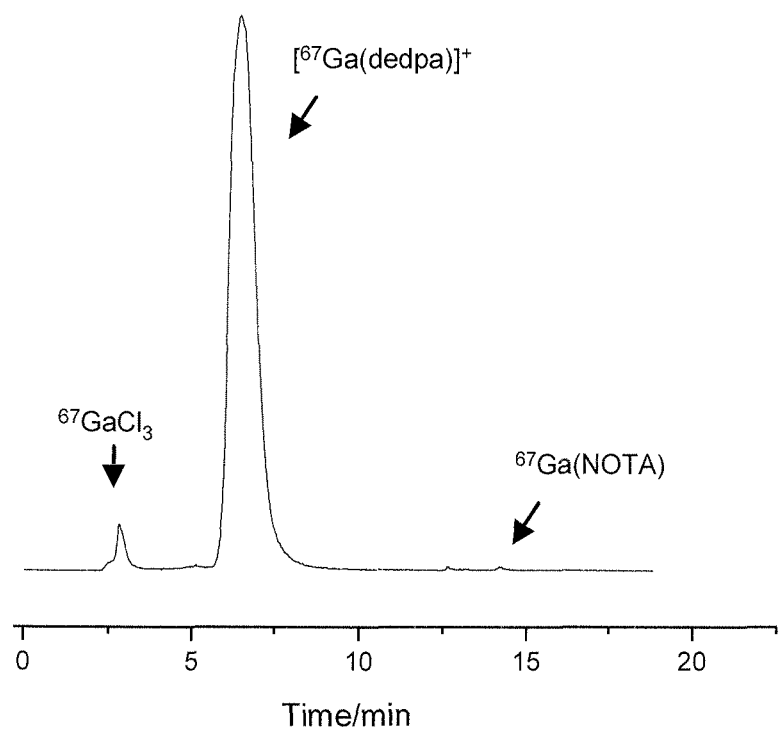
FIG. 14 illustrates the labelling trace of competition between H$_2$dedpa and NOTA for coordination of $^{67}$Ga. on HPLC.

To investigate the stability of the $^{67}$Ga radiochemical complex, a 2 hour competition experiment was conducted in the presence of excess human apo-transferrin; the iron sequestering/transport protein that has very high affinity for Ga(III) (FIG. 1).[30] The $^{67}$Ga(dedpa)$^+$ complex was fully intact after 2 h, suggesting that it should have very high in vivo stability, similar to that reported for $^{68}$Ga NOTA complexes.[31] In a direct competition for chelation of $^{67}$Ga with equal concentrations of both NOTA and H$_2$dedpa, over 96% was coordinated by (dedpa)$^{2-}$, less than 1% by NOTA, demonstrating the expected faster Ga complexation with the acyclic H$_2$dedpa than with macrocyclic NOTA. FIG. 9 illustrates the labelling trace of $^{67}$Ga(dedpa)$^+$ on HPLC. ($t_R$: 6.1 minutes (gradient: A: NaOAc buffer, pH 4.5, B: CH$_3$OH. 0-5% B linear gradient 20 min). Yield: 99%) FIG. 12 illustrates the HPLC chromatogram for $^{67}$Ga-transferrin (gradient: A: NaOAc buffer, pH 4.5, B: CH$_3$OH. 0-100% B linear gradient 20 min); reference for stability measurements of $^{67}$Ga(dedpa)$^+$. FIG. 13 illustrates stacked labelling traces of $^{67}$Ga (dedpa)$^+$ of 2 h stability experiment against apo-transferrin (gradient: A: NaOAc buffer, pH 4.5, B: MeOH. 0-100% B linear gradient 20 min). FIG. 14 illustrates the labelling trace of competition between H$_2$dedpa and NOTA for coordination of $^{67}$Ga on HPLC. (gradient: A: NaOAc buffer, pH 4.5, B: CH$_3$CN. 0-5% B gradient 7 min, 0-100% B gradient 20 min; yield for $^{67}$Ga(dedpa)$^+$: 96%. Yield for $^{67}$Ga-NOTA): <1%).

Solution thermodynamic investigations of the corresponding cold complex Ga(dedpa)$^+$ have provided a complex stability constant of log $K_{ML}$=28.11(8), obtained by ligand-ligand competition with EDTA using potentiometric titration. A more relevant indicator of the extent to which a metal complex is formed in solution is given by pM (−log free M) which considers the influence of ligand basicity and chelate hydrolysis. The values of log $K_{ML}$ and pM of the Ga(III) complexes of dedpa$^{2-}$ and other relevant multidentate ligands are shown in Table 1. The high values of log $K_{ML}$ and pM for Ga(dedpa)$^+$ confirms the high affinity of dedpa$^{2-}$ for Ga(III) as well as high thermodynamic stability.

TABLE 1

Formation constants (log $K_{ML}$) and pM$^a$ of Ga(III) complexes.

| Ligand | log $K_{ML}$ | pM |
|---|---|---|
| dedpa$^{2-}$ | 28.11(8) | 27.4 |
| EDTA[32] | 21.7 | 18.3 |
| DOTA[33] | 21.33 | 18.5 |
| NOTA[34] | 30.98 | 27.9 |
| Transferrin$^b$ | 20.3 | 21.3 |

$^a$Calculated for 10 μM total ligand and 1 μM total metal at pH 7.4 and 25° C.
$^b$Conditional constant for log $K_{ML}$ from Ref 16.

Figure 2:
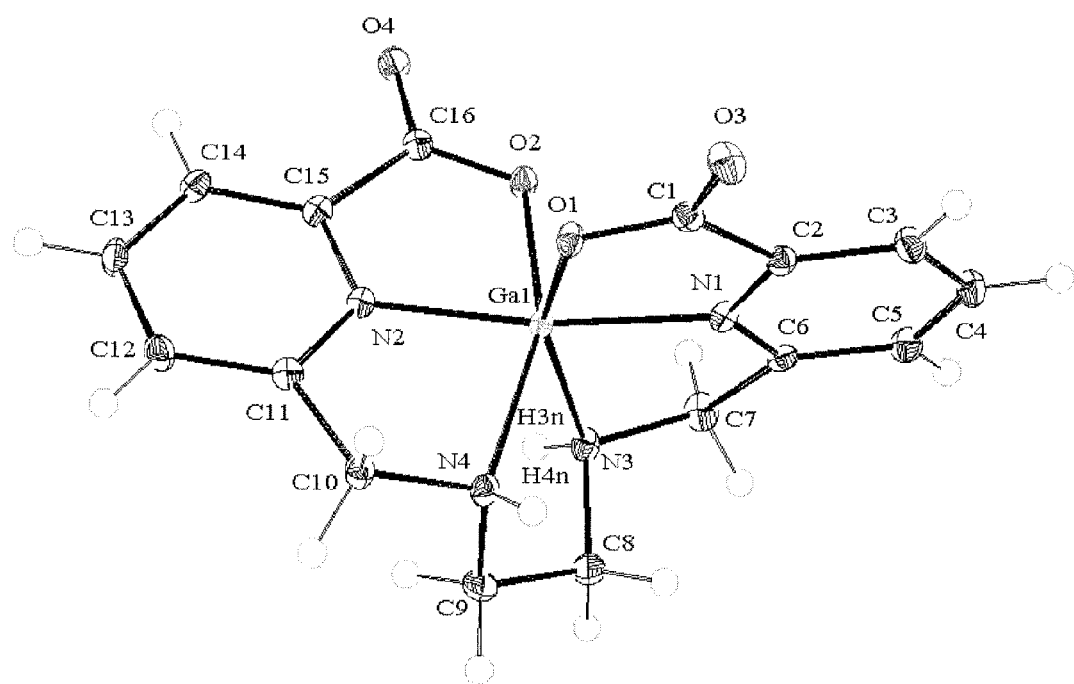
FIG. 2 illustrates solid-state structure of the cation in Ga(dedpa)ClO$_4$.

The solid state X-ray crystal structure (FIG. 2) provides significant insight into the coordination environment of Ga(dedpa)$^+$. In comparison with the crystallized Ga complexes of NOTA[35] and DOTA[36] which have widely dispersed metal-to-ligand bond distances, Ga(dedpa)$^+$ has a more equally distributed array of bond lengths, suggesting that the unusually high stability of the complex is due to a near-perfect fit with the Ga$^{3+}$ ion.

Another characteristic that clearly differentiates Ga(dedpa)$^+$ from complexes with the macrocyclic chelators is the C$_2$ rotational axis, which has also been confirmed in solution through $^{13}$C NMR spectroscopy.

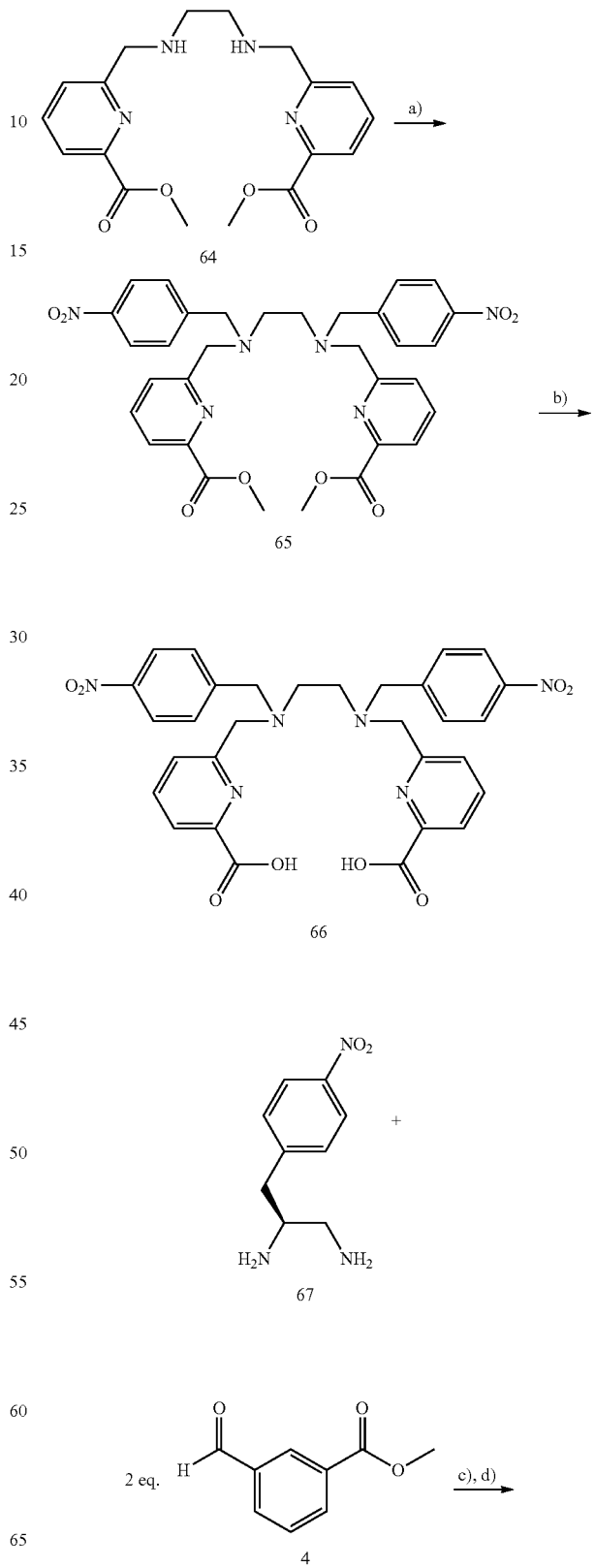

Scheme 11. Syntheses of compounds 66 and 69: a) 4-nitrobenzyl bromine, Na$_2$CO$_3$, CH$_3$CN, 18 h; b)LiOH, THF/water (3:1), 45 min; c) CH$_3$OH, reflux, 2h; d) NaBH$_4$, 0° C., 2h; e) LiOH, THF/water (3:1), 30 min.

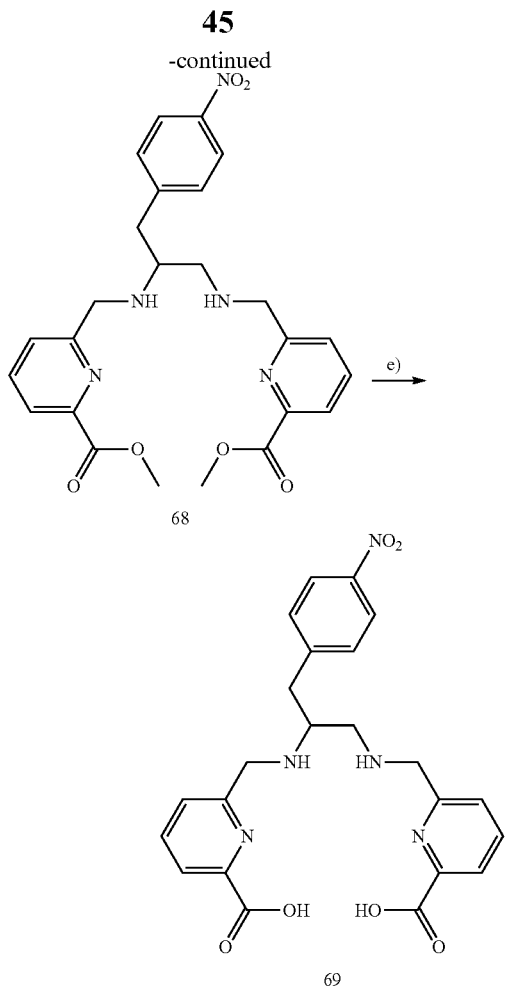

68

69

To investigate different modes of functionalization analogous to the bifunctional versions of the macrocyclic chelators, two model compounds 66 and 69 have been synthesized (Scheme 4). Compound 66 displays derivatization through the two aliphatic nitrogens, affording a scaffold capable of carrying two targeting molecules, while compound 69 is derivatized through the backbone of the ethylenediamine (en) component of the basic ligand structure, retaining the original coordination environment more closely, but only capable of carrying one targeting molecule. Both 66 and 69 incorporate the nitrobenzyl functionality which can be converted easily into the corresponding amino- or isothiocyanato-benzyl, coupling moieties frequently employed for conjugation to target molecules via a free carboxylate or primary amine, respectively.[37,38]

Figure 15:
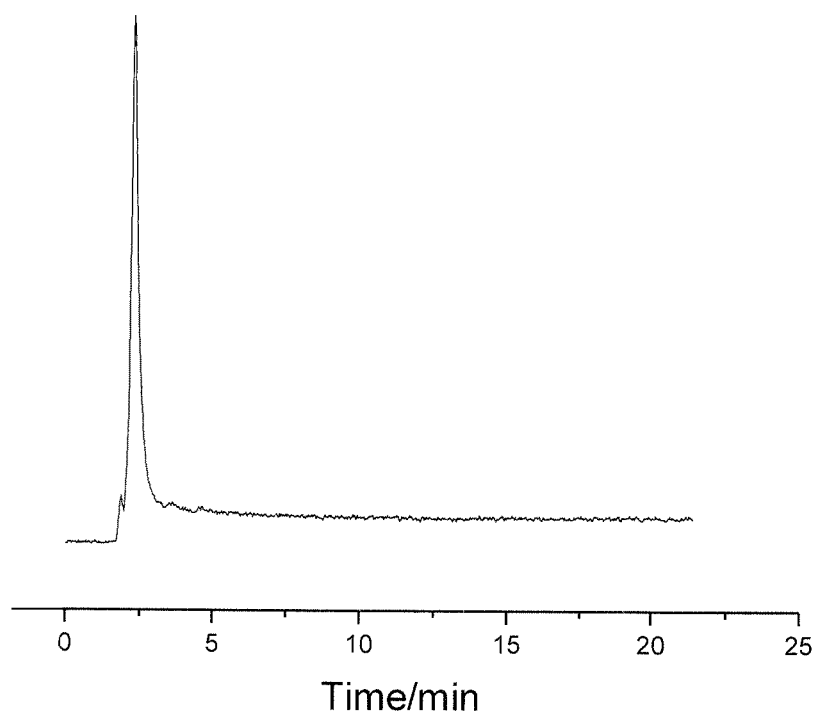
FIG. 15 illustrates the HPLC chromatogram for $^{67}$Ga-transferrin (gradient: A: NaOAc buffer, pH 4.5, B: CH$_3$CN. 0-100% B linear gradient 20 min; reference for stability measurements of $^{67}$Ga(66)$^+$ and $^{67}$Ga(69)$^+$).
Figure 16:
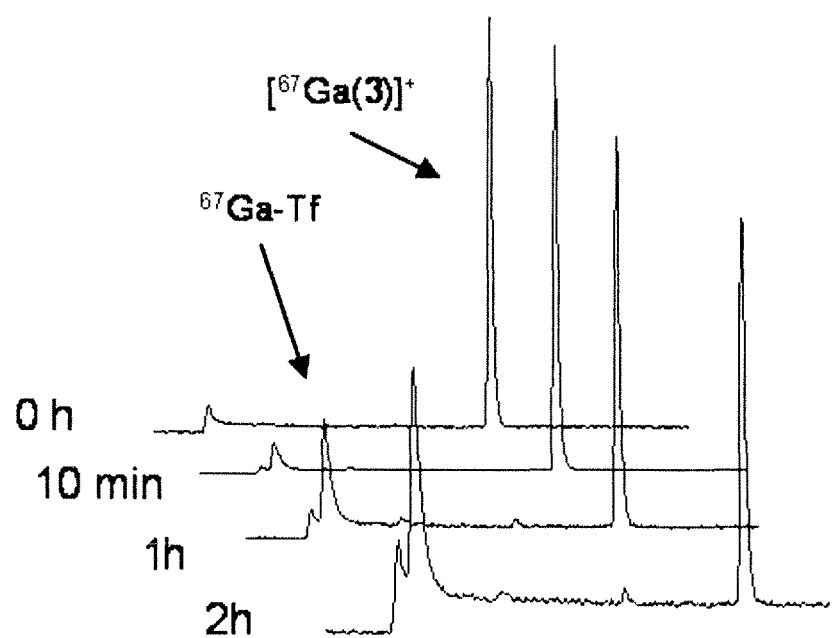
FIG. 16 illustrates stacked labelling traces of $^{67}$Ga(66)$^+$ of 2-h stability experiment against apotransferrin (gradient: A: NaOAc buffer, pH 4.5, B: CH$_3$CN. 0-100% B linear gradient 20 min).
Figure 17:
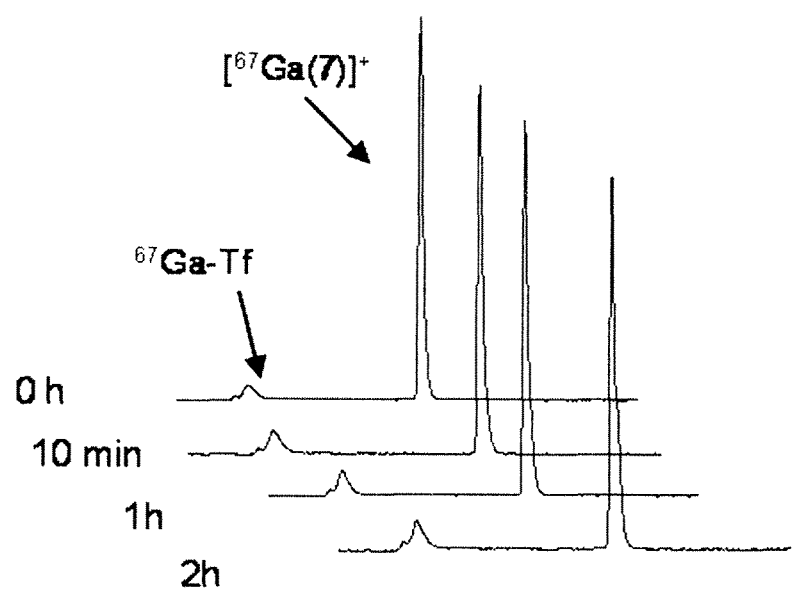
FIG. 17. illustrates stacked labelling traces of $^{67}$Ga(69)$^+$ of 2-h stability experiment against apotransferrin (gradient: A: NaOAc buffer, pH 4.5, B: CH$_3$CN. 0-100% B linear gradient 20 min).
Figure 18A:
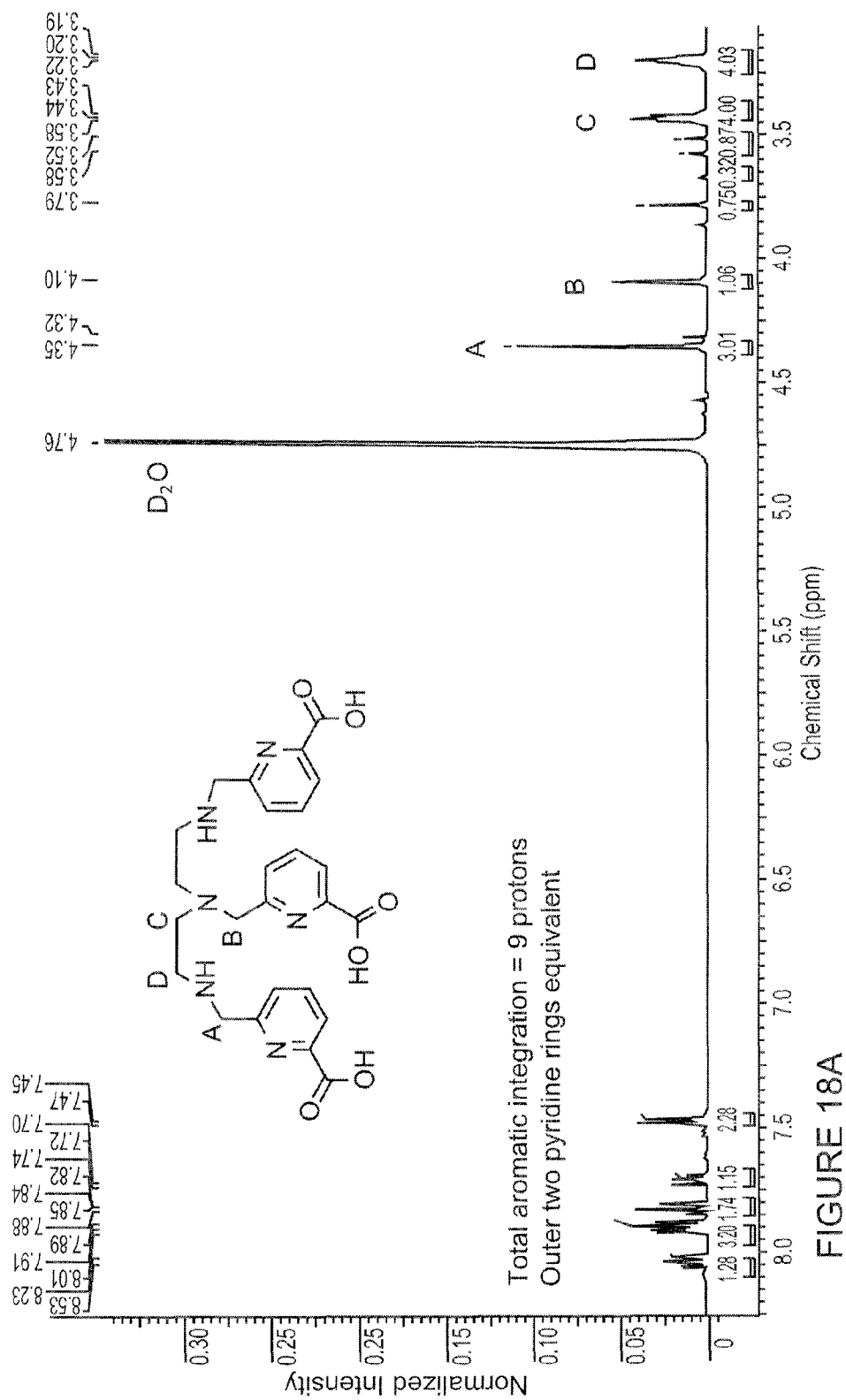
FIG. 18A and FIG. 18B illustrate $^1$H-NMR and $^{13}$C-NMR spectra of compound 104 in D$_2$O.
Figure 18B:
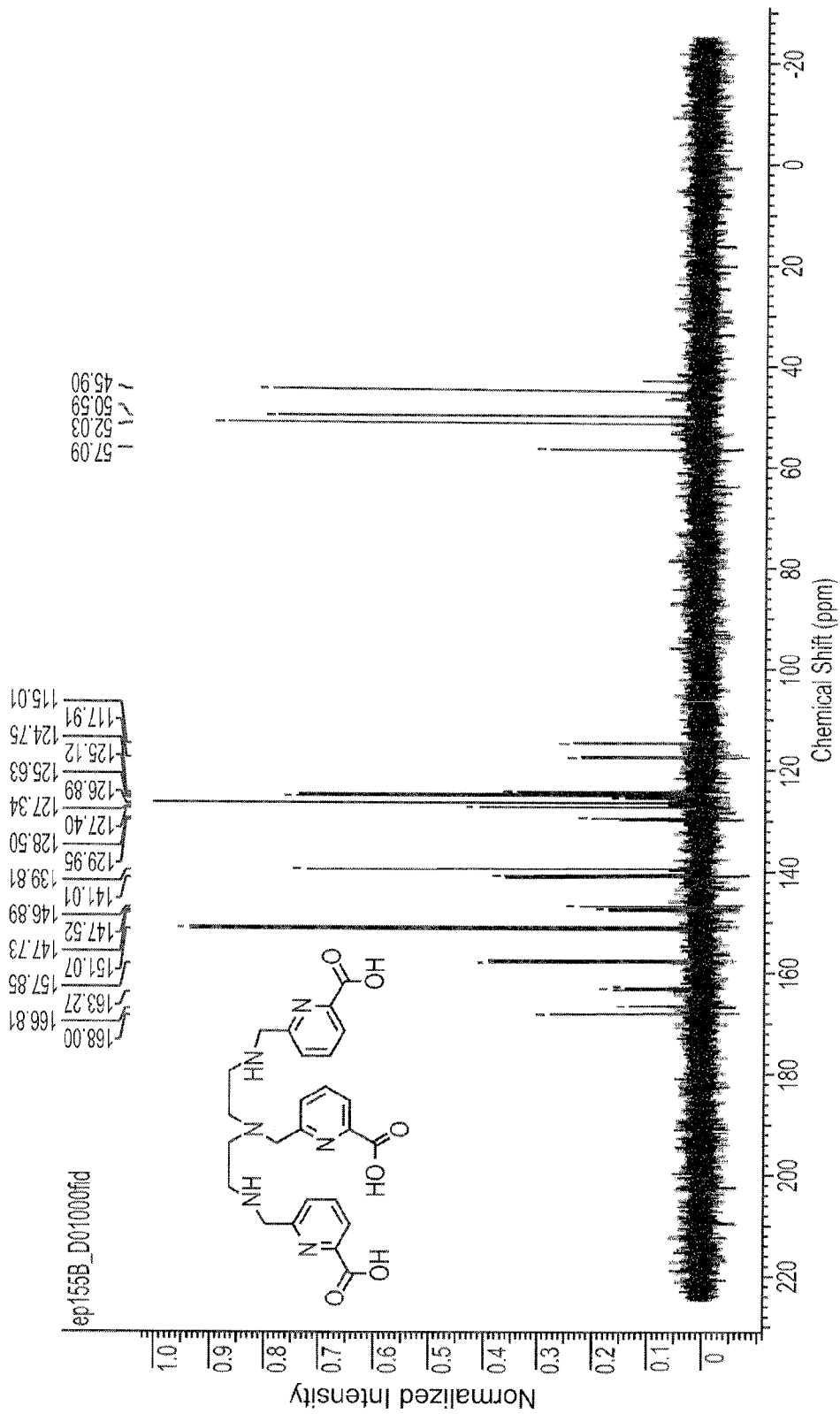
Figure 19A:
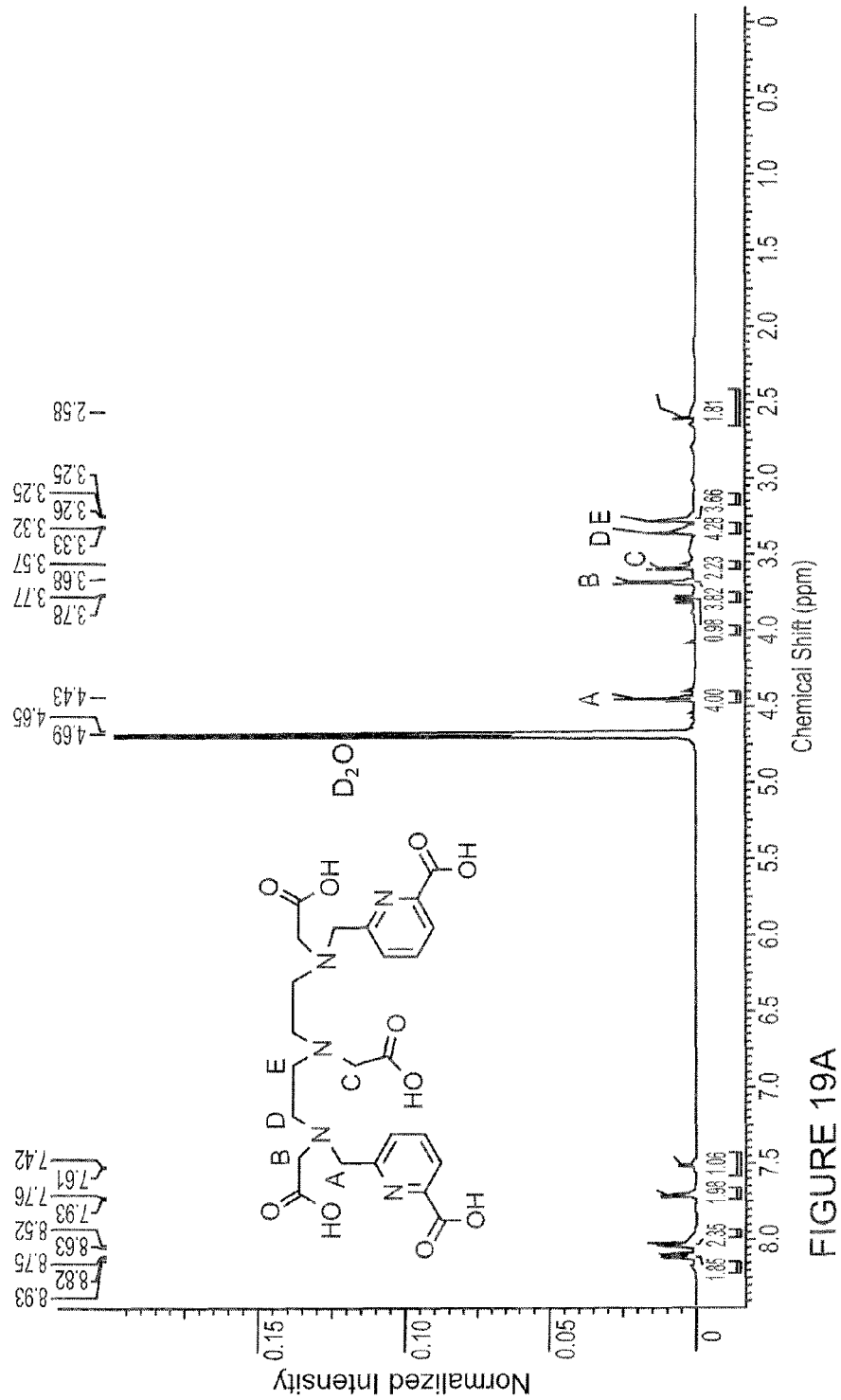
FIG. 19A and FIG. 19B illustrate $^1$H-NMR and $^{13}$C-NMR spectra of compound 108 in D$_2$O.
Figure 19B:
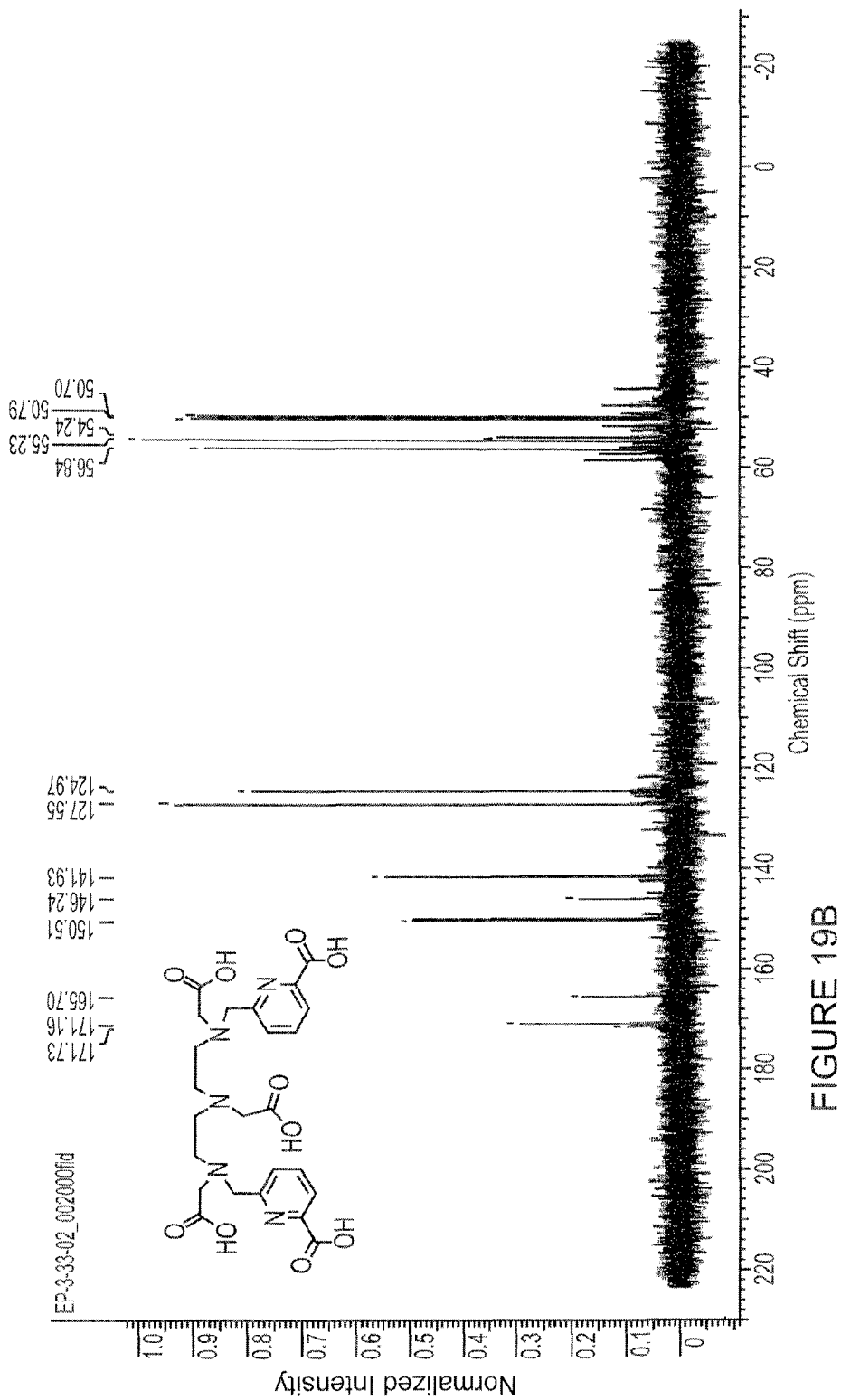

Compound 66 was synthesized from 1,2-{6-(methoxycarbonyl)pyridin-2-yl}methylaminoethane,[39] which is then subsequently alkylated with 4-nitrobenzyl bromide. Intermediate 65 is purified and the carboxylates are deprotected under standard conditions to afford the clean product 66 as a white solid. The complex with cold (non-radioactive) gallium(III) is formed within 2 h at pH 4-5 under gentle heating and again the $C_2$ rotational axis was confirmed in both the solid-state structure and the solution NMR spectrum (see FIGS. 6-8). Coordination to $^{67}$Ga or $^{68}$Ga forms the complex within 10 minutes at room temperature in 98% radiochemical yield. A subsequent apo-transferrin challenge experiment revealed 51% of the radiolabeled complex remained intact after 2 h in the presence of excess apo-transferrin; a stability inferior to that of Ga(dedpa)$^+$, but comparable to that of Ga-DOTA.[31] Concentration-dependent coordination to $^{68}$Ga showed that 66 is capable of coordinating under standard, mild conditions at concentrations as low as $10^{-6}$ M (Table 2). FIG. 15 illustrates the HPLC chromatogram for $^{67}$Ga-transferrin (reference for stability measurements of $^{67}$Ga(66)$^+$ and $^{67}$Ga(69)$^-$), and FIGS. 16-17 illustrate stacked labelling traces of $^{67}$Ga(66)$^+$ and $^{67}$Ga(69)$^+$ of 2 h stability experiment against apo-transferrin (gradient: A: NaOAc buffer, pH 4.5, B: CH$_3$CN. 0-100% B linear gradient 20 min).

TABLE 2

Stability of investigated chelators at various times in the 2-h competition experiment in the presence of excess human apo-transferrin.

| Ligand | 10 min | 1 h | 2 h |
|---|---|---|---|
| H$_2$dedpa | >99% | >99% | >99% |
| 66 | 88% | 69% | 51% |
| 69 | 98% | 97% | 97% |

Compound 69 was furnished through a different route; 67 was derived from 4-nitro-L-phenylalanine,[40] while 4 was afforded through a four step synthesis from 2,6-pyridinedicarboxylic acid.[39] A one-pot reductive amination process produces 68 in moderate yields along with a mixture of impurities, which can be separated from the product through column chromatography. A subsequent deprotection leads to 69 as a light orange solid. The complex with cold gallium(III) is formed within 2 h at pH 4-5 under gentle heating, while the $^{67}$Ga and $^{68}$Ga complexes are formed within 10 minutes at room temperature in 97% radiochemical yield. The subsequent apo-transferrin challenge experiment reveals a stability comparable to that of Ga(dedpa)$^+$, with over 97% of the complex remaining intact after 2 h. Concentration-dependent coordination to $^{68}$Ga showed that 69 is capable of coordinating under standard, mild conditions at concentrations as low as $10^{-6}$ M much like 66.

A biodistribution study conducted in mice (FIG. 4, Tables 2-4) indicated that $^{67}$Ga(dedpa)$^+$ cleared from the background tissue, such as muscle, within the first 30 min and was excreted mainly through the kidneys. The in vivo stability of $^{67}$Ga(dedpa)$^+$ was supported by the low uptake in bone, which is known to be a site of increasing accumulation for weakly chelated $^{67}$Ga.[41] The overall biodistribution profile compares well to macrocyclic chelators evaluated in a similar study, also exhibiting the low uptake in liver and intestines characteristic of ionic compounds. The persistent high uptake in the blood serum was not confirmed with the derivatized compounds, suggesting that added functionality influences biodistribution. Serum stability studies done in vitro confirmed that $^{67}$Ga(dedpa)$^+$ was stable to transchelation by serum proteins.

Figure 5:
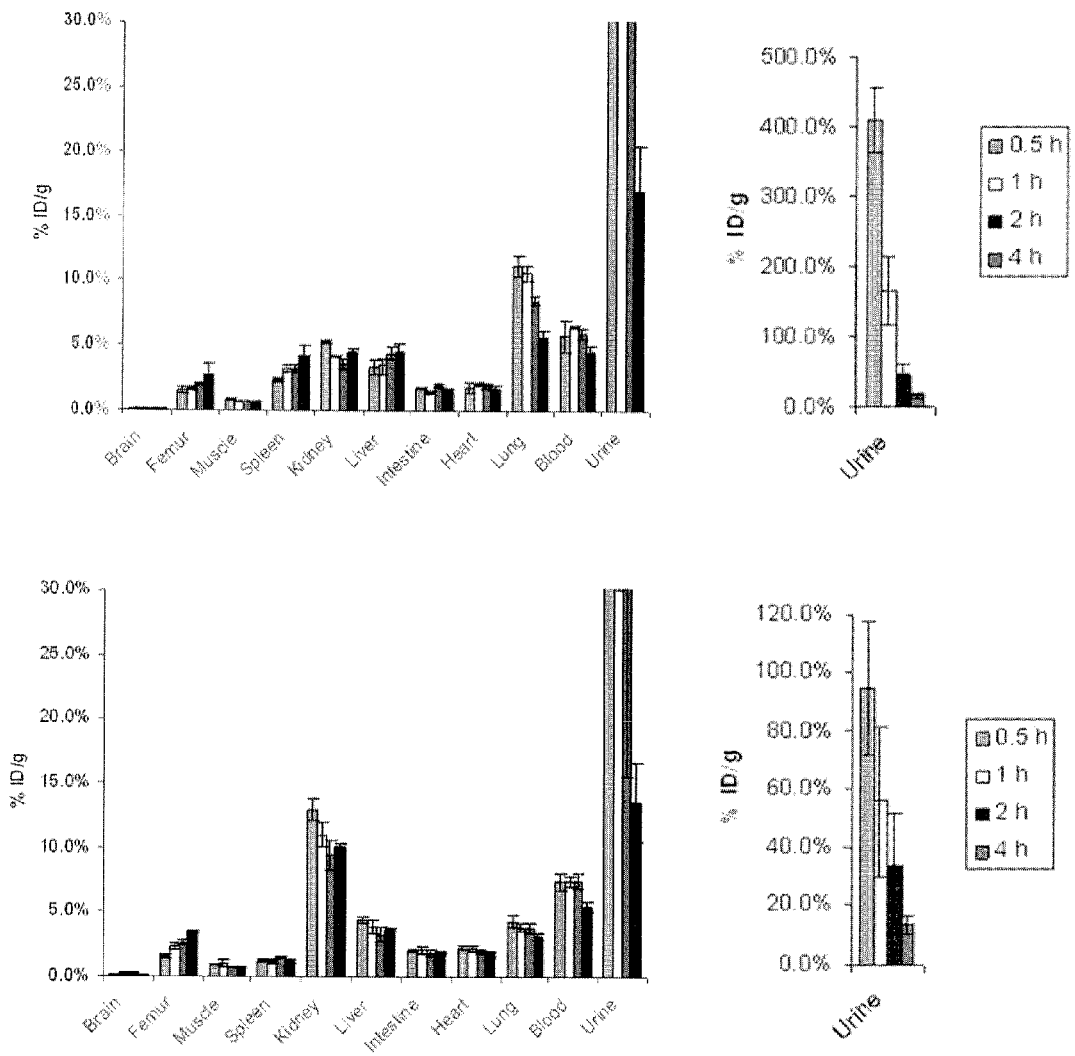
FIG. 5 illustrates biodistribution of $^{67}$Ga(66)$^+$ (upper) and $^{67}$Ga(69)$^+$ (lower) in female ICR mice over 4 h; complete data for urine is shown also in separate diagrams to the right.

In biodistribution studies conducted for $^{67}$Ga(66)$^+$ and $^{67}$Ga(69)$^+$, whole blood was collected instead of serum, and urine was collected as an additional data point (FIG. 5). Both $^{67}$Ga(66)$^+$ and $^{67}$Ga(69)$^-$ exhibited improved clearance from all organs, low bone uptake (indicator for complex stability) and excretion through urine. Despite lower in vitro stability, the biodistribution of $^{67}$Ga(66)$^+$ suggests high stability in vivo and shows better clearance from blood and kidneys than both $^{67}$Ga(69)$^+$ and $^{67}$Ga(dedpa)$^+$. It is possible that compounds containing secondary amines associate stronger with blood serum proteins and kidney tissue; however, the difference in biodistribution of even $^{67}$Ga(69)$^+$ and $^{67}$Ga(dedpa)$^+$ shows that added functionalities, such as peptides or other targeting vectors, have a great impact on the interaction of these compounds with in vivo systems.

$H_2$dedpa complexes quickly with Ga, and forms complexes of very high stability, comparing well to the widely used macrocyclic chelator NOTA and exceeding the properties of DOTA. $H_2$dedpa and its derivatives can be coordinated to Ga isotopes under mild room temperature conditions at high specific activities in short reaction times, making it an ideal scaffold for further elaboration and applications such as peptide labeling. The high radiochemical yield and high specific activity of the products could obviate the need for time consuming HPLC purification, a major advantage for the short lived isotope $^{68}$Ga. In addition, the biodistributions of $^{67}$Ga(dedpa)$^+$, $^{67}$Ga(66)$^+$ and $^{67}$Ga(69)$^+$ confirm the stability of the complexes measured in vitro with general clearance rendering these frameworks a good basis for elaboration of new Ga bioconjugates.

It is important to note that many of the advantageous properties described have been observed previously with only one macrocyclic chelate (NOTA), while they are unexpected for an acyclic system.

Challenge experiments described in Example 4 demonstrate that the chelate dedpa is capable of extracting gallium from a complex of gallium with 1,4,7-triazacyclononane-1, 4,7-triacetic acid (NOTA), a surprising result since it is commonly accepted that the NOTA complex of gallium is inert to displacement of gallium from the complex by other chelates, e.g., transferrin, a naturally occurring chelate that forms extremely strong complexes with both iron and gallium.

In fact, an even more unexpected result was obtained from a challenge experiment in which the chelate dedpa was capable of extracting gallium from transferrin (Example 3).

Complexes of dedpa with $^{68}$Ga and $^{67}$Ga can be obtained cleanly at a high radiolabeling yield (above 97%) within 10 minutes at room temperature. Furthermore, concentration-dependent labeling has shown that complexes of dedpa with the ligand $^{68}$Ga or $^{67}$Ga can be formed at a ligand concentration of $10^{-7}$ M. A specific radioactivity of up to 9.8 mCi/nmol can be achieved when preparing a complex of dedpa with $^{68}$Ga with a radiolabeling yield of above 97%.

The following examples are provided to further illustrate the present invention, and should not be construed as limiting thereof.

General
Materials and Methods

All solvents and reagents were from commercial sources and were used as received unless otherwise indicated. Human serum apo-transferrin was purchased from Sigma-Aldrich (St. Louis, Mo.). The analytical thin-layer chromatography (TLC) plates were aluminum-backed ultrapure silica gel 60, 250 μm; the flash column silica gel (standard grade, 60 Å, 32-63 mm) was provided by Silicycle. $^1$H and $^{13}$C NMR spectra were recorded at RT on Bruker AV300, AV400 or AV600 instruments; the NMR spectra are expressed on the δ scale and were referenced to residual solvent peaks or internal tetramethylsilane. Electrospray-ionization mass spectrometry (ESI-MS) spectra were recorded on a Micromass LCT instrument at the Department of Chemistry, University of British Columbia. IR spectra were collected neat in the solid state on a Thermo Nicolet 6700 FT-IR spectrometer. HPLC analysis or purification of non-radioactive compounds was done on a Phenomenex Synergi 4 mm Hydro-RP 80 A column (250×4.6 mm) in a Waters WE 600 HPLC system equipped with a 2478 dual wavelength absorbance UV detector run controlled by Empower software package. The HPLC system used for analysis of the radiochemical complexes consists of a Waters Alliance HT 2795 separation module equipped with a Raytest Gabbistar NaI detector and a Waters 996 photodiode array (PDA) detector. $^{67}$Ga was obtained as a 0.1 M HCl solution, and $^{68}$Ga (5-10 mCi/mL) (both MDS Nordion Inc.) was obtained from a generator constructed of titanium dioxide sorbent that was charged with $^{68}$Ge and eluted with aqueous HCl (0.1M).[42] The generator has been previously used for radiolabeling NOTA- and DOTA-based chelate systems and the resulting radiochemical yields and specific activities achievable for these chelates using this generator have been reported.[31] Analysis of radiolabelled complexes was done on a Phenomenex Hydrosynergy RP C18 4.6×150 mm analytical column (Ga(dedpa)$^+$), Phenomenex Jupiter 5μ C18 300 A 4.6×100 mm (transferrin challenge with Ga(dedpa)$^+$, NOTA versus $H_2$dedpa challenge, $H_2$dedpa challenge of Ga(NOTA), retention time of $^{67}$Ga-Tf: 10.7 min) and Waters XBridge BEH130 4.6>150 mm (Ga66$^+$, Ga69$^-$, as well as the transferrin challenges thereof, retention time of $^{67}$Ga-Tf: 2.5 min). If not mentioned otherwise, the $R_f$ values are measured on standard TLC plates with 10% MeOH in dichloromethane (DCM) as the mobile phase.

General Procedures and Common Starting Materials:

Common starting material such as the protected precursor 1,2-{6-(methoxycarbonyl)pyridin-2-yl}methylaminoethane to $H_2$dedpa 2HCl was synthesized according to the literature.[43] 6-Bromomethylpyridin-2-carboxylic acid methyl ester was synthesized according to the literature,[44] as well as precursors 91 and 97.[45]

The synthesis of Biotin-TFP and its precursor have been reported.[46]

General procedure for alkylation (i): Both secondary amine and 2.1 equivalents of the bromoalkyl were dissolved in acetonitrile. Twenty equivalents of $Na_2CO_3$ were added into the reaction mixture and the reaction was stirred at room temperature over night. The resulting milky solution was filtered and the solvent was removed in vacuo to afford the crude product as an oil. This was then subsequently purified by column chromatography (10% MeOH in DCM) to afford the product as a very viscous oil that solidifies upon standing.

General procedure for deprotection (ii): The methyl-ester protected starting material was dissolved in 6 mL of a 3:1 mixture of THF and water. LiOH (4 equivalents) was added into the solution and the reaction mixture was stirred at room temperature until the reaction was found to be complete by TLC (10% MeOH in DCM). The solvent was removed in vacuo to afford the product as a white solid.

General procedure for alkylation (iii): Both secondary amine and 2.1 equivalents of compound 94 were dissolved in acetonitrile. Twenty equivalents of $Na_2CO_3$ were added into the reaction mixture and the reaction was stirred at room temperature over night. The resulting milky solution was filtered and the solvent was removed in vacuo to afford the crude product as an oil. This was then subsequently purified by column chromatography (10% MeOH in DCM) to afford the product as a very viscous oil that solidifies upon standing.

General procedure for synthesis of cold Ga complexes: The ligand was dissolved in a $CH_3OH$-water mixture (1:2) and acidified to pH 2 by addition of 0.1 M HCl. $Ga(NO_3)_3 \cdot 6H_2O$ (1 equivalent) was added and the pH was adjusted by addition of 0.1 M NaOH to 4.5. The reaction mixture was stirred at 60° C. for 2 h. The solvent was removed in vacuo to afford the complex as a white solid in quantitative yield.

General procedure for labelling with $^{67}$Ga or $^{68}$Ga: 100 μL of $^{67}$GaCl$_3$ (1 mCi) or $^{68}$Ga$^{3+}$ in a 0.1 M HCl solution was added into $10^{-4}$ M solution of ligand in 10 mM NaOAc solution (pH 4.5) and left to react for 10 minutes at room temperature. The reaction was monitored by analytical HPLC (gradient: A: NaOAc buffer, pH 4.5, B: $CH_3OH$. 0-100% B linear gradient 20 min). Specific activity for $^{68}$Ga labeling decay corrected with activity of 16.5 mCi/3 mL Transferrin competition: [67]GaCl$_3$ was added into 10$^{-4}$ M solution of ligand in 10 mM NaOAc solution (pH 4.5). Complex formation was checked on HPLC. A 400 μL aliquot was added to 1 mg/mL apo-transferrin in a NaHCO$_3$ solution (10 mM, 600 μL) and incubated at 37° C. (water bath). Complex stability was checked at time points 10 minutes, 1 h and 2 h via analytical HPLC. No decomposition was detected.
Basic Chelator Synthesis:

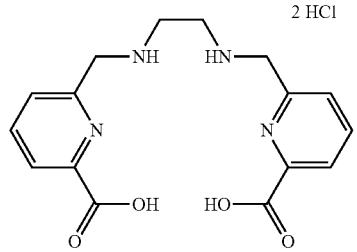 [SMILES: O=C(O)c1cccc(CNCCNCc2cccc(C(=O)O)n2)n1]

H$_2$dedpa.2HCl

Dimethyl pyridine-2,6-dicarboxylate was synthesized according to the literature method (E. J. T. Chrystal, L. Couper, D. J. Robins, Tetrahedron 1995, 51,10241-10252).

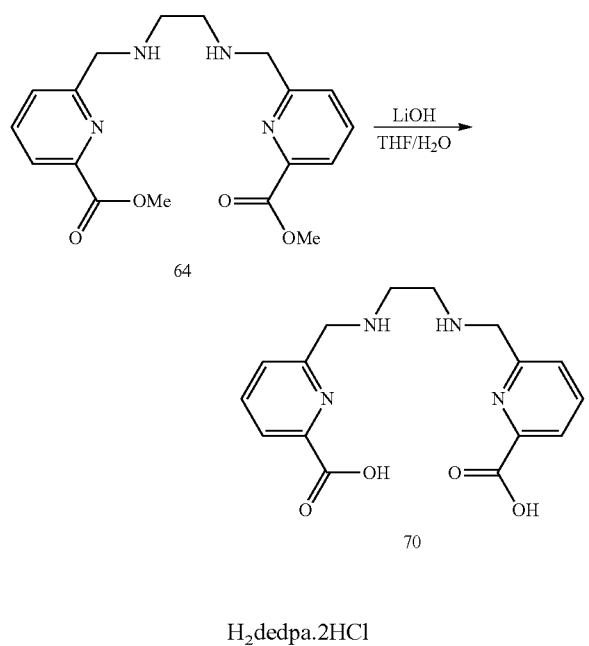

H$_2$dedpa.2HCl

Protected precursor 1,2-{6-(methoxycarbonyl)pyridin-2-yl}methylaminoethane was synthesized according to the literature.[31] Deprotection of 1,2-{6-(methoxycarbonyl)-pyridin-2-yl}methylaminoethane was achieved by dissolving (37 mg, 0.1 mmol) in 4 mL of a 1:1 mixture of THF and water. LiOH (10 mg, 0.41 mmol, 4.1 eq) was added and the reaction mixture was stirred for 2.5 h. Reaction monitoring was performed by TLC (20% CH$_3$OH in DCM, t$_R$ of starting material: 0.8, t$_R$ of product: 0.0). The solvent was removed in vacuo and 12 M HCl was added to the glass-like solid to precipitate the dihydrochloride salt, which was collected by filtration to afford 24 mg (0.059 mmol, 59%) of a white solid. $^1$H NMR (DMSO-d$_6$, 300 MHz) δ: 8.12-8.09 (m, 4H, ortho-/para-H), 7.78 (d, ortho-H), 4.52 (s, 2H, CH$_2$), 3.51 (d, 2H, CH$_2$). $^{13}$C NMR (DMSO-d$_6$, 150 MHz) δ: 166.1, 153.5, 148.1, 139.7, 127.2, 124.9, 104.6, 93.8, 50.7, 43.8. IR (cm$^{-1}$): 2678, 2600, 2427, 1761, 1749, 1599. HR-ESI-MS calcd. for C$_{16}$H$_{19}$N$_4$O$_4$: 331.1406; found: 331.1329 M+H$^+$. Elemental analysis: calcd % for H$_2$dedpa.2HCl (402.8): C 47.65, H 5.00, N 13.81; found: C 47.30, H 5.11, N 13.38.

Figure 6A:
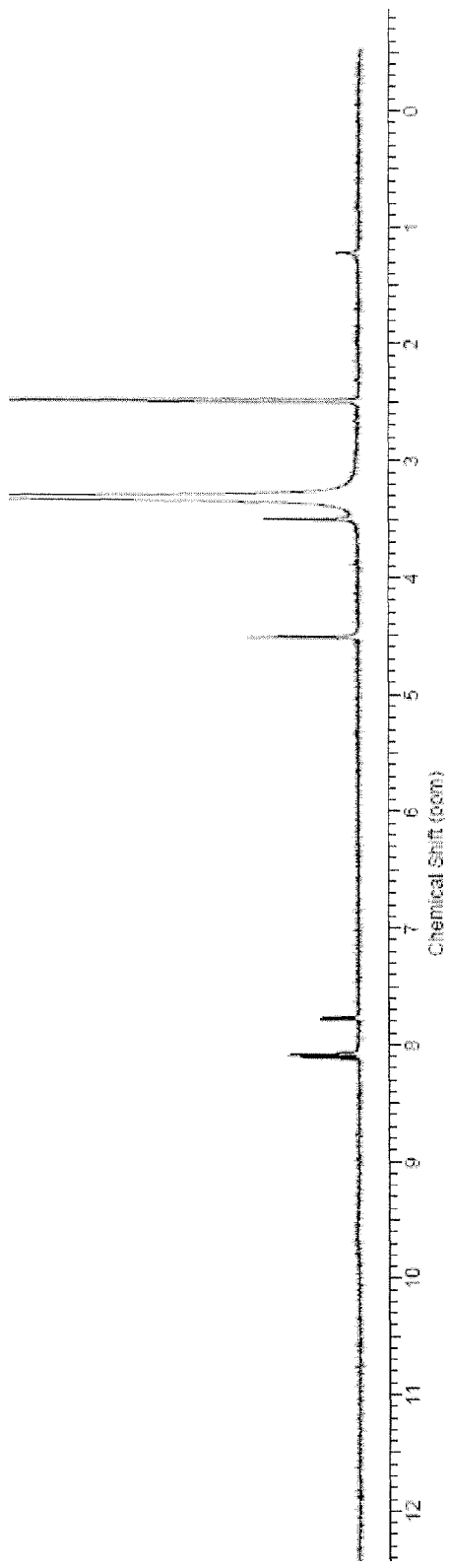
FIG. 6A illustrates the $^1$H-NMR of H$_2$dedpa.2HCl in DMSO-d$_6$.
Figure 6B:
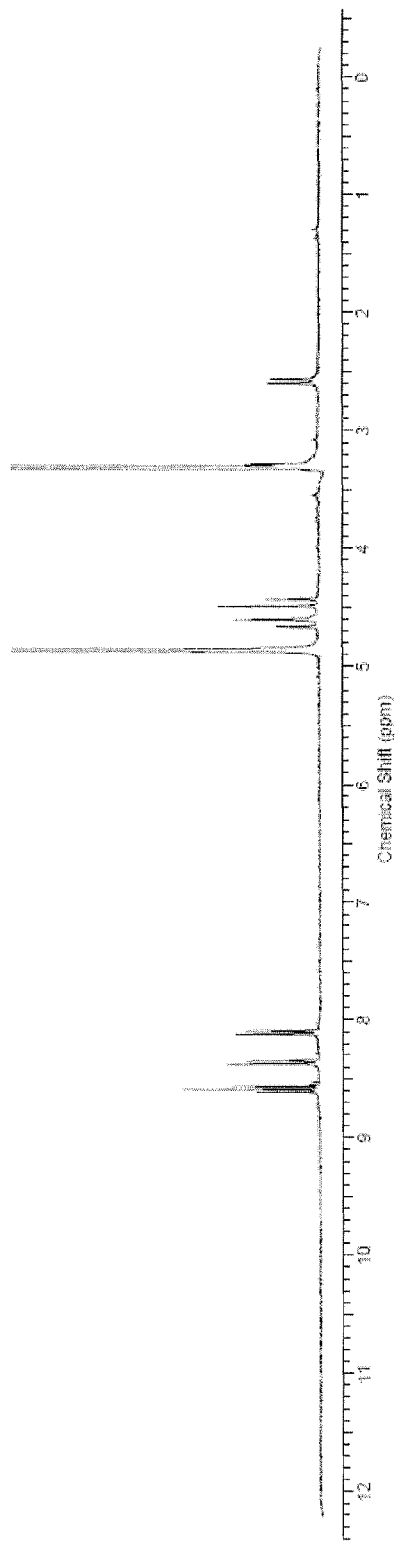
FIG. 6B illustrates the $^1$H-NMR (MeOD-d$_4$, 300 MHz) of Ga(dedpa)NO$_3$.

FIG. 6A illustrates the $^1$H-NMR (DMSO-d$_6$, 300 MHz) of H$_2$dedpa.2HCl.

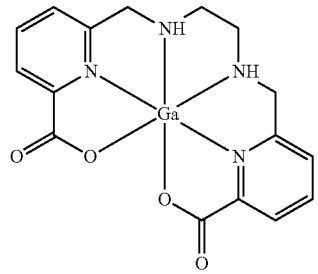

Ga(dedpa) ClO$_4$

Ga(dedpa)ClO$_4$

H$_2$dedpa.2HCl (21 mg, 0.052 mmol) was dissolved in a CH$_3$OH-water mixture (1:2). Ga(ClO$_4$)$_3$.6H$_2$O (24 mg, 0.052 mmol) was added and the pH was adjusted to 4.5 by addition of 0.1 M NaOH. The reaction mixture was heated for 30 minutes and then set aside in the fume hood for slow evaporation. After 72 h, rhombic colorless crystals suitable for X-ray diffraction had precipitated in quantitative yield. $^1$H NMR (300 MHz, DMSO-d$_6$) δ: 8.59 (t, 2H, para-H), 8.29 (d, 2H, meta-H), 8.09 (d, meta-H), 4.60-4.32 (dd, 4H, py-CH$_2$—NH), 3.06 (m, 2H, CH$_2$), 2.4 (m, 2H, CH$_2$). $^{13}$C NMR (75 MHz, DMSO-d$_6$) δ: 162.0, 150.4, 145.2, 144.1, 129.2, 126.5, 122.0. HR-ESI-MS calc. for C$_{16}$H$_{16}$$^{69}$GaN$_4$O$_4$: 397.0427; found: 397.0431 M$^+$. IR (cm$^{-1}$): 2360, 2341, 1695, 1664, 1606. Product t$_R$ on HPLC: 5.5 minutes (gradient: A: NaOAc buffer, pH 4.5, B: MeOH. 0-5% B linear gradient 20 min).

[67]Ga Radiolabeling of Dedpa and Derivatives [67/68]Ga(dedpa)$^+$.

General Labelling Procedure:

100 μL of [67]GaCl$_3$ (1 mCi) or [68]Ga$^{3+}$ in a 0.1 M HCl solution was added to 900 μL of a 10$^{-4}$ M solution of ligand in 10 mM NaOAc solution (pH 4.5) and left for 10 minutes at RT. The reaction progress was monitored by analytical HPLC which showed that the reaction had proceeded to 99%. Product t$_R$ on HPLC: 6.1 minutes (gradient: A: NaOAc buffer, pH 4.5, B: CH$_3$OH. 0-5% B linear gradient 20 min). The high specific activity of 9.837±0.136 mCi/nmol, with yields 99.9±0.1% was achieved with 900 μL of a 10$^{-7}$M solution of H$_2$dedpa in 10 mM NaOAc solution (pH 4.5) and 100 μL [68]Ga$^{3+}$ in a 0.1 M HCl solution (0.98 mCi) under standard labeling conditions (as described above); this experiment was done in triplicate. Radiochemical yield was determined by HPLC using a C18 reverse phase column and a gradient elution. The radiolabeled products were identified by comparison of the radiation detector trace and the UV/visible detector trace of a cold complex as a standard, where the cold complex is the non-radioactive gallium complex that has been prepared and characterized to confirm its chemical identity. Results from $^{67}$Ga radiolabelling are summarized in Table 1.

TABLE 1

| | Complex | Ret. Time (Gradient) | Temp. | Radiochemical yield |
|---|---|---|---|---|
| 1 | (structure: N-propyl bis(picolyl) with two pyridine-carboxylic acid arms) | 8.9 min (B) | RT 95° C. | 73% mixture |
| 2 | (structure: ethylenediamine N,N'-diacetic acid with two picolyl arms) | 7.7 min (B) 6.9 min | RT 95° C. | 70% 88% |
| 3 | (structure: ethylenediamine with three carboxymethyl arms and two picolyl arms, cationic) | 3.68 min (A) | RT | 60% |
| 4 | (structure: propylenediamine N,N'-diacetic acid with two picolyl arms) | 5.3 min (B) 4.8 min | RT 95° C. | 92% 72% |
| 5 | (structure: macrocycle with two pyridine-carboxylic acids linked by ethylene diamine) | 6.19 min (A) 5.5 min | RT | 99% |
| 6 | (structure: macrocycle with two pyridine-carboxylic acids linked by propylene diamine) | 7.6 min (A) 7.0 min | RT 95° C. | 44% 44% |

TABLE 1-continued

Results from $^{67}$Ga radiolabelling

| Complex | Ret. Time (Gradient) | Temp. | Radiochemical yield |
|---|---|---|---|
| 7 [structure] | 4.95 min (A) | RT | 88% |
| 8 [structure] | 6.29 min (B) | RT | 95% |
| 9 [structure] | 7.5 min (B) | RT 95° C. | 95% |

Gradients:
A: 0 to 5% MeOH in 10 mM NaOAc (pH 4.5), 20 min.
B: 0 to 100% MeOH in 10 mM NaOAc (pH 4.5), 20 min.
Italicized values represent cold complex retention times Entry 5 in Table 1 shows the fast, high radiochemical yield incorporation of $^{67}$Ga into the dedpa chelate. The radiochemical yield after only 10 minutes under mild room temperature aqueous conditions was 99% as determined by HPLC. Chelates with small structural differences do not show the same rapid, high yield, radiolabeling under mild conditions as dedpa. For example both entry 6, which differs from dedpa by one extra carbon between the primary amines, and entry 2, which differs from dedpa by the carboxylate coordinating groups attached to the alkyl amine rather than the pyridyl ring, do not achieve >95% radiochemical yield in 10 minutes even at increased temperatures. Dedpa shows high affinity for Ga and fast radiolabeling kinetics, even when compared to similar chelates.

Entry 8, which contains two extra carboxylate groups compared to dedpa also gave high radiochemical yields (95%) under mild conditions in 10 minutes. This chelate is the basis for a bifunctional chelate that retains the chelate structure of dedpa, while allowing conjugation to biomolecules via the additional two carboxylate arms.

$^{111}$In Radiolabeling of Dedpa and Derivatives

The chelators 1-6 (Table 2) were made up as stock solutions (1 mg/mL, ~10$^{-3}$M), which were then diluted into buffered labeling solutions (100 μL of 10$^{-3}$ M chelate stock solution into 900 μL of pH 4.5, 10 mM NaOAc buffer, final working solution of ~10$^{-4}$ M). A 7 μL aliquot of the $^{111}$In stock solution (7 mCi/10 μL) was diluted with 93 μL of deionized water to make a working 6.5 mCi/100 μL $^{111}$In solution. A 10 μL aliquot of the $^{111}$In working solution was transferred into each working chelator solution (646-692 μCi), allowed to react at room temperature for 10 minutes, and then analyzed by HPLC, Radiolabeling results of chelators 1-6 are shown in Table 2. Areas under the peaks observed in the radioactive HPLC trace were integrated to determine radiochemical yields, % impurities, and % unlabeled $^{111}$In. Further experiments demonstrated that compound 5 labeled quantitatively in 15-20 minutes, and compounds 2 and 4 labeled quantitatively in 30 minutes. The HPLC system used for analysis consisted of a Waters Alliance HT 2795 separation module equipped with a Raytest Gabi Star NaI (Tl) detector and a Waters 996 photodiode array (PDA) detector. A Phenomenex Flydrosynergy RP C18 4.6 mm×150 mm analytical column was used for all radiolabeled chelate complexes. Elution conditions used were gradient: A: 10 mM NaOAc buffer pH 4.5, B: CH$_3$CN. 0-100% B linear gradient 20 min).

TABLE 2

[111]In radiolabeling results from chelators 1-6 with reported radiolabeling yields (% yield) determined by HPLC, and HPLC retention times ($R_T$) of $^{111}$In complexes.

| # | Structure | Results |
|---|---|---|
| 1 | | >99% yield, $R_T$ = 5 min |
| 2 | | 91.6% yield, 3.6% impurities, 4.8% free $^{111}$In, $R_T$ = 4.5 min |
| 3 | | >99% yield, $R_T$ = 4.6 min |
| 4 | | 83.8% yield, 5.7% impurities, 10.5% free $^{111}$In, $R_T$ = 4.5 min |
| 5 | | 87.9% yield, 12.1% free $^{111}$In, $R_T$ = 4.9 min |

TABLE 2-continued

111In radiolabeling results from chelators 1-6 with reported radiolabeling yields (% yield) determined by HPLC, and HPLC retention times ($R_T$) of 111In complexes.

| | | | |
|---|---|---|---|
| 6 | 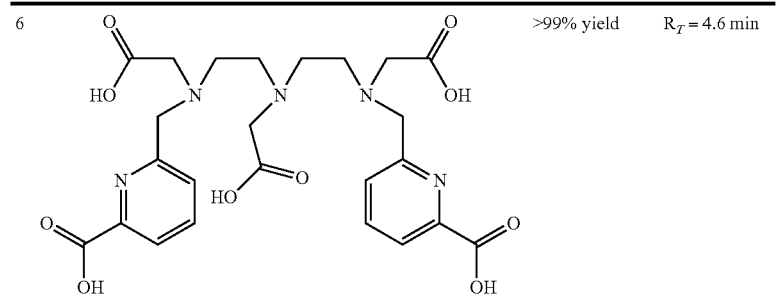 | >99% yield | $R_T$ = 4.6 min |

Human Apo-Transferrin Competition Experiments.

Human apo-transferrin (Aldrich) was suspended in 10 mM NaHCO$_3$ buffer at pH 6.9. Labeling solutions were prepared with chelators and 111In in 10 mM NaHCO$_3$ buffer at pH 5.5, and allowed to sit for 20-30 minutes. Quantitative formation of 111In-chelate complexes was confirmed by HPLC (same methods as in Example 2). 111In(DOTA) was formed using a microwave reactor (Biotage) at 80° C. for 10 minutes to ensure quantitative labeling. Competition experiments for all 8 chelators studied (Table 3) were performed with preformed 111In-chelate complexes at a concentration of 36.5 mM, and with human apo-transferrin at a concentration of ~10 mM. Samples were left to sit in sterile scintillation vials for 1 hour and 24 hours at ambient temperature. Chelate stability was determined using size-exclusion 'desalting' columns (GE Healthcare PD-10 pre-packed columns, Sephadex G-25 M). All compounds smaller than ~5000 Daltons were retained by the PD-10 columns, and all transferrin was eluted. PD-10 columns were conditioned by discarding the contained bactericidal solution and eluting 20 mL of phosphate buffered saline (PBS, purchased from BioWhittaker). For analysis, the competition experiment solutions were diluted to 2.5 mL with PBS, measured with a Capintec scintillation counter, loaded onto PD-10 columns, and allowed to elute into a waste container fully. An additional 3.5 mL of PBS was then loaded onto the columns and collected into a sterile scintillation vial. PD-10 columns were discarded after a single use. The vial containing the eluent was then measured with a Capintec scintillation counter to determine the amount of 111In bound to transferrin. The difference in radioactivity between the competition experiment solutions and the eluent from the PD-10 columns was used to determine the percent 111In bound to transferrin, and therefore the percent stability of the complexes.

TABLE 3

111In-chelate stability experiments - binding competition with human apo-transferrin at ambient temperature

| Pre-formed chelator complex | Activity loaded on PD-10 column (µCi) | Activity eluted from PD-10 column (µCi) | % 111In-chelate stability at 1 hour |
|---|---|---|---|
| 1 hour stability | | | |
| 111In(1) | 410 | 10 | 98 |
| 111In(2) | 403 | 40 | 90 |
| 111In(3) | 325 | 30 | 91 |
| 111In(4) | 406 | 30 | 93 |
| 111In(5) | — | — | — |
| 111In(6) | 436 | 50 | 89 |
| 111In(DTPA) | 386 | 55 | 86 |
| 111In(DOTA) | — | — | — |
| 24 hour stability | | | |
| 111In(1) | 324 | 185 | 43 |
| 111In(2) | 318 | 30 | 91 |
| 111In(3) | 270 | 40 | 85 |
| 111In(4) | 322 | 30 | 91 |
| 111In(5) | 440 | 55 | 88 |
| 111In(6) | 342 | 30 | 91 |
| 111In(DTPA) | 333 | 40 | 88 |
| 111In(DOTA) | 443 | 85 | 81 |

High Specific Activity 68Ga Radiolabeling of Dedpa
Concentration Dependent Radiolabeling of Dedpa and Maximum Specific Activity 68GaCl$_3$ (1 mCi) in a 0.1 N HCl solution was added to ligand solutions with concentrations from $10^{-4}$ M down to $10^{-8}$ M in 10 mM NaOAc solution (pH 4.5) and left to react for 10 minutes at room temperature. The radiochemical yield was monitored by HPLC as described above.

The dedpa chelate gave the same high radiochemical yields under mild room temperature conditions within 10 minutes with 68Ga as was shown in example 1 with 67Ga. By serial dilutions of the chelate solution used in labelling it was determined that a 0.1 µM chelate concentration was needed for efficient radiolabeling. The maximum specific activity, defined here as mCi of isotope/nmol of chelate, achieved was 10 mCi/nmol without post labelling purification.

Stability of 67/68Ga(dedpa)$^+$
Stability Assessment by 67/68Ga(Dedpa)$^+$ Competition with Transferrin
Complex Stability Against Transferrin:

For apo-transferrin competition, 67GaCl$_3$ was added to a $10^{-4}$ M solution of ligand in 10 mM NaOAc solution (pH 4.5). Complex formation was checked by HPLC. A 400 µL aliquot was added to 1 mg/mL apo-transferrin in NaHCO$_3$ solution (10 mM, 600 µL) and incubated at 37° C. (water bath). Complex stability was checked at time points 10 minutes, 1 h and 2 h via analytical HPLC. No decomposition was detected.

FIG. 9 illustrates the labelling trace of 67Ga(dedpa)$^+$ on HPLC. ($t_R$: 6.1 minutes (gradient: A: NaOAc buffer, pH 4.5, B: CH$_3$OH. 0-5% B linear gradient 20 min). Yield: 99%).

Transferrin is an iron transport protein found in high concentrations in the blood that has an affinity for Ga due to the similar ionic size and charge of $Ga^{3+}$ and $Fe^{3\circ}$. Direct competition of $Ga(dedpa)^+$ with apo-transferrin gives an indication of the radiolabeled complexes' expected stability in vivo. As no decomposition was detected within 2 h, $Ga(dedpa)^+$ is expected to have in vivo stability appropriate for imaging with $^{68}Ga$.

Comparison of Dedpa to Industry Standard Chelate NOTA Radiolabeling Kinetics Assessment by Competition of Dedpa and NOTA Competition for chelation experiment with NOTA: $^{67}GaCl_3$ was added to $10^{-4}M$ solution of both NOTA and $H_2$dedpa in 10 mM NaOAc solution (pH 4.5). After a reaction time of 10 minutes at room temperature the reaction mixture was checked for the formed complex by analytical HPLC. Over 98% of the $^{67}Ga$-dedpa complex was detected opposed to 0.2% Ga-NOTA.

Transchelation of Ga from NOTA by Dedpa $^{67}GaCl_3$ was added into $10^{-4}$ M solution of NOTA in 10 mM NaOAc solution (pH 4.5). Complete complexation of the $^{67}Ga^{3+}$ by NOTA was confirmed by HPLC. An equivalent amount of the dedpa ligand was then added to the $^{67}Ga$-NOTA product. After 10 minutes at room temperature the reaction mixture was analyzed by HPLC. Over 98% of the $^{67}Ga$-dedpa complex was formed as opposed to only 0.2% Ga-NOTA, confirming that the acyclic dedpa chelate has faster complexation kinetics than the macrocyclic NOTA chelate, as would be expected.

When the Ga-NOTA complex is pre-formed and then an equivalent amount of dedpa is added, Ga is transchelated from the Ga-NOTA complex to form Ga-dedpa. About 10% of Ga-NOTA was converted to Ga-dedpa in 10 minutes. As Ga-NOTA is known to be very stable, this result was unpredicted and indicates greater affinity of Ga for dedpa.

Synthesis of di-tert-butyl 6,6'-((3,10-dioxo-2,11-dioxa-5,8-diazadodecane-5,8-diyl)bis(methylene))dipicolinate

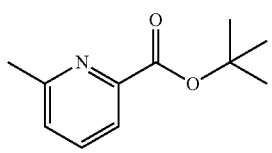

tert-butyl 6-methylpicolinate 6-methylpicolinic acid (4.86 g, 35.5 mmol), boron trifluoride etherate (0.709 mL, 20 μL/mmol 6-methylpicolinic acid), and t-butyl 2,2,2-trichloroacetimidate (12.7 mL, 70.91 mmol, 2 eq.) in DCM (200 mL) were added to a round-bottomed flask and refluxed for two days. $NaHCO_3$ was added to quench residual $BF_3$. The mixture was stirred for 10 minutes. The solid was filtered off, the filtrate was collected and the solvent was removed in vacuo. Hexane was added to the milky oil to precipitate residual starting materials, which could be filtered off. The solvents were evaporated to afford the clean product as a light yellow oil (2.7683 g, 14.33 mmol, 40.4%). $^1H$ NMR (300 MHz, $CDCl_3$, δ): 7.78 (d, 1H, ortho-H), 7.62 (t, 1H, meta-H),7.25 (d, 1H, ortho-H), 2.62 (s, 3H, $CH_3$), 1.60 (s, 9H, (s, 9H, $^tBu$-$CH_3$)). $^{13}C$ NMR (300 MHz, $CDCl_3$, δ): 164.4, 159.2, 137.1, 126.4, 122.05, 82.2, 28.3, 24.7 HRMS (ESI+, MeOH): 216.099 M+Na⁺.

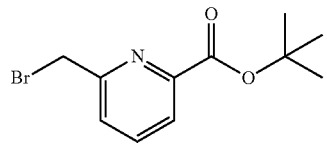

tert-butyl 6-(bromomethyl)picolinate

N-bromosuccinimide (1.95 g, 10.99 mmol), 6-methylpicolinic acid tert-butyl ester (2.1175 g, 10.96 mmol), and benzoyl peroxide (0.27 g, 1.10 mmol, 0.1 eq.) were dissolved in $CCl_4$ (150 mL) and refluxed for 6.5 hours while monitored by TLC (3:1 hexane: ethyl acetate, $R_f$=0.28). The reaction mixture was filtered and the solvent was removed in vacuo. The light orange oil was redissolved in DCM and extracted three times with an aqueous solution of saturated $NaHCO_3$ (50 mL). The organic layer was dried with $MgSO_4$ and the solvent was removed in vacuo. The crude product was recrystallised twice from a hexane/ethyl acetate mixture (3:1) in the freezer afford the mono-brominated product as small off-white crystals (0.511 g, 1.88 mmol, 17.1%). $^1H$ NMR (300 MHz, $CDCl_3$, δ): 7.92 (d, 1H, ortho-H), 7.82 (t, 1H, meta-H), 7.65 (d, 1H, ortho-H), 4.65 (s, 2H, $CH_2$), 1.64 (s, 9H, $^tBu$-$CH_3$). $^{13}C$ NMR (300 MHz, $CDCl_3$, δ): 171.0, 161.0, 157.9, 138.4, 127.0, 124.4, 60.9, 33.9, 28.6.

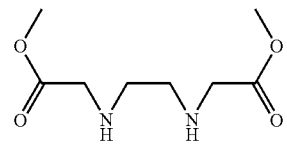

dimethyl 2,2'-(ethane-1,2-diylbis(azanediyl))diacetate

Dimethyl 2,2'-(ethane-1,2-diylbis(azanediyl))diacetate was synthesized according to the procedure described in G. N. Kaluderovic et al., Inorg. Chim. Acta, 361, 2008, 1395-1404.

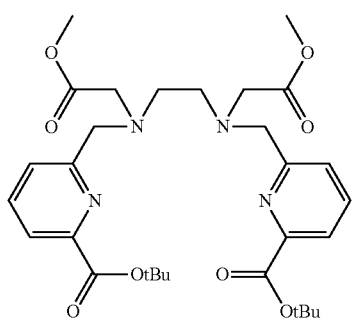 [SMILES: COC(=O)CN(CCN(CC(=O)OC)Cc1cccc(C(=O)OC(C)(C)C)n1)Cc1cccc(C(=O)OC(C)(C)C)n1]

di-tert-butyl 6,6'-((3,10-dioxo-2,11-dioxa-5,8-diazadodecane-5,8-diyl)bis(methylene))dipicolinate O,O'-dimethyl-ethylenediamine-N,N'-diacetate dihydrochloride monohydrate (G. N. Kaluderovic et al. Inorg. Chim.

Acta 361, 2008, 1395-1404) (0.411 g, 1.48 mmol), 2 (0.808 g, 2.96 mmol, 2 eq.), KI (0.581 g, 3.5 mmol, 2.4 eq.) and $K_2CO_3$ (0.734 g, 5.3 mmol) were added into dimethylformamide (DMF) (120 mL) and stirred at 65 C for two days. The reaction mixture was poured into a separation funnel with DCM and saturated aqueous NaCl solution. The organic layer was separated and extracted 5 times with saturated aqueous NaCl solution to remove residual DMF. Trituration with hexane afforded the product with an approximate 85% purity (according to NMR). $^1$H NMR (300 MHz, $CDCl_3$, δ): 7.82 (m, 2H, ortho-H), 7.68 (m, 4H, meta-H, para H), 3.96 (s, 4H, $CH_2$), 3.63 (s, 6H, $CH_3$), 3.40 (s, 4H, $CH_2$), 2.79 (s, 4H, $CH_2$), 1.58 (s, 18H, $^t$Bu-$CH_3$). HRMS (ESI, MeOH): 609.291 $M+Na^+$.

(1,2-N,N'-{p-Nitrobenzyl}methyl-N,N'-6-{methoxycarbonyl}-pyridin-2-yl methylamino)ethane (65)

64 was synthesized according to the literature.[31] 4-Nitrobenzyl bromide (135 mg, 0.625 mmol) was dissolved in 20 mL acetonitrile together with 64 (105 mg, 0.293 mmol). $Na_2CO_3$ (400 mg) was added into the solution and the reaction was stirred overnight at 70° C. Subsequently, the suspension was filtered and the solvent removed in vacuo. The resulting orange oil was purified by column chromatography (Silica, $CH_2Cl_2$); the product was eluted with 5% $CH_3OH$, and isolated as an orange oil (60 mg, 0.095 mmol, 33%, $R_f$: 0.6). $^1$H NMR (300 MHz, $CDCl_3$) δ: 8.01 (d, 2H, benzyl-H), 7.98 (d, 2H, py-H), 7.76 (t, 2H, py-H), 7.59 (d, 2H, py-H), 7.46 (d, 2H, benzyl-H), 4.98 (s, 6H, $CH_3$) 3.83 (s, 4H, py-$CH_2$—NH), 3.69 (s, 4H, benzyl-$CH_2$—NH), 2.71 (s, 4H, —$CH_2$—$CH_2$—). $^{13}$C NMR: (75 MHz, $CDCl_3$) δ: 165.8, 160.1, 147.6, 147.3, 137.6, 129.3, 125.9, 123.8, 123.7, 60.6, 58.7, 53.1, 52.3. HR-ESI-MS calcd. for $C_{32}H_{32}N_6NaO_8$: 651.2179; found: 651.2289 $M+Na^+$.

(1,2-N,N'-{p-Nitrobenzyl}methyl-N,N'bis-6-carboxy-2-pyridylmethyl ethylenediamine (66)

Figure 7A:
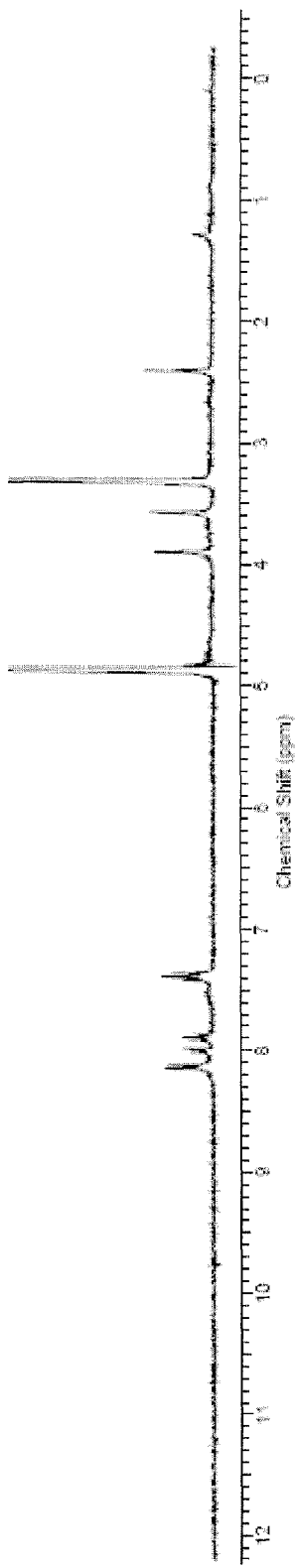
FIG. 7A illustrates the $^1$H-NMR of H$_2$66 in MeOD-d$_4$.

64 (27 mg, 0.042 mmol) was dissolved in 4 mL of a 3:1 mixture of THF and water. LiOH (5 mg, 0.21 mmol) was added to the solution resulting in an immediate color change of the solution. The reaction was monitored by TLC and found to be complete after 45 min. The solvent was removed in vacuo to afford a white solid (25 mg, 0.041 mmol, 97%). $^1$H NMR (400 MHz, MeOD-$d_4$) δ: 8.12 (d, 2H, benzyl-H), 8.10 (d, 2H, py-H), 7.91 (t, 2H, py-H), 7.42 (d, 2H, py-H), 7.36 (d, 2H, benzyl-H), 3.88 (s, 4H, py-$CH_2$—NH), 3.56 (s, 4H, benzyl-$CH_2$—NH), 2.41 (s, 4H, —$CH_2$—$CH_2$—). $^{13}$C NMR (100 MHz, MeOD-$d_4$) δ: 172.5, 159.2, 155.0, 148.78, 145.0, 139.9, 132.2, 125.9, 124.4, 123.4, 61.0, 57.6, 31.1. HR-ESI-MS calcd. for $C_{30}H_{27}N_6O_8$: 599.1890; found: 599.1887 $M-H^+$. FIG. 7A illustrates the $^1$H-NMR (MeOD-$d_4$, 300 MHz) of $H_2$66.

Ga(66)($NO_3$)

Figure 7B:
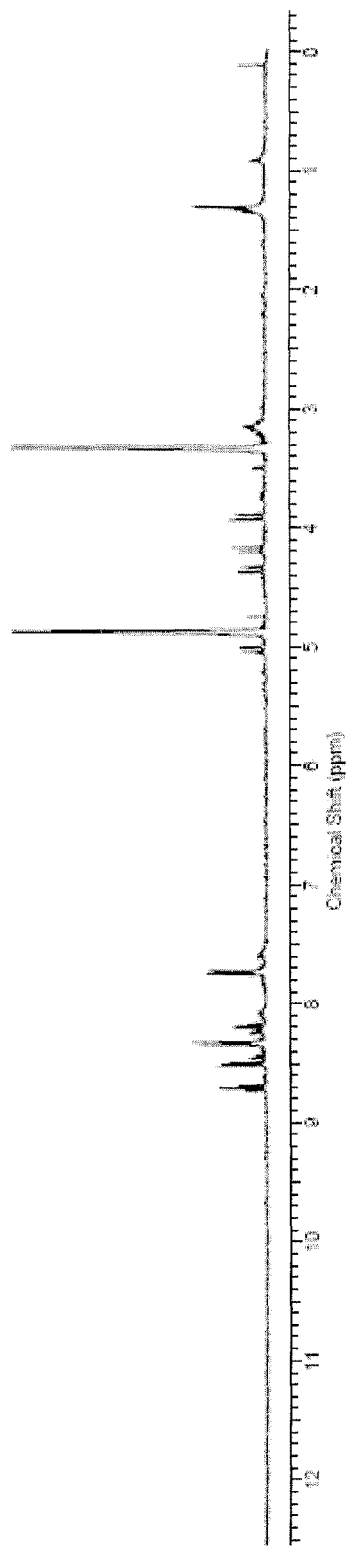
FIG. 7B illustrates the $^1$H-NMR of Ga(66)NO$_3$ in MeOD-d$_4$.

66 (7 mg, 0.011 mmol) was dissolved in a $CH_3OH$-water mixture (1:2). $Ga(NO_3)_3$·$6H_2O$ (4 mg, 0.011 mmol) was added and the pH was adjusted to 4.5 by addition of 0.1 M NaOH. The reaction mixture was stirred at 60° C. for 2 h. The solvent was removed in vacuo to afford a white solid in quantitative yield. The solid was redissolved in a mixture of water and methanol (1:2). Colorless plates suitable for X-ray diffraction were obtained by slow evaporation of the solvent mixture. $^1$H NMR (400 MHz, $CD_3OD$) δ: 8.71 (t, 2H, py-H), 8.49 (d, 2H, py-H), 8.32 (d, 2H, benzyl-H), 8.18 (d, 2H, py-H), 7.72 (d, 2H, benzyl-H), 5.03-4.34 (dd, 4H, py-$CH_2$—NH), 4.18-3.87 (dd, 4H, —$CH_2$—$CH_2$—), 3.13 (s(br), 4H, benzyl-$CH_2$—NH). $^{13}$C NMR (150 MHz, $CD_3OD$) δ: 165.1, 152.0, 150.3, 148.3, 145.7, 138.1, 134.5, 129.8, 125.6, 124.8, 57.7, 55.4, 48.1. HR-ESI-MS calcd. for $C_{30}H_{26}N_6O_8$$^{69}$Ga: 667.1068; found: 667.1075 $^{69}M^+$. FIG. 7B illustrates the $^1$H-NMR (MeOD-$d_4$, 300 MHz) of Ga(66)$NO_3$.

Figure 10:
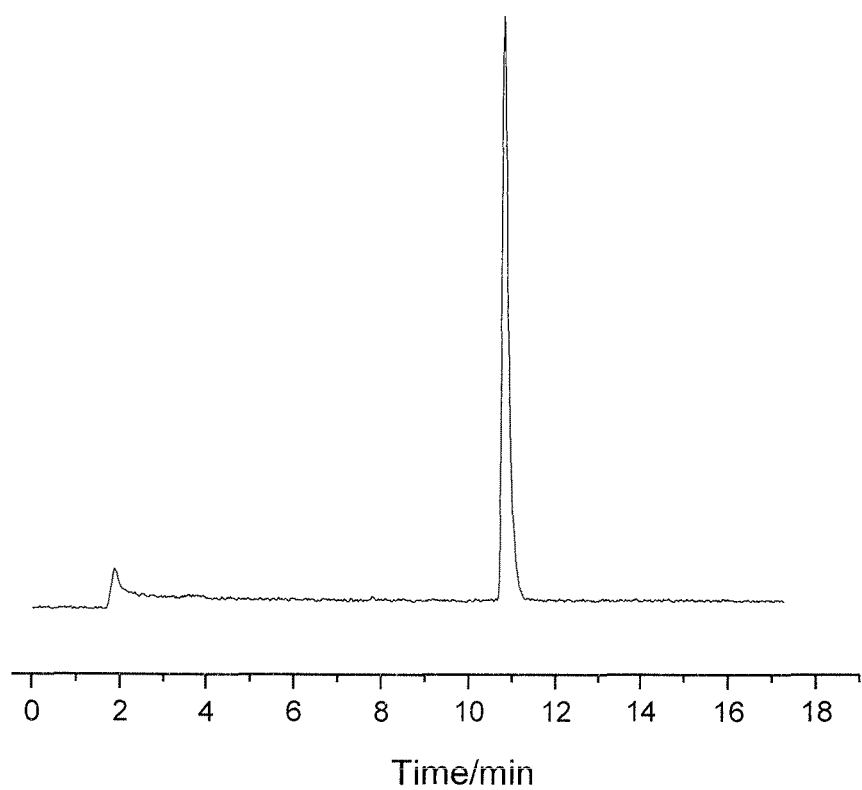
FIG. 10 illustrates the labelling trace of $^{67}$Ga(66)$^-$ on HPLC.

$^{67/68}$Ga(66)$^+$. 100 μL of $^{67}$$GaCl_3$ or $^{68}$$Ga^{3+}$ (1 mCi) in a 0.1 M HCl solution was added into $10^{-4}$ M solution of ligand in 10 mM NaOAc solution (pH 4) and left to react for 10 minutes at room temperature. Reaction control was performed by analytical HPLC which showed that the reaction had proceeded to 98%. Product $t_R$ on HPLC: 10.8 minutes (gradient: A: NaOAc buffer, pH 4.5, B: $CH_3OH$. 0-100% B linear gradient 20 min). For the apo-transferrin competition, $^{67}$$GaCl_3$ was added to $10^{-4}$ M solution of 66 in 10 mM NaOAc solution (pH 4.5). Complex formation was checked on HPLC (peptide column). A 400 μL aliquot was added to 1 mg/mL apo-transferrin in a $NaHCO_3$ solution (10 mM, 600 μL) and incubated at 37° C. (water bath). Complex stability was checked at time points 10 minutes, 1 h and 2 h via analytical HPLC. Complex was 51% intact after 2 h. FIG. 10 illustrates the labelling trace of $^{67}$Ga(66)$^+$ on HPLC. ($t_R$: 10.8 minutes (gradient: A: NaOAc buffer, pH 4.5, B: $CH_3CN$. 0-100% B linear gradient 20 min). Yield: 98%)

2-(p-Nitrobenzyl)-N,N'-6-{methoxycarbonyl}-pyridin-2-yl methylamino)ethane (68). 67 and 4 were synthesized according to the literature.[39,40] To a mixture of 67 (0.46 g, 2.36 mmol) in methanol (50 mL), 4 (0.78 g, 4.72 mmol) was added. The mixture was refluxed for 2 h and then cooled to 0° C. in an ice bath. After cooling, $NaBH_4$ (0.139 g, 3.67 mmol) was added slowly and stirred at 0° C. for 2 h. Saturated aqueous $NaHCO_3$ was then added (150 mL) and the mixture stirred for 15 min, followed by extraction with DCM (5×80 mL). The combined DCM fractions were dried over $MgSO_4$ and evaporated to give 0.96 g of crude yellow oil. Subsequent purification of a 50 mg aliquot with column chromatography (10% $CH_3OH$ in DCM) afforded the product as a colorless oil (5 mg, 0.012 mmol, 8%, $R_f$: 0.05). $^1$H NMR (300 MHz, $CDCl_3$) δ: 8.12 (d, 2H, benzyl-H), 7.99 (d, 2H, py-H), 7.78 (t, 2H, py-H), 7.54 (dd, 2H, py-H), 7.35 (d, benzyl-H), 4.06-4.03 (m, 4H, py-$CH_2$—NH), 3.97 (s, 6H, $CH_3$), 3.04-2.60 (m, 5H, $CH_2$—CH—$CH_2$). $^{13}$C NMR (75 MHz, $CDCl_3$) δ: 165.9, 160.8, 147.7, 147.6, 147.4, 146.8, 137.7, 130.4, 125.9, 123.8, 58.5, 53.1, 52.6, 52.1, 39.6. HR-ESI-MS calcd. for $C_{25}H_{28}N_5O_6$: 494.2040; found 494.2049 $M+H^+$.

2-(p-Nitrobenzyl)-(1,2-N,N'-{p-nitrobenzyl}methyl-N,N'bis-6-carboxy-2-pyridylmethyl ethylenediamine (69)

Figure 8A:
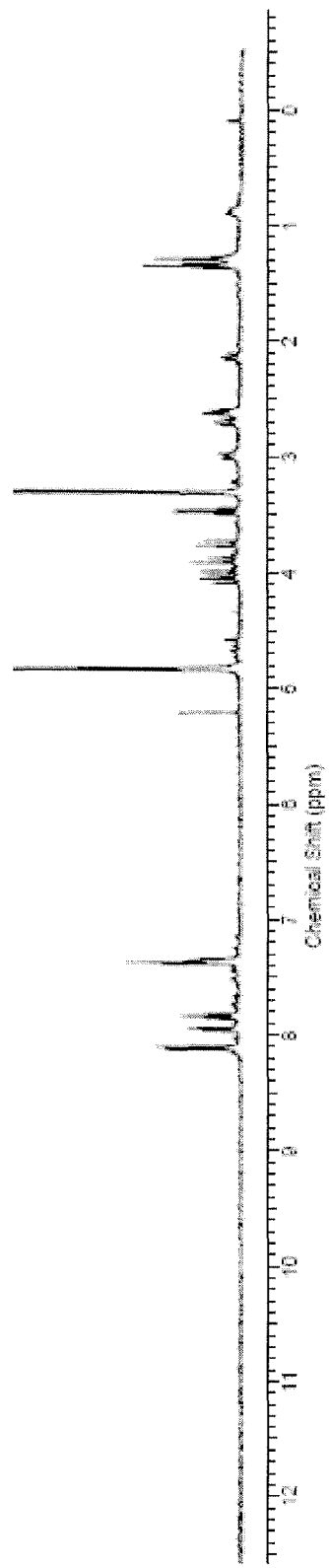
FIG. 8A illustrates the $^1$H-NMR of H$_2$69 in MeOD-d$_4$.

68 (5 mg, 0.012 mmol) was dissolved in 2 mL of a 3:1 mixture of THF and water. LiOH (1 mg, 0.04 mmol) was added into the solution. The reaction was monitored by TLC and found to be complete after 30 minutes. The solvent was removed in vacuo to afford a light yellow solid (4 mg, 0.01 mmol, 83%). $^1$H NMR (400 MHz, $CD_3OD$) δ: 8.15 (d, 2H, benzyl-H), 7.99 (d, 2H, py-H), 7.88 (t, 2H, py-H), 7.41 (m, 4H, py-H/benzyl-H), 4.12-3.91 (m, 4H, py-$CH_2$—NH), 2.75-2.17 (m, 5H, $CH_2$—CH—$CH_2$). $^{13}$C NMR (100 MHz, $CD_3OD$) δ: 165.0, 160.2, 155.2, 149.0, 148.1, 139.5, 131.6, 125.6, 124.6, 123.4, 59.5, 51.9, 39.9, 39.7. HR-ESI-MS calcd. for $C_{23}H_{22}N_5O_6$: 464.1570; found: 464.1581 $M-H^+$. FIG. 8A illustrates the $^1$H-NMR (MeOD-$d_4$, 300 MHz) of $H_2$69.

Ga(69)($NO_3$)

Figure 8B:
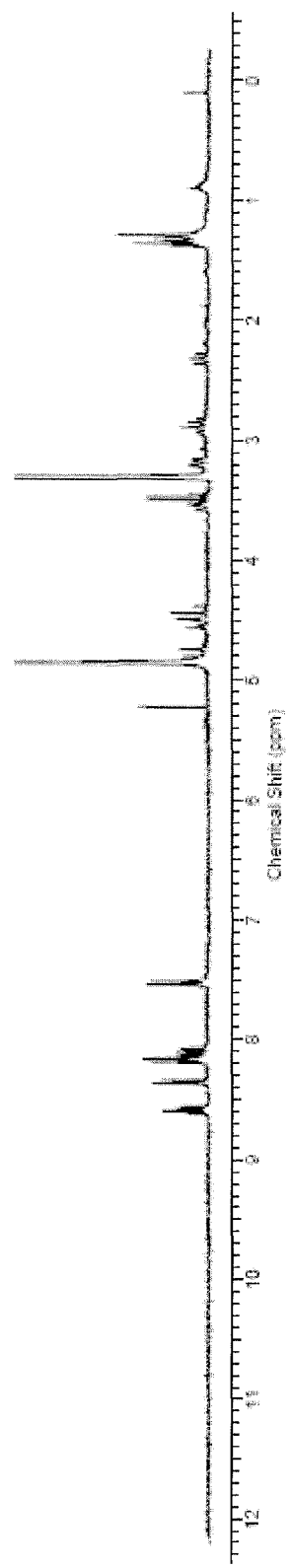
FIG. 8B illustrates the $^1$H-NMR of Ga(69)NO$_3$ in MeOD-d$_4$.

69 (2.5 mg, 5.3 μmol) was dissolved in water. $Ga(NO_3)_3$·$6H_2O$ (2 mg, 5.5 μmol) was added and the pH was adjusted to 5 by addition of 0.1 M NaOH. The reaction mixture was stirred at 60° C. for 2 h. The solvent was removed in vacuo to afford an off-white solid in quantitative yield. $^1$H NMR (300 MHz, CD$_3$OD) δ: 8.62 (t, 2H, py-H), 8.36 (d, 2H, benzyl-H), 8.20-8.09 (m, 4H, py-H), 7.53 (d, 2H, benzyl-H), 4.81-4.39 (m, 4H, py-CH$_2$—NH), 3.59-2.21 (m, 5H, CH$_2$—CH—CH$_2$). $^{13}$C NMR (150 MHz, CD$_3$OD) δ: 165.5, 165.4, 152.1, 151.6, 148.8, 147.4, 147.3, 146.1, 145.9, 145.3, 131.8, 129.1, 129.0, 125.1, 124.7, 124.6, 58.9, 53.7, 51.5, 37.6. HR-ESI-MS calcd. for C$_{23}$H$_{21}$$^{69}$GaN$_5$O$_6$: 532.0748.; found: 532.0743 M$^+$. FIG. 8B illustrates the $^1$H-NMR (MeOD-d$_4$, 300 MHz) of Ga(69)NO$_3$.

$^{67/68}$Ga(69)$^+$

Figure 11:
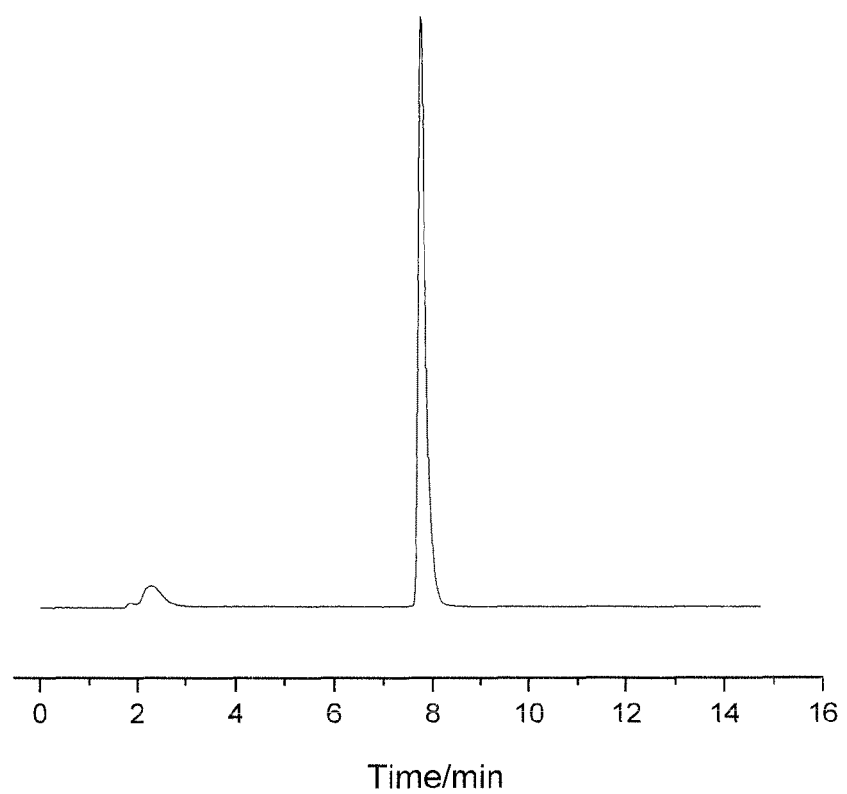
FIG. 11 illustrates the labelling trace of $^{67}$Ga(69)$^-$ on HPLC.

100 μL of $^{67}$GaCl$_3$ or $^{68}$Ga$^{3+}$ (1 mCi) in a 0.1 M HCl solution was added into 10$^{-4}$ M solution of 69 in 10 mM NaOAc solution (pH 4) and left to react for 10 minutes at room temperature. The reaction was monitored by analytical HPLC which showed that the reaction had proceeded to 98%. Product t$_r$ on HPLC: 7.7 minutes (gradient: A: NaOAc buffer, pH 4.5, B: CH$_3$OH. 0-100% B linear gradient 20 min). For the apo-transferrin competition, $^{67}$GaCl$_3$ was added to 10$^{-4}$ M solution of 69 in 10 mM NaOAc solution (pH 4.5). Complex formation was checked on HPLC (peptide column). A 400 μL aliquot was added to a 1 mg/mL apo-transferrin NaHCO$_3$ solution (10 mM, 600 μL) and incubated at 37° C. (water bath). Complex stability was checked at time points 10 minutes, 1 h and 2 h via analytical HPLC. The complex was 97% intact after 2 h. FIG. 11 illustrates the labelling trace of $^{67}$Ga (69)$^+$ on HPLC. (t$_R$: 7.7 minutes (gradient: A: NaOAc buffer, pH 4.5, B: CH$_3$CN. 0-100% B linear gradient 20 min). Yield: 98%).

Solution Thermodynamics

Carbonate-free solutions of the titrant, NaOH, were prepared by dilution of 50% solution (Acros Organics) with freshly boiled MQ water under a stream of purified nitrogen gas. The solution was standardized with potassium acid phthalate and the extent of carbonate accumulation was periodically checked by titration with a standard hydrochloric acid solution and determination of the corresponding Gran titration plot.[47] Gallium ion solutions were prepared by dilution of the appropriate atomic absorption (AA) standard. The exact amount of acid present in the gallium standard was determined by titration of an equimolar solution of Ga and Na$_2$H$_2$EDTA. The amount of acid present was determined by Gran's method.[47]

Potentiometric titrations were performed using a Metrohm Titrando 809 equipped with a Ross combination pH electrode and a Metrohm Dosino 800. Data were collected in triplicate using PC Control (Version 6.0.91, Metrohm). The titration apparatus consisted of a 10 mL water jacketed glass vessel maintained at 25.0±0.1° C. (Julabo waterbath). Prior to and during the course of the titration, a blanket of nitrogen, passed through 10% NaOH to exclude any CO$_2$, was maintained over the sample solution. The ionic strength was maintained at 0.16 M using NaCl. Prior to each potentiometric equilibrium study, the electrode was calibrated using standard HCl solutions. Calibration data were analysed by standard computer treatment provided within the program MacCalib to obtain the calibration parameters E$_0$ and pKw.

As the degree of formation of Ga(III) complexes at low pH (<2) was too high for the determination of stability constants by use of direct potentiometry, the ligand-ligand competition method using Na$_2$H$_2$EDTA was also performed. Equilibrium was rapidly established (less than 10 minutes); however, up to 15 min was permitted between each titration point. The four successive proton dissociation constants corresponding to hydrolysis of Ga(III) aqueous ion included in the calculations were taken from Baes and Mesmer.[48] The protonation constants of H$_2$dedpa and stability constants of Ga(III) were calculated from the experimental data using Hyperquad 2008.

Biodistribution Data

Figure 4:
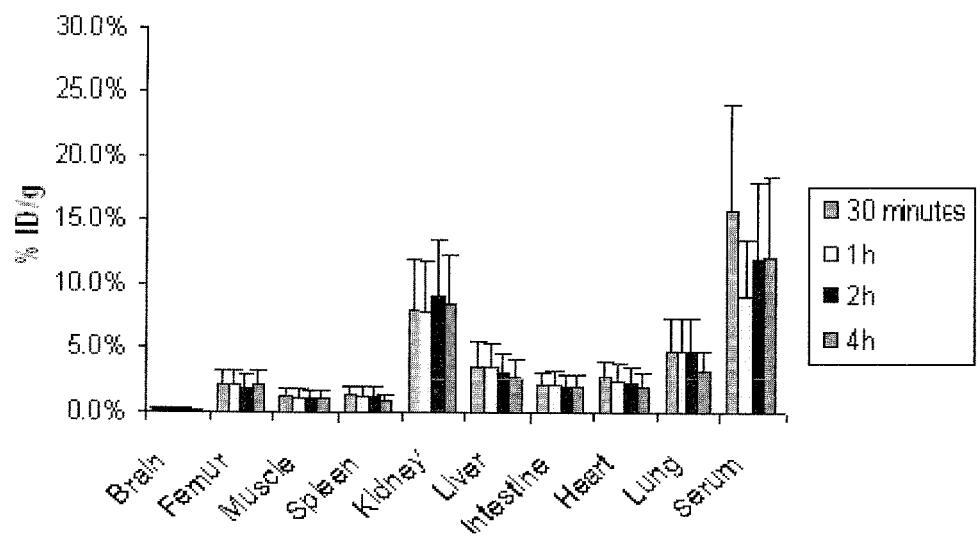
FIG. 4 illustrates biodistribution over 4 h of $^{67}$Ga(dedpa)$^+$ in female ICR mice.

The protocol used in the animal studies was approved by the Institutional Animal Care Committee of the University of British Columbia and was performed in accordance with the Canadian Council on Animal Care Guidelines. A total of 16 female ICR (20-30 g) mice were used for the animal study of each of the three compounds. $^{67}$Ga(dedpa)$^+$, $^{67}$Ga(66)$^+$, or $^{67}$Ga(69)$^+$ was prepared as described above and then diluted in phosphate buffered saline to a concentration of 100 μCi/mL. Each mouse was i.v. injected with ~10 μCi (100 μL) of the $^{67}$Ga complex and then sacrificed by CO$_2$ inhalation at 30 min, 1 h, 2 h, or 4 h after injection (n=4 at each time point). Blood was collected by cardiac puncture and plasma was separated from whole blood by centrifuging (2500 rpm, 15 min). Urine was collected from the bladder. Tissues collected included kidney, liver, spleen, femur, muscle, heart, lung, intestine and brain. Tissues were weighed and counted on a gamma counter and the counts were converted to % injected dose/gram (% ID/g). Tables 4-6 show the biodistibution data of $^{67}$Ga(dedpa)$^+$, $^{67}$Ga(66)$^+$ and $^{67}$Ga(69)$^+$, respectively, in female ICR mice. FIG. 4 illustrates biodistribution over 4 h of $^{67}$Ga(dedpa)$^+$ in female ICR mice, and FIG. 5 illustrates biodistribution of $^{67}$Ga(66)$^+$ (upper) and $^{67}$Ga(69)$^+$ (lower) in female ICR mice over 4 h; complete data for urine are shown also in separate diagrams to the right.

TABLE 4

Biodistribution data of $^{67}$Ga(dedpa)$^+$ in female ICR mice$^a$

| Organ/Tissue | 30 min ± SD | 1 h ± SD | 2 h ± SD | 4 h ± SD |
| --- | --- | --- | --- | --- |
| Brain | 0.264 ± 0.132 | 0.246 ± 0.123 | 0.213 ± 0.106 | 0.139 ± 0.069 |
| Femur | 2.180 ± 1.090 | 2.136 ± 1.068 | 1.893 ± 0.946 | 2.218 ± 1.109 |
| Muscle | 1.210 ± 0.605 | 1.153 ± 0.576 | 1.092 ± 0.546 | 1.127 ± 0.564 |
| Spleen | 1.366 ± 0.683 | 1.357 ± 0.679 | 1.273 ± 0.637 | 0.989 ± 0.495 |
| Kidney | 8.089 ± 4.009 | 7.827 ± 3.914 | 9.149 ± 4.575 | 8.301 ± 4.150 |
| Liver | 3.702 ± 1.851 | 3.695 ± 1.847 | 3.173 ± 1.586 | 2.736 ± 1.368 |
| Intestine | 2.099 ± 1.050 | 2.123 ± 1.062 | 1.995 ± 0.998 | 1.990 ± 0.995 |
| Heart | 2.645 ± 1.323 | 2.490 ± 1.245 | 2.412 ± 1.206 | 2.004 ± 1.002 |
| Lung | 4.878 ± 2.439 | 4.896 ± 2.448 | 4.846 ± 2.423 | 3.260 ± 1.630 |
| Serum | 16.067 ± 8.033 | 9.047 ± 4.524 | 12.042 ± 6.021 | 12.235 ± 6.118 |

$^a$Results are expressed as the mean ± standard deviation of % ID/g (4 animals used per time point)

TABLE 5

Biodistribution data of $^{67}$Ga(66)$^+$ in female ICR mice$^a$

| Organ/Tissue | 30 min ± SD | 1 h ± SD | 2 h ± SD | 4 h ± SD |
| --- | --- | --- | --- | --- |
| Brain | 0.163 ± 0.026 | 0.155 ± 0.017 | 0.164 ± 0.013 | 0.128 ± 0.015 |
| Femur | 1.549 ± 0.207 | 1.669 ± 0.096 | 1.971 ± 0.065 | 2.718 ± 0.884 |
| Muscle | 0.809 ± 0.073 | 0.603 ± 0.022 | 0.615 ± 0.023 | 0.578 ± 0.053 |
| Spleen | 2.328 ± 0.150 | 3.256 ± 0.274 | 3.207 ± 0.288 | 4.236 ± 0.799 |
| Kidney | 5.296 ± 0.140 | 4.190 ± 0.047 | 3.595 ± 0.401 | 4.457 ± 0.361 |
| Liver | 3.350 ± 0.576 | 3.428 ± 0.603 | 4.438 ± 0.425 | 4.511 ± 0.671 |
| Intestine | 1.706 ± 0.053 | 1.458 ± 0.123 | 1.895 ± 0.149 | 1.548 ± 0.120 |
| Heart | 1.805 ± 0.350 | 2.062 ± 0.074 | 1.887 ± 0.190 | 1.650 ± 0.224 |
| Lung | 11.188 ± 0.792 | 10.651 ± 0.560 | 8.529 ± 0.336 | 5.653 ± 0.549 |
| Blood | 5.776 ± 1.218 | 6.545 ± 0.052 | 5.904 ± 0.425 | 4.523 ± 0.462 |
| Urine | 411.147 ± 45.93 | 166.832 ± 48.91 | 47.172 ± 14.649 | 16.986 ± 3.515 |

$^a$Results are expressed as the mean ± standard deviation of % ID/g (4 animals used per time point)

TABLE 6

Biodistribution data of $^{67}$Ga(69)$^+$ in female ICR mice$^a$

| Organ/Tissue | 30 min ± SD | 1 h ± SD | 2 h ± SD | 4 h ± SD |
| --- | --- | --- | --- | --- |
| Brain | 0.162 ± 0.024 | 0.184 ± 0.020 | 0.194 ± 0.009 | 0.139 ± 0.013 |
| Femur | 1.567 ± 0.125 | 2.295 ± 0.283 | 2.610 ± 0.215 | 3.442 ± 0.088 |
| Muscle | 0.912 ± 0.056 | 1.013 ± 0.243 | 0.726 ± 0.078 | 0.705 ± 0.059 |
| Spleen | 1.223 ± 0.121 | 1.139 ± 0.101 | 1.455 ± 0.920 | 1.171 ± 0.085 |
| Kidney | 12.980 ± 0.803 | 11.044 ± 0.920 | 9.405 ± 0.137 | 10.107 ± 0.238 |
| Liver | 4.406 ± 0.255 | 3.897 ± 0.509 | 3.246 ± 0.594 | 3.634 ± 0.157 |
| Intestine | 2.042 ± 0.086 | 2.071 ± 0.271 | 1.789 ± 0.260 | 1.870 ± 0.120 |
| Heart | 2.223 ± 0.202 | 2.191 ± 0.230 | 1.918 ± 0.161 | 1.746 ± 0.154 |
| Lung | 4.303 ± 0.459 | 3.799 ± 0.299 | 3.765 ± 0.436 | 3.091 ± 0.232 |
| Blood | 7.408 ± 0.653 | 7.366 ± 0.424 | 7.430 ± 0.612 | 5.404 ± 0.415 |
| Urine | 94.710 ± 22.67 | 55.802 ± 25.633 | 33.643 ± 18.183 | 13.601 ± 3.069 |

$^a$Results are expressed as the mean ± standard deviation of % ID/g (4 animals used per time point)

X-Ray Crystallography

Data for compound Ga(dedpa)ClO$_4$ were collected with graphite-monochromated Mo—Kα radiation (0.71073 Å) at −17° C. on a Bruker X8 APEX II diffractometer. The structure was solved using direct methods using SIR-97[49] and refined using SHELXL-97.[50] All non-hydrogen atoms were refined anisotropically. All N—H hydrogen atoms were located in a difference map and refined isotropically. All other hydrogen atoms were placed in calculated positions and refined using a riding model. Data for compound Ga(7)ClO$_4$ were collected with graphite-monochromated Mo—Kα radiation at −183° C. on a Bruker APEX DUO diffractometer. The structure was solved using direct methods using SIR-97[50] and refined using SHELXL-97.[51] The material crystallizes with two crystallographically independent moieties in the asymmetric unit. One perchlorate anion is disordered and was modeled in two orientations, with restraints used to maintain reasonable geometries. Finally, MeOH solvent was found in the lattice. Two molecules of solvent were located and modeled, however one region within the asymmetric unit had residual electron density that could not be properly modeled. The SQUEEZE[51] program was used to generate a data set free of residual electron density in that region. All non-hydrogen atoms were refined anisotropically. All hydrogen atoms were placed in calculated positions and refined using a riding model. Tables 8 and 9 provide summaries of the relevant crystallographic data for both compounds.

TABLE 8

Relevant solid state crystallographic data for the complex Ga(dedpa)ClO$_4$

| | |
| --- | --- |
| Empirical Formula | C$_{16}$H$_{16}$N$_4$O$_8$GaCl |
| Formula Weight | 497.50 |

TABLE 8-continued

Relevant solid state crystallographic data for the complex Ga(dedpa)ClO$_4$

| | |
| --- | --- |
| Crystal Color, Habit | colourless, prism |
| Crystal Dimensions | 0.30 × 0.33 × 0.45 mm |
| Crystal System | triclinic |
| Lattice Type | primitive |
| Lattice Parameters | a = 7.888(1) Å |
| | b = 8.968(1) Å |
| | c = 13.264(2) Å |
| | α = 87.389(7) ° |
| | β = 77.692(8) ° |
| | γ = 85.503(7) ° |
| | V = 913.5(2) Å$^3$ |
| Space Group | P-1(#2) |
| Z value | 2 |
| D$_{calc}$ | 1.809 g/cm$^3$ |
| F$_{000}$ | 504.00 |
| Bond lengths | |
| C1O3 | 1.215(2) |
| C1O1 | 1.304(2) |
| C1C2 | 1.513(3) |
| C2N1 | 1.337(2) |
| C2C3 | 1.382(3) |
| C3C4 | 1.396(3) |
| C3H3 | 0.9500 |
| C4C5 | 1.394(3) |
| C4H4 | 0.9500 |
| C5C6 | 1.387(3) |
| C5H5 | 0.9500 |
| C6N1 | 1.332(2) |
| C6C7 | 1.510(3) |
| C7N3 | 1.486(2) |
| C7H7A | 0.9900 |
| C7H7B | 0.9900 |
| C8N3 | 1.486(2) |

TABLE 8-continued

Relevant solid state crystallographic data for the complex Ga(dedpa)ClO$_4$

| | |
|---|---|
| C8C9 | 1.512(3) |
| C8H8A | 0.9900 |
| C8H8B | 0.9900 |
| C9N4 | 1.483(2) |
| C9H9A | 0.9900 |
| C10N4 | 1.479(2) |
| C10C11 | 1.514(2) |
| C10H10A | 0.9900 |
| C10H10B | 0.9900 |
| C11N2 | 1.332(2) |
| C11C12 | 1.386(3) |
| C12C13 | 1.394(3) |
| C12H12 | 0.9500 |
| C13C14 | 1.398(3) |
| C13H13 | 0.9500 |
| C14C15 | 1.372(3) |
| C14H14 | 0.9500 |
| C15N2 | 1.338(2) |
| C15C16 | 1.522(2) |
| C16O4 | 1.225(2) |
| C16O2 | 1.287(2) |
| N1Ga1 | 1.9866(16) |
| N2Ga1 | 1.9902(16) |
| N3Ga1 | 2.1115(16) |
| N3H3N | 0.86(3) |
| N4Ga1 | 2.1132(16) |
| N4H4N | 0.78(3) |
| O1Ga1 | 1.9708(13) |
| O2Ga1 | 1.9828(13) |
| O5Cl1 | 1.4443(16) |
| O6Cl1 | 1.4353(14) |
| O7Cl1 | 1.4369(16) |
| O8Cl1 | 1.4371(16) |
| Bond angles | |
| O3C1O1 | 125.45(17) |
| O3C1C2 | 120.78(17) |
| O1C1C2 | 113.77(15) |
| N1C2C3 | 120.43(17) |
| N1C2C1 | 112.34(16) |
| C3C2C1 | 127.24(17) |
| C2C3C4 | 117.75(17) |
| C2C3H3 | 121.1 |
| C4C3H3 | 121.1 |
| C5C4C3 | 120.64(17) |
| C5C4H4 | 119.7 |
| C3C4H4 | 119.7 |
| C6C5C4 | 118.44(17) |
| C6C5H5 | 120.8 |
| C4C5H5 | 120.8 |
| N1C6C5 | 119.60(17) |
| N1C6C7 | 113.73(16) |
| C5C6C7 | 126.66(17) |
| N3C7C6 | 108.98(14) |
| N3C7H7A | 109.9 |
| C6C7H7A | 109.9 |
| N3C7H7B | 109.9 |
| C6C7H7B | 109.9 |
| H7AC7H7B | 108.3 |
| N3C8C9 | 108.02(15) |
| N3C8H8A | 110.1 |
| C9C8H8A | 110.1 |
| N3C8H8B | 110.1 |
| C9C8H8B | 110.1 |
| H8AC8H8B | 108.4 |
| N4C9C8 | 107.99(15) |
| N4C9H9A | 110.1 |
| C8C9H9A | 110.1 |
| N4C9H9B | 110.1 |
| C8C9H9B | 110.1 |
| H9AC9H9B | 108.4 |
| N4C10C11 | 109.56(14) |
| N4C10H10A | 109.8 |
| C11C10H10A | 109.8 |
| N4C10H10B | 109.8 |
| C11C10H10B | 109.8 |
| H10AC10H10B | 108.2 |

TABLE 8-continued

Relevant solid state crystallographic data for the complex Ga(dedpa)ClO$_4$

| | |
|---|---|
| N2C11C12 | 120.01(17) |
| N2C11C10 | 113.52(16) |
| C12C11C10 | 126.39(16) |
| C11C12C13 | 118.26(17) |
| C11C12H12 | 120.9 |
| C13C12H12 | 120.9 |
| C12C13C14 | 120.29(18) |
| C12C13H13 | 119.9 |
| C14C13H13 | 119.9 |
| C15C14C13 | 118.20(17) |
| C15C14H14 | 120.9 |
| C13C14H14 | 120.9 |
| N2C15C14 | 120.51(16) |
| N2C15C16 | 111.93(15) |
| C14C15C16 | 127.53(16) |
| O4C16O2 | 125.76(17) |
| O4C16C15 | 120.34(16) |
| O2C16C15 | 113.89(15) |
| C6N1C2 | 123.14(16) |
| C6N1Ga1 | 120.49(13) |
| C2N1Ga1 | 116.29(12) |
| C11N2C15 | 122.70(16) |
| C11N2Ga1 | 120.49(13) |
| C15N2Ga1 | 116.65(12) |
| C7N3C8 | 111.45(15) |
| C7N3Ga1 | 109.91(11) |
| C8N3Ga1 | 106.27(11) |
| C7N3H3N | 107.5(17) |
| C8N3H3N | 107.5(17) |
| Ga1N3H3N | 114.2(18) |
| C10N4C9 | 111.66(15) |
| C10N4Ga1 | 109.90(11) |
| C9N4Ga1 | 106.84(11) |
| C10N4H4N | 108.8(19) |
| C9N4H4N | 109.4(19) |
| Ga1N4H4N | 110.2(19) |
| C1O1Ga1 | 117.41(11) |
| C16O2Ga1 | 117.85(12) |
| O6Cl1O7 | 110.02(10) |
| O6Cl1O8 | 109.75(10) |
| O7Cl1O8 | 109.60(11) |
| O6Cl1O5 | 109.62(10) |
| O7Cl1O5 | 109.01(10) |
| O8Cl1O5 | 108.81(11) |
| O1Ga1O2 | 101.39(6) |
| O1Ga1N1 | 80.14(6) |
| O2Ga1N1 | 94.02(6) |
| O1Ga1N2 | 94.72(6) |
| O2Ga1N2 | 79.63(6) |
| N1Ga1N2 | 170.97(6) |
| O1Ga1N3 | 153.44(6) |
| O2Ga1N3 | 94.78(6) |
| N1Ga1N3 | 77.82(6) |
| N2Ga1N3 | 108.92(6) |
| O1Ga1N4 | 90.32(6) |
| O2Ga1N4 | 155.63(6) |
| N1Ga1N4 | 109.11(6) |
| N2Ga1N4 | 78.15 |

TABLE 9

Relevant solid state crystallographic data for the complex Ga(66)ClO$_4$

| | |
|---|---|
| Empirical Formula | $C_{31}H_{30}N_6O_{13}GaCl$ |
| Formula Weight | 799.78 |
| Crystal Colour, Habit | colourless, plate |
| Crystal Dimensions | 0.02 × 0.35 × 0.60 mm |
| Crystal System | monoclinic |

TABLE 9-continued

Relevant solid state crystallographic data for the complex Ga(66)ClO$_4$

| | | |
|---|---|---|
| Lattice Type | primitive | |
| Lattice Parameters | a = 20.317(2) Å | |
| | b = 14.030(2) Å | |
| | c = 24.060(3) Å | |
| | α = 90° | |
| | β = 98.966(2) ° | |
| | γ = 90° | |
| | V = 993.9(5) Å$^3$ | |
| Space Group | P2$_1$/c (#14) | |
| Z value | 8 | |
| D$_{calc}$ | 1.568 g/cm$^3$ | |
| F$_{000}$ | 3280.00 | |
| Bond lengths | | |
| C1O3 | 1.221(7) | |
| C1O1 | 1.312(7) | |
| C1C2 | 1.493(9) | |
| C2N1 | 1.348(7) | |
| C2C3 | 1.381(8) | |
| C3C4 | 1.384(9) | |
| C3H3 | 0.9500 | |
| C4C5 | 1.389(9) | |
| C4H4 | 0.9500 | |
| C5C6 | 1.392(8) | |
| C5H5 | 0.9500 | |
| C6N1 | 1.319(7) | |
| C6C7 | 1.504(8) | |
| C7N3 | 1.494(7) | |
| C7H7A | 0.9900 | |
| C7H7B | 0.9900 | |
| C8N3 | 1.492(7) | |
| C8C9 | 1.515(8) | |
| C8H8A | 0.9900 | |
| C8H8B | 0.9900 | |
| C9N4 | 1.500(7) | |
| C9H9A | 0.9900 | |
| C9H9B | 0.9900 | |
| C10N4 | 1.483(7) | |
| C10C11 | 1.486(8) | |
| C10H10A | 0.9900 | |
| C10H10B | 0.9900 | |
| C11N2 | 1.329(7) | |
| C11C12 | 1.387(8) | |
| C12C13 | 1.367(9) | |
| C12H12 | 0.9500 | |
| C13C14 | 1.365(9) | |
| C13H13 | 0.9500 | |
| C14C15 | 1.360(9) | |
| C14H14 | 0.9500 | |
| C15N2 | 1.344(8) | |
| C15C16 | 1.539(8) | |
| C16O4 | 1.220(8) | |
| C16O2 | 1.287(8) | |
| C17C18 | 1.501(8) | |
| C17N3 | 1.517(7) | |
| C17H17A | 0.9900 | |
| C17H17B | 0.9900 | |
| C18C23 | 1.397(8) | |
| C18C19 | 1.408(8) | |
| C19C20 | 1.368(9) | |
| C19H19 | 0.9500 | |
| C20C21 | 1.397(8) | |
| C20H20 | 0.9500 | |
| C21C22 | 1.386(8) | |
| C21N5 | 1.456(8) | |
| C22C23 | 1.369(9) | |
| C22H22 | 0.9500 | |
| C23H23 | 0.9500 | |
| C24N4 | 1.511(7) | |
| C24C25 | 1.527(8) | |
| C24H24A | 0.9900 | |
| C24H24B | 0.9900 | |
| C25C26 | 1.367(9) | |
| C25C30 | 1.398(9) | |
| C26C27 | 1.376(8) | |
| C26H26 | 0.9500 | |
| C27C28 | 1.384(10) | |
| C27H27 | 0.9500 | |
| C28C29 | 1.361(11) | |
| C28N6 | 1.473(9) | |
| C29C30 | 1.383(10) | |
| C29H29 | 0.9500 | |
| C30H30 | 0.9500 | |
| C31O15 | 1.214(7) | |
| C31O13 | 1.280(7) | |
| C31C32 | 1.517(9) | |
| C32N7 | 1.348(7) | |
| C32C33 | 1.365(9) | |
| C33C34 | 1.400(10) | |
| C33H33 | 0.9500 | |
| C34C35 | 1.402(9) | |
| C34H34 | 0.9500 | |
| C35C36 | 1.371(9) | |
| C35H35 | 0.9500 | |
| C36N7 | 1.333(7) | |
| C36C37 | 1.513(9) | |
| C37N9 | 1.507(8) | |
| C37H37A | 0.9900 | |
| C37H37B | 0.9900 | |
| C38N9 | 1.489(7) | |
| C38C39 | 1.511(8) | |
| C38H38A | 0.9900 | |
| C38H38B | 0.9900 | |
| C39N10 | 1.508(7) | |
| C39H39A | 0.9900 | |
| C39H39B | 0.9900 | |
| C40N10 | 1.479(7) | |
| C40C41 | 1.518(8) | |
| C40H40A | 0.9900 | |
| C40H40B | 0.9900 | |
| C41N8 | 1.320(7) | |
| C41C42 | 1.389(8) | |
| C42C43 | 1.399(8) | |
| C42H42 | 0.9500 | |
| C43C44 | 1.361(8) | |
| C43H43 | 0.9500 | |
| C44C45 | 1.400(8) | |
| C44H44 | 0.9500 | |
| C45N8 | 1.354(7) | |
| C45C46 | 1.494(9) | |
| C46O16 | 1.214(7) | |
| C46O14 | 1.294(7) | |
| C47C48 | 1.513(8) | |
| C47N9 | 1.522(7) | |
| C47H47A | 0.9900 | |
| C47H47B | 0.9900 | |
| C48C53 | 1.364(9) | |
| C48C49 | 1.404(8) | |
| C49C50 | 1.384(9) | |
| C49H49 | 0.9500 | |
| C50C51 | 1.358(9) | |
| C50H50 | 0.9500 | |
| C51C52 | 1.377(8) | |
| C51N11 | 1.491(8) | |
| C52C53 | 1.390(8) | |
| C52H52 | 0.9500 | |
| C53H53 | 0.9500 | |
| C54C55 | 1.505(8) | |
| C54N10 | 1.529(7) | |
| C54H54A | 0.9900 | |
| C54H54B | 0.9900 | |
| C55C56 | 1.374(8) | |
| C55C60 | 1.394(8) | |
| C56C57 | 1.402(8) | |
| C56H56 | 0.9500 | |
| C57C58 | 1.373(9) | |
| C57H57 | 0.9500 | |
| C58C59 | 1.360(9) | |
| C58N12 | 1.493(8) | |
| C59C60 | 1.378(8) | |
| C59H59 | 0.9500 | |
| C60H60 | 0.9500 | |
| C62O26 | 1.402(13) | |
| C62H62A | 0.9800 | |
| C62H62B | 0.9800 | |
| C62H62C | 0.9800 | |

TABLE 9-continued

Relevant solid state crystallographic data for the complex Ga(66)ClO$_4$

| | |
|---|---|
| C63O27 | 1.307(10) |
| C63H63A | 0.9800 |
| C63H63B | 0.9800 |
| C63H63C | 0.9800 |
| N1Ga1 | 1.992(5) |
| N2Ga1 | 1.981(5) |
| N3Ga1 | 2.188(5) |
| N4Ga1 | 2.159(5) |
| N5O5 | 1.225(6) |
| N5O6 | 1.231(6) |
| N6O8 | 1.224(9) |
| N6O7 | 1.224(9) |
| N7Ga2 | 1.974(5) |
| N8Ga2 | 1.971(5) |
| N9Ga2 | 2.144(5) |
| N10Ga2 | 2.180(5) |
| N11O18 | 1.209(7) |
| N11O17 | 1.223(6) |
| N12O19 | 1.216(7) |
| N12O20 | 1.256(7) |
| O1Ga1 | 1.967(4) |
| O2Ga1 | 1.976(4) |
| O9Cl1 | 1.417(5) |
| O10Cl1 | 1.461(5) |
| O11Cl1 | 1.411(7) |
| O12Cl1 | 1.400(5) |
| O13Ga2 | 1.964(4) |
| O14Ga2 | 1.964(4) |
| O21Cl2 | 1.447(5) |
| O22Cl2B | 1.233(8) |
| O22Cl2 | 1.507(5) |
| O23Cl2 | 1.453(5) |
| O24Cl2 | 1.479(5) |
| O26H26A | 0.8400 |
| O27H27A | 0.8400 |
| Cl2BO24B | 1.244(10) |
| Cl2BO21B | 1.261(10) |
| Cl2BO23B | 1.266(10) |
| Bond angles | |
| O3C1O1 | 123.8(6) |
| O3C1C2 | 122.0(6) |
| O1C1C2 | 114.1(6) |
| N1C2C3 | 120.0(6) |
| N1C2C1 | 113.1(5) |
| C3C2C1 | 126.8(6) |
| C2C3C4 | 117.9(6) |
| C2C3H3 | 121.1 |
| C4C3H3 | 121.1 |
| C3C4C5 | 121.0(6) |
| C3C4H4 | 119.5 |
| C5C4H4 | 119.5 |
| C4C5C6 | 118.4(6) |
| C4C5H5 | 120.8 |
| C6C5H5 | 120.8 |
| N1C6C5 | 119.5(5) |
| N1C6C7 | 114.4(5) |
| C5C6C7 | 125.8(6) |
| N3C7C6 | 110.6(5) |
| N3C7H7A | 109.5 |
| C6C7H7A | 109.5 |
| N3C7H7B | 109.5 |
| C6C7H7B | 109.5 |
| H7AC7H7B | 108.1 |
| N3C8C9 | 109.7(5) |
| N3C8H8A | 109.7 |
| C9C8H8A | 109.7 |
| N3C8H8B | 109.7 |
| C9C8H8B | 109.7 |
| H8AC8H8B | 108.2 |
| N4C9C8 | 109.7(4) |
| N4C9H9A | 109.7 |
| C8C9H9A | 109.7 |
| N4C9H9B | 109.7 |
| C8C9H9B | 109.7 |
| H9AC9H9B | 108.2 |
| N4C10C11 | 110.4(5) |
| N4C10H10A | 109.6 |
| C11C10H10A | 109.6 |
| N4C10H10B | 109.6 |
| C11C10H10B | 109.6 |
| H10AC10H10B | 108.1 |
| N2C11C12 | 119.5(6) |
| N2C11C10 | 113.6(5) |
| C12C11C10 | 126.9(5) |
| C13C12C11 | 118.5(6) |
| C13C12H12 | 120.8 |
| C11C12H12 | 120.8 |
| C14C13C12 | 120.9(7) |
| C14C13H13 | 119.6 |
| C12C13H13 | 119.6 |
| C15C14C13 | 119.0(7) |
| C15C14H14 | 120.5 |
| C13C14H14 | 120.5 |
| N2C15C14 | 120.0(6) |
| N2C15C16 | 111.6(6) |
| C14C15C16 | 128.5(6) |
| O4C16O2 | 126.8(6) |
| O4C16C15 | 119.3(6) |
| O2C16C15 | 113.9(6) |
| C18C17N3 | 115.4(5) |
| C18C17H17A | 108.4 |
| N3C17H17A | 108.4 |
| C18C17H17B | 108.4 |
| N3C17H17B | 108.4 |
| H17AC17H17B | 107.5 |
| C23C18C19 | 118.6(6) |
| C23C18C17 | 121.7(5) |
| C19C18C17 | 119.6(5) |
| C20C19C18 | 120.3(5) |
| C20C19H19 | 119.8 |
| C18C19H19 | 119.8 |
| C19C20C21 | 119.8(5) |
| C19C20H20 | 120.1 |
| C21C20H20 | 120.1 |
| C22C21C20 | 120.6(6) |
| C22C21N5 | 120.3(5) |
| C20C21N5 | 119.1(5) |
| C23C22C21 | 119.4(5) |
| C23C22H22 | 120.3 |
| C21C22H22 | 120.3 |
| C22C23C18 | 121.2(5) |
| C22C23H23 | 119.4 |
| C18C23H23 | 119.4 |
| N4C24C25 | 114.1(4) |
| N4C24H24A | 108.7 |
| C25C24H24A | 108.7 |
| N4C24H24B | 108.7 |
| C25C24H24B | 108.7 |
| H24AC24H24B | 107.6 |
| C26C25C30 | 118.1(6) |
| C26C25C24 | 122.1(6) |
| C30C25C24 | 119.8(6) |
| C25C26C27 | 123.5(6) |
| C25C26H26 | 118.3 |
| C27C26H26 | 118.3 |
| C26C27C28 | 116.4(7) |
| C26C27H27 | 121.8 |
| C28C27H27 | 121.8 |
| C29C28C27 | 122.8(6) |
| C29C28N6 | 119.0(8) |
| C27C28N6 | 118.2(8) |
| C28C29C30 | 119.2(7) |
| C28C29H29 | 120.4 |
| C30C29H29 | 120.4 |
| C29C30C25 | 120.0(7) |
| C29C30H30 | 120.0 |
| C25C30H30 | 120.0 |
| O15C31O13 | 126.0(6) |
| O15C31C32 | 119.5(6) |
| O13C31C32 | 114.5(5) |
| N7C32C33 | 119.7(6) |
| N7C32C31 | 112.3(5) |
| C33C32C31 | 128.0(6) |
| C32C33C34 | 118.4(7) |
| C32C33H33 | 120.8 |

TABLE 9-continued

Relevant solid state crystallographic data for the complex Ga(66)ClO$_4$

| | |
|---|---|
| C34C33H33 | 120.8 |
| C33C34C35 | 120.6(7) |
| C33C34H34 | 119.7 |
| C35C34H34 | 119.7 |
| C36C35C34 | 118.0(6) |
| C36C35H35 | 121.0 |
| C34C35H35 | 121.0 |
| N7C36C35 | 120.1(6) |
| N7C36C37 | 113.8(5) |
| C35C36C37 | 125.9(6) |
| N9C37C36 | 111.4(5) |
| N9C37H37A | 109.4 |
| C36C37H37A | 109.4 |
| N9C37H37B | 109.4 |
| C36C37H37B | 109.4 |
| H37AC37H37B | 108.0 |
| N9C38C39 | 110.2(5) |
| N9C38H38A | 109.6 |
| C39C38H38A | 109 |
| N9C38H38B | 109.6 |
| C39C38H38B | 109.6 |
| H38AC38H38B | 108.1 |
| N10C39C38 | 109.5(5) |
| N10C39H39A | 109.8 |
| C38C39H39A | 109.8 |
| N10C39H39B | 109.8 |
| C38C39H39B | 109.8 |
| H39AC39H39B | 108.2 |
| N10C40C41 | 111.1(4) |
| N10C40H40A | 109.4 |
| C41C40H40A | 109.4 |
| N10C40H40B | 109.4 |
| C41C40H40B | 109.4 |
| H40AC40H40B | 108.0 |
| N8C41C42 | 120.1(5) |
| N8C41C40 | 113.9(5) |
| C42C41C40 | 125.9(5) |
| C41C42C43 | 118.5(6) |
| C41C42H42 | 120.8 |
| C43C42H42 | 120.8 |
| C44C43C42 | 120.1(6) |
| C44C43H43 | 119.9 |
| C42C43H43 | 119.9 |
| C43C44C45 | 119.7(5) |
| C43C44H44 | 120.2 |
| C45C44H44 | 120.2 |
| N8C45C44 | 118.4(5) |
| N8C45C46 | 112.9(6) |
| C44C45C46 | 128.6(5) |
| O16C46O14 | 125.0(6) |
| O16C46C45 | 120.2(6) |
| O14C46C45 | 114.8(5) |
| C48C47N9 | 114.4(5) |
| C48C47H47A | 108.6 |
| N9C47H47A | 108.6 |
| C48C47H47B | 108.6 |
| N9C47H47B | 108.6 |
| H47AC47H47B | 107.6 |
| C53C48C49 | 118.8(6) |
| C53C48C47 | 119.7(5) |
| C49C48C47 | 121.5(6) |
| C50C49C48 | 120.7(6) |
| C50C49H49 | 119.7 |
| C48C49H49 | 119.7 |
| C51C50C49 | 118.5(5) |
| C51C50H50 | 120.8 |
| C49C50H50 | 120.8 |
| C50C51C52 | 122.7(6) |
| C50C51N11 | 118.3(5) |
| C52C51N11 | 118.9(6) |
| C51C52C53 | 118.2(6) |
| C51C52H52 | 120.9 |
| C53C52H52 | 120.9 |
| C48C53C52 | 121.2(5) |
| C48C53H53 | 119.4 |
| C52C53H53 | 119.4 |
| C55C54N10 | 113.7(5) |
| C55C54H54A | 108.8 |
| N10C54H54A | 108.8 |
| C55C54H54B | 108.8 |
| N10C54H54B | 108.8 |
| H54AC54H54B | 107.7 |
| C56C55C60 | 118.2(6) |
| C56C55C54 | 121.8(5) |
| C60C55C54 | 120.0(6) |
| C55C56C57 | 121.8(6) |
| C55C56H56 | 119.1 |
| C57C56H56 | 119.1 |
| C58C57C56 | 116.7(6) |
| C58C57H57 | 121.7 |
| C56C57H57 | 121.7 |
| C59C58C57 | 123.9(6) |
| C59C58N12 | 119.2(6) |
| C57C58N12 | 116.9(6) |
| C58C59C60 | 117.9(6) |
| C58C59H59 | 121.0 |
| C60C59H59 | 121.0 |
| C59C60C55 | 121.5(6) |
| C59C60H60 | 119.2 |
| C55C60H60 | 119.2 |
| O26C62H62A | 109.5 |
| O26C62H62B | 109.5 |
| H62AC62H62B | 109.5 |
| O26C62H62C | 109.5 |
| H62AC62H62C | 109.5 |
| H62BC62H62C | 109.5 |
| O27C63H63A | 109.5 |
| O27C63H63B | 109.5 |
| H63AC63H63B | 109.5 |
| O27C63H63C | 109.5 |
| H63AC63H63C | 109.5 |
| H63BC63H63C | 109.5 |
| C6N1C2 | 123.2(5) |
| C6N1Ga1 | 121.7(4) |
| C2N1Ga1 | 115.1(4) |
| C11N2C15 | 121.9(5) |
| C11N2Ga1 | 121.1(4) |
| C15N2Ga1 | 116.4(4) |
| C8N3C7 | 110.1(4) |
| C8N3C17 | 111.6(4) |
| C7N3C17 | 109.3(4) |
| C8N3Ga1 | 104.7(3) |
| C7N3Ga1 | 108.1(3) |
| C17N3Ga1 | 112.9(3) |
| C10N4C9 | 110.2(4) |
| C10N4C24 | 109.7(4) |
| C9N4C24 | 112.9(5) |
| C10N4Ga1 | 107.6(3) |
| C9N4Ga1 | 102.8(3) |
| C24N4Ga1 | 113.4(3) |
| O5N5O6 | 122.5(5) |
| O5N5C21 | 119.1(5) |
| O6N5C21 | 118.4(5) |
| O8N6O7 | 123.0(7) |
| O8N6C28 | 118.7(8) |
| O7N6C28 | 118.3(9) |
| C36N7C32 | 123.3(6) |
| C36N7Ga2 | 120.8(4) |
| C32N7Ga2 | 114.8(4) |
| C41N8C45 | 123.1(5) |
| C41N8Ga2 | 121.7(4) |
| C45N8Ga2 | 114.7(4) |
| C38N9C37 | 110.4(5) |
| C38N9C47 | 111.8(4) |
| C37N9C47 | 110.3(4) |
| C38N9Ga2 | 103.8(3) |
| C37N9Ga2 | 108.0(4) |
| C47N9Ga2 | 112.4(3) |
| C40N10C39 | 110.4(5) |
| C40N10C54 | 110.4(4) |
| C39N10C54 | 110.9(4) |
| C40N10Ga2 | 107.9(3) |
| C39N10Ga2 | 102.5(3) |
| C54N10Ga2 | 114.4(4) |
| O18N11O17 | 125.1(6) |
| O18N11C51 | 117.0(5) |

TABLE 9-continued

Relevant solid state crystallographic data for the complex Ga(66)ClO$_4$

| | |
|---|---|
| O17N11C51 | 117.8(6) |
| O19N12O20 | 124.7(6) |
| O19N12C58 | 119.5(6) |
| O20N12C58 | 115.8(6) |
| C1O1Ga1 | 116.7(4) |
| C16O2Ga1 | 117.4(4) |
| C31O13Ga2 | 116.8(4) |
| C46O14Ga2 | 116.3(4) |
| Cl2BO22Cl2 | 46.8(5) |
| C62O26H26A | 109.5 |
| C63O27H27A | 109.5 |
| O12Cl1O11 | 111.6(5) |
| O12Cl1O9 | 109.1(3) |
| O11Cl1O9 | 111.8(5) |
| O12Cl1O10 | 110.0(4) |
| O11Cl1O10 | 106.3(4) |
| O9Cl1O10 | 107.9(3) |
| O21Cl2O23 | 111.4(4) |
| O21Cl2O24 | 109.7(3) |
| O23Cl2O24 | 108.9(3) |
| O21Cl2O22 | 109.5(3) |
| O23Cl2O22 | 109.8(3) |
| O24Cl2O22 | 107.4(4) |
| O1Ga1O2 | 97.24(17) |
| O1Ga1N2 | 92.85(19) |
| O2Ga1N2 | 80.46(19) |
| O1Ga1N1 | 80.62(19) |
| O2Ga1N1 | 98.44(18) |
| N2Ga1N1 | 173.2(2) |
| O1Ga1N4 | 94.45(17) |
| O2Ga1N4 | 155.36(17) |
| N2Ga1N4 | 77.35(19) |
| N1Ga1N4 | 104.84(18) |
| O1Ga1N3 | 157.48(18) |
| O2Ga1N3 | 93.00(18) |
| N2Ga1N3 | 108.64(18) |
| N1Ga1N3 | 78.06(18) |
| N4Ga1N3 | 84.13(17) |
| O14Ga2O13 | 100.74(17) |
| O14Ga2N8 | 81.29(18) |
| O13Ga2N8 | 93.45(18) |
| O14Ga2N7 | 93.50(18) |
| O13Ga2N7 | 81.14(18) |
| N8Ga2N7 | 171.7(2) |
| O14Ga2N9 | 92.44(17) |
| O13Ga2N9 | 156.88(18) |
| N8Ga2N9 | 107.37(18) |
| N7Ga2N9 | 79.15(19) |
| O14Ga2N10 | 157.45(18) |
| O13Ga2N10 | 89.67(17) |
| N8Ga2N10 | 78.13(18) |
| N7Ga2N10 | 107.94(18) |
| N9Ga2N10 | 85.03(17) |
| O22Cl2BO24B | 112.8(6) |
| O22Cl2BO21B | 108.7(6) |
| O24BCl2BO21B | 109.6(6) |
| O22Cl2BO23B | 108.5(6) |
| O24BCl2BO23B | 108.8(6) |
| O21BCl2BO23B | 108.3(6) |

Figure 3:
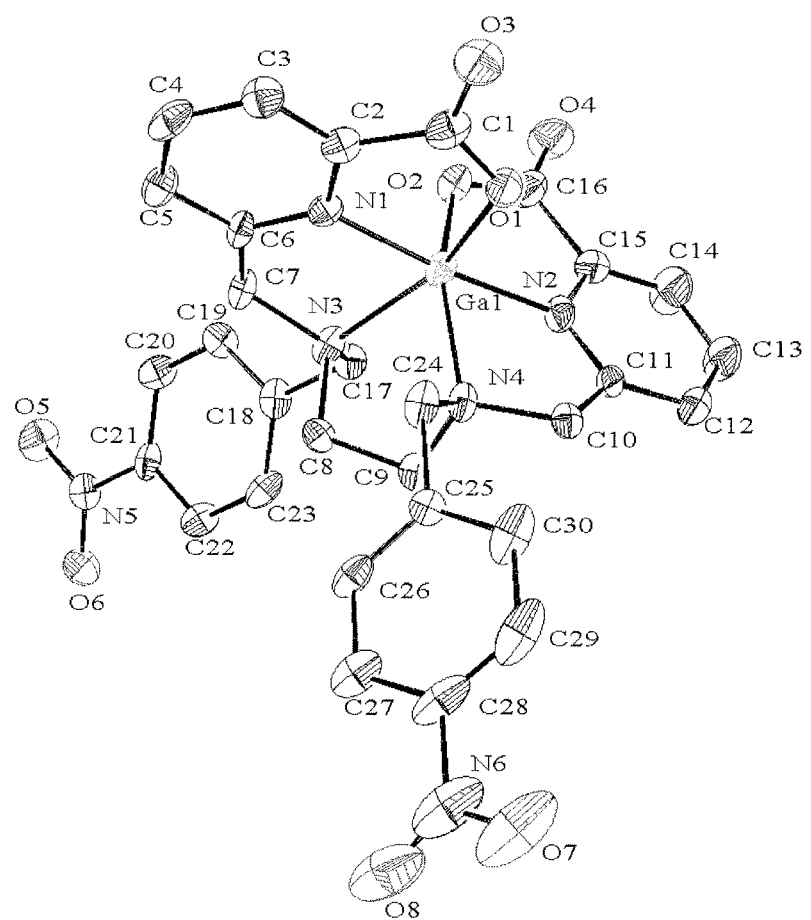
FIG. 3 illustrates the solid-state structure of the cation in Ga(66)ClO$_4$.

FIG. 3 illustrates the solid state structure of the cation in Ga(66)ClO$_4$ (relevant bond lengths Å: N1-Ga.: 1.992(5); N2-Ga: 1.981(5); N3-Ga: 2.188(5); N4-Ga: 2.159(5); O1-Ga: 1.967(4); O2-Ga: 1.976(4)).

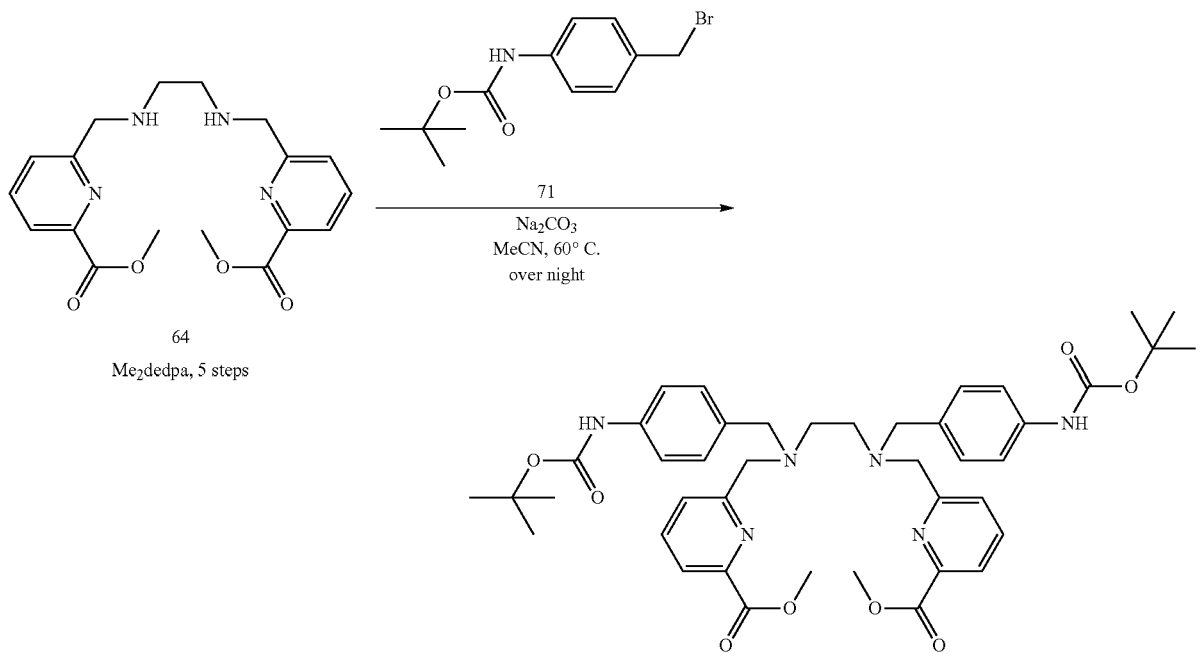

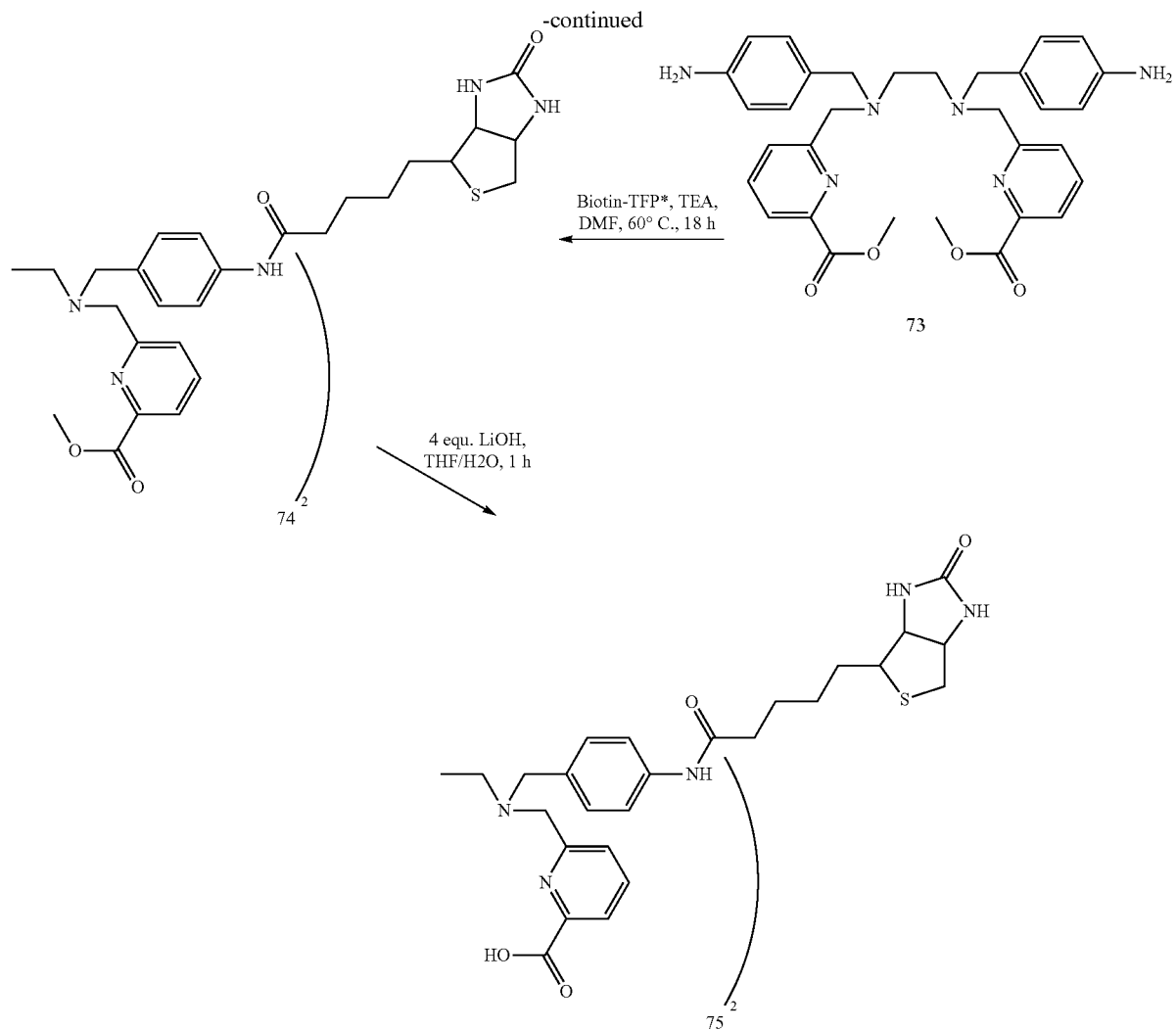

72

1,2-{6-(Methoxycarbonyl)pyridin-2-yl}methylaminoethane (23 mg, 0.064 mmol) and 2.1 equivalents of (4-Bromomethyl-phenyl)-carbamic acid tert-butyl ester (38 mg, 0.135 mmol) were dissolved in acetonitrile. $Na_2CO_3$ (400 mg) was added into the reaction mixture and the reaction was stirred at 60° C. over night. The resulting milky solution was filtered and the solvent was removed in vacuo to afford the crude as an oil. This was then subsequently purified by column chromatography (10% MeOH in DCM) to afford 72 as a very viscous, colorless oil.

Yield: 0.019 g, 0.024 mmol, 38% $R_f$: 0.5

$^1$H NMR ($CDCl_3$, 400 MHz): 7.97 (d, 2H, py-H), 7.70 (m, 4H, py-H), 7.24-7.14 (m, 8H, bn-H), 6.58 (s, 2H, CO—NH), 3.98 (s, 6H, $CH_3$), 3.81 (s, 4H, N—$CH_2$), 3.49 (s, 4H, N—$CH_2$), 2.62 (s, 4H, $CH_2$—$CH_2$), 1.52 (s, 18H, $^t$Bu—H)

$^{13}$C NMR ($CDCl_3$, 75 MHz): 163.1, 161.5, 158.3, 153.0, 147.3, 137.5, 129.5, 118.8, 58.7, 53.6, 53.1, 28.6

HR-ESI-MS: m/z calcd for $C_{42}H_{52}N_6O_8Na$: 791.3744. found: 791.3730 M+Na$^+$ Elemental Analysis: N, 10.31; C, 64.49; H, 6.73 (calcd. N, 10.53; C, 64.74; H, 6.65 for 1.MeOH)

73

72 (0.02 g, 0.026 mmol) was dissolved in 2 mL DCM. 0.5 mL TFA was added and the reaction mixture was stirred for 1 h, when reaction was found to be complete according to TLC. The acid was then quenched with saturated $NaHCO_3$ (20 mL) and the aqueous solution was then extracted twice with EtOAc (20 mL) and twice with DCM (20 mL). All organic fractions were collected and dried with $MgSO_4$. The solvent was removed in vacuo to subsequently afford the free amine 73 as a yellow oil which was immediately used in the follow-up reaction.

Yield: 0.003 g, 0.005 mmol, 22% $R_f$: 0.1

$^1$H NMR ($CDCl_3$, 400 MHz): 7.98 (d, 2H, py-H), 7.71 (m, 4H, py-H), 7.06-6.59 (m, 8H, bn-H), 4.02 (s, 6H, $CH_3$), 3.81 (s, 4H, N—$CH_2$), 3.47 (s, 4H, N—$CH_2$), 2.65 (s, 4H, $CH_2$—$CH_2$)

HR-ESI-MS: m/z calcd for $C_{32}H_{37}N_6O_4$: 569.2869. found: 569.2869 M+H$^+$

74

73 (0.048 g, 0.084 mmol) was dissolved in DMF (5 mL), together with Biotin-TFP (0.076 g, 0.19 mmol, 2 equ.) and $NEt_3$ (73 µL) and stirred at 55° C. for 20 h. Subsequently, the solvent was removed to afford a glassy solid which was purified with column chromatography ($Al_2O_3$, 10% MeOH in DCM) to afford the dialkylated product 74 as a white solid.

Yield: 0.009 g, 0.009 mmol, 10% $R_f$: 0.5 ($Al_2O_3$, 10% MeOH in DCM)

¹H NMR (DMSO-d₆, 400 MHz): 9.80 (s, 2H, CO—NH), 7.87 (m, 4H, py-H), 7.62 (d, 2H, py-H), 7.47 (d, 4H, bz-H), 7.16 (d, 2H, bn-H), 6.42-6.35 (d, 4H, CO—NH), 4.29 (m, 2H), 4.06 (m, 2H), 3.85 (s, 6H, CH₃), 3.65 (s, 4H, N—CH₂), 3.45 (s, 4H, N—CH₂), 3.16 (m, 4H), 2.83-2.79 (m, 6H), 2.56 (m, 5H, CH₂—CH₂), 2.28 (m, 2H), 1.63-1.23 (m, 10H).

¹³C NMR (DMSO-d₆, 75 MHz): 171.0, 162.7, 160.3, 138.1, 137.7, 133.3, 129.0, 126.0, 123.2, 118.8, 61.0, 59.2, 57.7, 55.4, 54.9, 52.4, 50.8, 40.0, 36.2, 28.3, 28.1, 25.2

HR-ESI-MS: m/z calcd for $C_{52}H_{65}N_{10}O_8{}^{32}S$: 1021.4428. found: 1021.4451 M+H⁺

75

74 (0.007 g, 0.007 mmol) was dissolved in a 1:3 mixture of MeOH and H₂O. LiOH (1 mg, 0.041 mmol, 6 equ.) was added to the solution and stirred at room temperature for 2 h. The reaction was found to be complete after 2 h according to TLC. Subsequently, the solvent was removed to afford 75 as a white solid.

Yield: 0.006 g, 0.006 mmol, 85% $R_f$: 0.15

¹H NMR (DMSO-d₆, 400 MHz): 9.83 (s, 2H, CO—NH), 7.87 (m, 4H, py-H), 7.47 (d, 4H, bz-H), 7.33 (d, 2H, py-H), 7.06 (d, 2H, bn-H), 6.43-6.34 (d, 4H, CO—NH), 4.30 (m, 2H), 4.19 (m, 2H), 3.59 (s, 4H, N—CH₂), 3.38 (s, 4H, N—CH₂), 3.24 (m, 4H), 2.83-2.81 (m, 6H), 2.57 (m, 2H), 2.30-2.23 (m, 5H, CH₂—CH₂), 1.62-1.29 (m, 10H).

¹³C NMR (DMSO-d₆, 75 MHz): 171.0, 167.6, 162.8, 157.5, 155.8, 138.2, 137.9, 131.8, 129.5, 124.0, 121.6, 118.8, 61.0, 59.2, 58.7, 56.9, 55.4, 40.0, 36.2, 29.5, 28.3, 28.1, 25.2

HR-ESI-MS: m/z calcd for $C_{50}H_{58}N_{10}O_8{}^{32}S^7Li$:: 997.4041 found: 997.4065 M−2H+Li⁺

Ga(75)(NO₃)

The Ga complex of 75 was synthesized according to a standard procedure.

¹H NMR (DMSO-d₆, 400 MHz): 10.13 (s, 2H, CO—NH), 8.67 (t, 2H, py-H), 8.36 (d, 2H, py-H), 8.23 (d, 2H, py-H), 7.64 (d, 4H, bz-H), 7.36 (d, 2H, bn-H), 6.41-6.36 (d, 4H, CO—NH), 4.98-4.06 (dd, 4H, N—CH₂), 4.31 (m, 2H), 4.21 (m, 2H), 3.78-3.75 (dd, 4H, N—CH₂), 3.16-2.85 (m, 4H), 2.83-2.81 (m, 6H), 2.81-2.56 (m, 5H, CH₂—CH₂), 2.31 (m, 2H), 1.62-1.32 (m, 10H).

¹³C NMR (DMSO-d₆, 75 MHz): 171.5, 162.7, 162.4, 151.0, 146.5, 143.6, 140.1, 132.7, 128.4, 124.4, 123.3, 118.7, 61.1, 59.2, 55.9, 55.4, 53.7, 46.1, 40.0, 36.3, 29.8, 28.2, 28.1, 25.1

HR-ESI-MS: m/z calcd for $C_{50}H_{58}N_{10}O_8{}^{32}S^{69}Ga$:: 1059.3136 found: 1059.3145 ⁶⁹M⁺

$R_T$ of radiolabeled product on HPLC: 9.1 minutes

Stability versus transferrin (10 min/1 h/2 h; in %): 76/55/43

Avidin blocking experiment: Incubation of the radiolabeled complex with a 10-fold excess of avidin for 30 minutes at 38° C. was found to result in 58% binding of the biotin conjugate. The corresponding blocking experiment with pre-incubation of the same amount of avidin with the corresponding 10-fold excess of biotin and subsequent incubation with the radiolabeled complex for 30 minutes at 38° C. resulted in only 21% binding of the biotin conjugate.

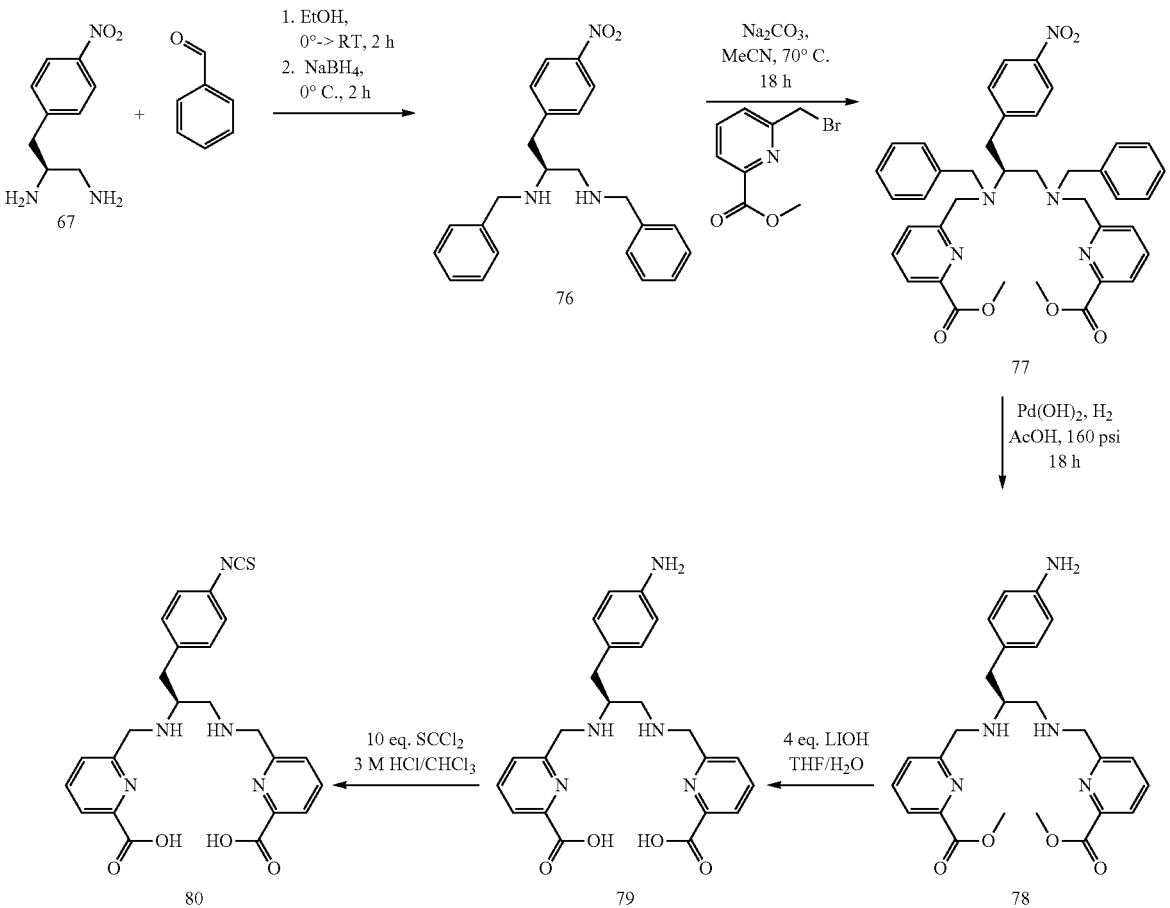

76

3-(4-Nitrophenyl)propane-1,2-diamine (0.204 g, 1.046 mmol) was dissolved in 40 mL EtOH together with benzaldehyde (0.221 g, 0.213 mL, 2.084 mmol) and cooled in an ice bath. After two hours of reaction the imine intermediate was confirmed through mass spectrometry. NaBH$_4$ (80 mg, 2.5 mmol) was added to the reaction mixture at 0° C. and the reaction was stirred for another two hours. Subsequently the reaction was quenched with a saturated aqueous solution of NH$_4$Cl (20 mL) and the product was extracted with 200 mL of DCM. After removal of the solvent, 76 was afforded as an orange oil.

Yield: 0.378 g, 1.01 mmol, 97% R$_f$: 0.1

$^1$H NMR (CDCl$_3$, 400 MHz): 8.13 (d, 2H, bz-H), 7.38-7.27 (m, 12H, bz-H), 3.79 (m, 1H, CH), 3.70 (m, 4H, N—CH$_2$), 2.96 (m, 1H, CH), 2.81 (m, 1H, CH), 2.63 (m, 1H, CH), 2.52 (m, 1H, CH), 2.16 (s, 2H, NH).

$^{13}$C NMR (CDCl$_3$, 75 MHz): 147.2, 146.4, 141.0, 139.9, 129.9, 128.4, 128.3, 128.0, 127.4, 127.0, 123.5, 77.3, 77.0, 76.7, 64.9, 58.1, 57.5, 53.6, 51.3, 51.2, 38.9

HR-ESI-MS: m/z calcd for C$_{32}$H$_{26}$N$_3$O$_2$: 376.2025. found: 376.2019 M+H$^+$

77

76 (0.181 g, 0.48 mmol) and 6-bromomethylpyridine-2-carboxylic acid methyl ester (0.225 g, 0.97 mmol, 2 eq.) were dissolved in acetonitrile (35 mL). Na$_2$CO$_3$ (0.5 g) was added and stirred over night at 70° C. The milky yellow solution was filtered and the solvent was removed. The crude product was subsequently purified with column chromatography (5% MeOH in DCM) to afford the product 77 as a yellow solid.

Yield: 0.078 g, 0.12 mmol, 25% R$_f$: 0.6

$^1$H NMR (CDCl$_3$, 400 MHz): 8.02-7.95 (m, 8H, py-H/bz-H), 7.79 (t, 2H, py-H), 7.61 (t, 4H, bz-H), 7.37-7.04 (m, 6H, bz-H), 4.03 (m, 1H, CH), 4.01-3.94 (m, 6H, CH$_3$), 3.90-3.48 (m, 4H, N—CH$_2$), 3.18 (m, 1H, CH), 2.97 (m, 1H, CH), 2.58 (m, 1H, CH), 2.53 (m, 1H, CH)

$^{13}$C NMR (CDCl$_3$, 75 MHz): 165.6, 160.5, 160.4, 148.9, 146.9, 146.1, 138.8, 138.6, 130.0, 128.8, 128.4, 128.2, 127.4, 126.8, 125.6, 123.5, 123.1, 76.7, 65.2, 61.0, 59.6, 58.6, 54.9, 53.9, 53.7, 53.4, 52.8, 35.8

HR-ESI-MS: m/z calcd for C$_{39}$H$_{40}$N$_5$O$_6$: 674.2979. found: 674.2960 M+H$^+$ Elemental Analysis: N, 8.72; C, 58.36; H, 5.05 (calcd. N, 8.30; C, 58.37; H, 5.10 for 6·2 DCM)

78

Compound 77 (0.302 g, 0.44 mmol) was dissolved in glacial acetic acid (20 mL). Pd(OH)$_2$ (80 mg) was added and the mixture was charged with H$_2$ (160 psi) in a Parr hydrogenator and stirred over night at room temperature. The reaction was found to be complete according to TLC (product stains bright purple after staining with ninhydrin). Pd(OH)$_2$ was filtered off and the solvent was removed in vacuo to afford the pure product 78 as the triacetate salt.

Yield: 0.149 g, 0.32 mmol, 72% R$_f$: 0.05

$^1$H NMR (CDCl$_3$, 400 MHz): 7.99-7.94 (m, 3H, py-H), 7.89 (t, 1H, py-H), 7.56 (d, 1H, py-H), 7.46 (d, 1H, py-H), 7.32 (d, 1H, py-H), 6.91(d, 2H, bz-H), 6.56(d, 2H, bz-H), 4.76-4.09 (m, 4H, N—CH$_2$), 3.94 (m, 1H, CH), 3.80-3.79 (m, 6H, CH$_3$), 3.65 (m, 1H, CH), 3.02 (m, 1H, CH), 2.72 (m, 1H, CH), $^{13}$C NMR (CDCl$_3$, 75 MHz): 164.9, 164.7, 146.9, 146.6, 144.7, 138.3, 138.1, 137.2, 129.9, 126.9, 126.2, 126.0, 125.8, 124.3, 124.0, 122.3, 115.7, 57.1, 53.5, 52.7, 52.6, 49.7, 48.7, 35.9, 24.1

HR-ESI-MS: m/z calcd for C$_{25}$H$_{29}$N$_5$O$_4$Na: 486.2117. found: 486.2111 M+Na$^+$

79

Compound 78 (0.017 g, 0.036 mmol) was dissolved in THF (3 mL) to afford a blurry yellow solution. LiOH (0.004 g, 0.15 mmol) was dissolved in H$_2$O (1 mL) and added to the reaction mixture. The reaction was found to be complete by HPLC after 1 h (R$_{t(7)}$=10.6 minutes, R$_{t(8)}$=8.5 minutes). The solvent was removed to afford the product 79 as a yellow solid.

Yield: 0.015 g, 0.034 mmol, 94% R$_t$(79)=8.5 minutes $^1$H NMR (CDCl$_3$, 400 MHz): 8.90-7.75 (m, 6H, py-H), 7.56-7.32 (m, 4H, bz-H), 4.75-4.49 (m, 4H, N—CH$_2$), 4.20-3.15 (m, 5H, CH).

$^{13}$C NMR (CDCl$_3$, 75 MHz): 166.0, 165.4, 165.3, 158.0, 152.2, 151.6, 151.5, 147.5, 147.0, 146.9, 146.8, 139.1, 137.9, 130.7, 130.6, 130.2, 128.6, 126.8, 126.7, 126.7, 124.1, 123.9, 123.1, 121.9, 55.8, 50.2, 47.3, 46.4, 33.76.

HR-ESI-MS: m/z calcd for C$_{23}$H$_{26}$N$_5$O$_4$: 436.1985. found: 436.1989 M+H$^+$

80

Compound 79 (0.010 g, 0.023 mmol) was dissolved in 3 M HCl (1 mL) and CHCl$_3$ (1 mL) was added, as well as SCCl$_2$ (19 μL, 10 eq.) and the biphasic reaction was stirred vigorously for 18 h at room temperature. Subsequently, the solvent was removed and the crude product was purified by preparative HPLC. The clean fractions were pooled and lyophilized to afford the final product as a yellow solid.

Yield: 0.003 g, 0.006 mmol, 26% R$_t$(80)=13 minutes.

$^1$H NMR (d-DMSO, 600 MHz): 7.99-7.49 (m, 6H, py-H), 7.08 (s, 4H, bz-H), 4.70-4.49 (m, 4H, N—CH$_2$), 3.86 (m, 1H, CH), 3.58 (m, 1H, CH), 3.27-3.23 (m, 2H, CH), 2.84 (m, 1H, CH).

$^{13}$C NMR (d-DMSO, 75 MHz): 168.8, 168.2, 162.7, 162.4, 150.0, 149.5, 148.6, 147.9, 139.6, 139.1, 134.2, 133.0, 130.0, 129.9, 129.7, 126.0, 125.8, 125.4, 124.3, 56.7, 49.6, 47.0, 46.3, 34.0

HR-ESI-MS: m/z calcd for C$_{24}$H$_{22}$N$_5$O$_4$$^{32}$S: 476.1393. found: 476.1405 M–H$^-$

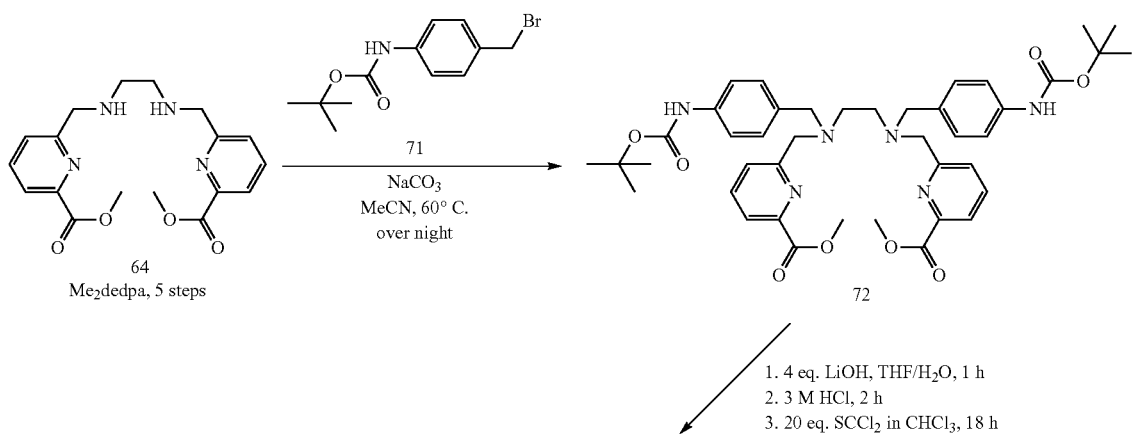

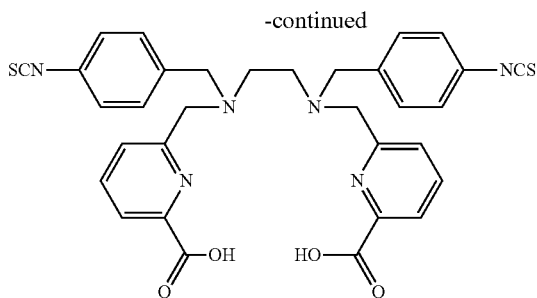

81

81

Compound 72 (0.013 g, 0.069 mmol) was dissolved in a 3:1 mixture of THF and H$_2$O. LiOH (0.008 g, 0.3 mmol) was added to the reaction mixture and the reaction was stirred for 1 h at room temperature to afford the free carboxylate intermediate. Reaction control was performed via TLC and analytical HPLC (R$_{t(1)}$=18.3 minutes, R$_{t(intermediate)}$=15.8 minutes). The solvent was removed in vacuo and the intermediate was redissolved in 3 M HCl solution (2 mL) and stirred for 2 h to remove the amino protection groups. Again, HPLC was used to confirm full conversion of the intermediate into the fully deprotected second intermediate (R$_{t(sec.\ intermediate)}$=9.4 minutes). CHCl$_3$ (1 mL) was added, as well as SCCl$_2$ (106 µL, 20 eq.) and the biphasic reaction was stirred vigorously for 18 h at room temperature to afford the final product 81 as a white precipitate, which was collected by vacuum filtration.

Yield: 0.011 g, 0.017 mmol, 24%, R$_t$(81)=18.0 minutes.

$^1$H NMR (DMSO-d$_6$, 400 MHz): 7.95 (d, 2H, py-H), 7.55-7.48 (m, 4H, py-H), 7.32 (m, 4H, bz-H), 4.23 (s, 4H, N—CH$_2$), 4.11 (s, 4H, N—CH$_2$), 3.31 (s, 4H, N—CH$_2$).

$^{13}$C NMR (DMSO-d$_6$, 75 MHz): 165.6, 154.2, 147.5, 138.5, 133.9, 131.8, 130.1, 126.9, 125.9, 123.9, 57.0, 56.3, 49.0.

HR-ESI-MS: m/z calcd for C$_{32}$H$_{27}$N$_6$O$_4{}^{32}$S$_2$: 623.1535. found: 623.1542 M–H$^-$ 80-RGD and 81-RGD:

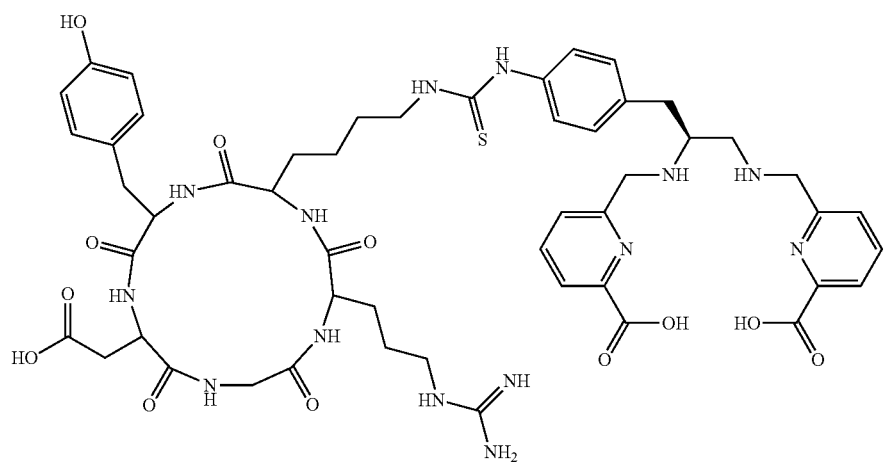

80-RGD

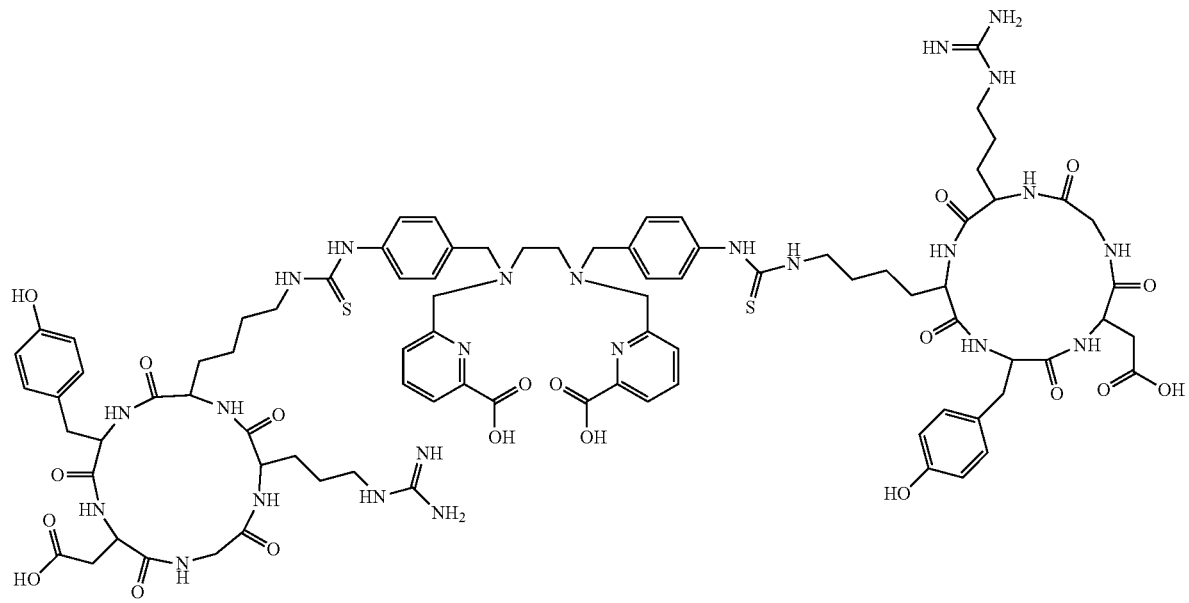

General procedure for RGD coupling: The cyclic RGD peptide (3 mg, 0.0048 mmol) was dissolved in an aqueous buffered solution (0.1 M NaHCO$_3$, pH 9, 1.5 mL). Isothiocyanate 80 (1.9 mg, 0.004 mmol) or isothiocyanate 81 (1.3 mg, 0.0022 mmol) was dissolved in MeOH (0.5 mL). The solutions of the cyclic RGD peptide and of the isothiocyanate were mixed and stirred under the exclusion of light at room temperature for 24 h. The solvent was subsequently removed and the crude product was redissolved in a minimal amount of a MeCN/H$_2$O mixture (1:2) and purified via HPLC (Phenomenex Jupiter 5µ C18 300 A 4.6×100 mm HPLC column; gradient of A(100%)–B(100%) in 25 minutes at 1 mL/min flow rate (A: H$_2$O, 0.1% TFA; B: MeCN)). The fractions containing the conjugated product were pooled and the solvent was removed to afford purified RGD conjugate as a white solid in approximately 45% yield. The product was analyzed by ESI-MS.

80-RGD: R$_t$: 10.5 min; [M–H$^+$]$^-$=1862.0 (calculated for C$_{87}$H$_{110}$N$_{23}$O$_{20}$S$_2$: 1861.8)

81-RGD: R$_t$: 11.5 min; [M+H$^+$]$^+$=1097.6 (calculated for C$_{51}$H$_{65}$N$_{14}$O$_{12}$S: 1097.5)

Radiolabeling of 80-RGD and 81-RGD with $^{67}$Ga and $^{64}$Cu

| parameter | 80-RGD | 81-RGD |
|---|---|---|
| $^{67}$Ga | | |
| Retention time of radiochemical complex[†] | R$_t$ = 6.8 min | R$_t$ = 7.6 min |
| Ligand concentration and corresponding radiolabeling yield | 10$^{-5}$M | 98% (0.609 mCi) | 98% (1.65 mCi) |
| Transferrin stability challenge: Stability at different time points | 10 min | 96% | 92% |
| | 1 h | 96% | 27% |
| | 2 h | 96% | 15% |
| $^{64}$Cu | | |
| Retention time of radiochemical complex[‡] | R$_t$ = 8.4 min | R$_t$ = 9.2 min |
| Ligand concentration and corresponding radiolabeling | 10$^{-5}$M | 97% (1.096 mCi) | 96.5% (1.046 mCi) |
| yield | 10$^{-6}$M | 82% | 97% |
| Serum stability challenge: Stability at different time points | 10 min | 96% | 95% |
| | 1 h | 97% | 97% |
| | 4 h | 96% | 97% |

[†]Retention time was measured using a Waters XBridge BEH130 4.6 × 150 mm (gradient: A: NaOAc buffer, pH 4.5, B: CH$_3$CN, 0-100% B linear gradient 20 min)

[‡]Retention time was measured using a Waters XBridge BEH130 4.6 × 150 mm (gradient: A: H$_2$O, 0.1% TFA, B: CH$_3$CN, 5-100% B linear gradient 30 min)

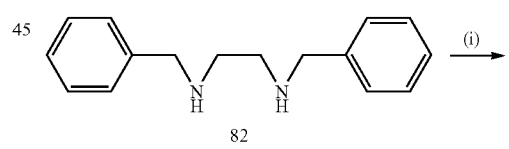

82

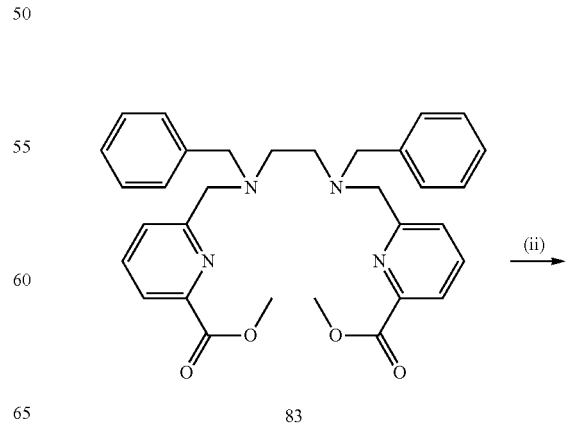

83

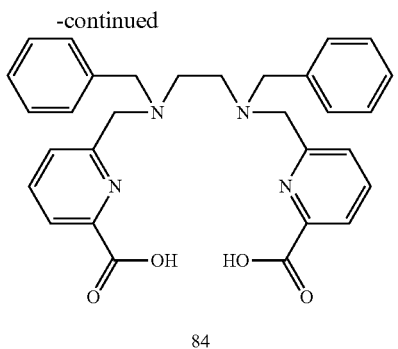

84

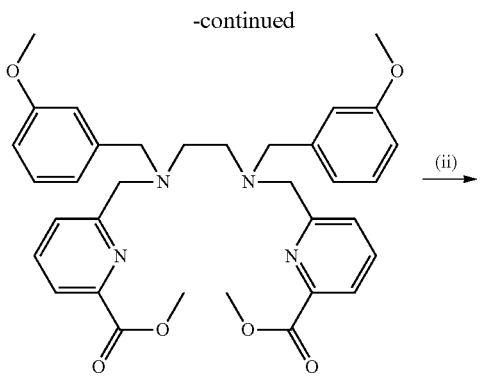

85

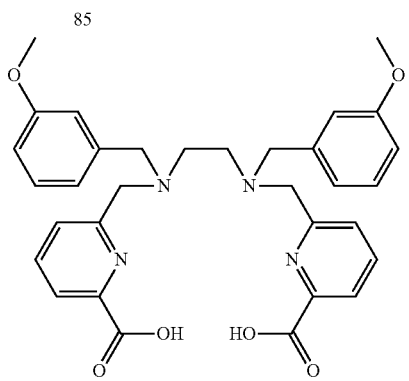

86

Yield: 0.052 g, 0.096 mmol, 46% $R_f$: 0.45

$^1$H NMR (CDCl$_3$, 400 MHz): 7.96-7.94 (m, 2H, py-H), 7.72-7.68 (m, 4H, py-H), 7.26-7.19 (m, 10H, bn-H), 3.97 (s, 6H, CH$_3$), 3.81 (s, 4H, N—CH$_2$), 3.57 (s, 4H, N—CH$_2$), 2.68 (s, 4H, CH$_2$—CH$_2$)

$^{13}$C NMR (CDCl$_3$, 75 MHz): 166.0, 161.3, 147.2, 139.1, 137.4, 128.8, 127.2, 125.9, 123.6, 60.7, 59.3, 53.0, 52.2

HR-ESI-MS: m/z calcd for C$_{32}$H$_{35}$N$_4$O$_4$: 539.2658. found: 539.2645 M+H$^+$

84

Yield: 0.041 g, 0.082 mmol, 85% $R_f$: 0.02

$^1$H NMR (CD$_3$OD, 400 MHz): 8.01 (d, 2H, py-H), 7.89 (t, 2H, py-H), 7.37 (d, 2H, py-H), 7.25-7.21 (m, 8H, bn-H), 7.04 (m, 2H, bn-H), 3.87 (s, 4H, N—CH$_2$), 3.41 (s, 4H, N—CH$_2$), 2.31 (s, 4H, CH$_2$—CH$_2$)

$^{13}$C NMR (CD$_3$OD, 75 MHz): 172.5, 159.5, 154.7, 139.8, 136.3, 131.4, 129.2, 128.5, 125.7, 123.2, 61.0, 57.6, 48.5

HR-ESI-MS: m/z calcd for C$_{30}$H$_{29}$N$_4$O$_4$: 509.2189. found: 509.2193 M−H$^-$ Ga(84)NO$_3$ $^1$H NMR (CD$_3$OD, 400 MHz): 8.69 (t, 2H, py-H), 8.48 (d, 2H, py-H), 8.21 (d, 2H, py-H), 7.45 (brs, 10H, bz-H), 4.94 (d, 2H, N—CH$_2$), 4.32 (d, 2H, N—CH$_2$), 4.05 (d, 2H, N—CH$_2$), 3.81 (d, 2H, N—CH$_2$), 3.20 (dd, 4H, CH$_2$—CH$_2$)

$^{13}$C NMR (CD$_3$OD, 75 MHz): 165.3, 152.3, 148.0, 145.5, 133.3, 130.9, 130.3, 130.0, 125.3, 57.8, 56.6, 47.9

HR-ESI-MS: m/z calcd for C$_{30}$H$_{28}$N$_4$O$_4$$^{69}$Ga: 577.1366. found: 577.1368 $^{69}$M$^+$ $R_T$ of radiolabeled product on HPLC: 9.9 minutes Stability versus transferrin (10 min/1 h/2 h; in %): 96/74/66

Ga$^{68}$ labeling: 10$^{-6}$ M ligand conc., 97%, 0.45 mCi/nmol log P: −1.25

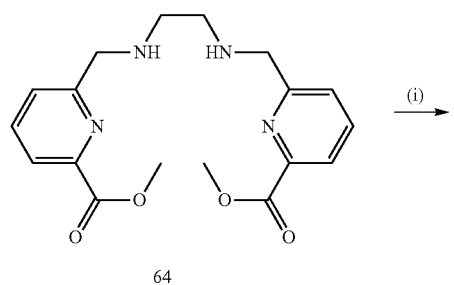

64

85

Yield: 0.05 g, 0.083 mmol, 59%, $R_f$: 0.5

$^1$H NMR (CDCl$_3$, 400 MHz): 7.98 (d, 2H, py-H), 7.73-7.72 (m, 4H, bn-H) 7.18 (t, 2H, py-H), 6.89 (m, 4H, bn-H), 6.71 (d, 2H, py-H), 4.0 (s, 6H, CH$_3$), 3.85 (s, 4H, N—CH$_2$), 3.78 (s, 6H, methoxy-CH$_3$), 3.58 (s, 4H, N—CH$_2$), 2.71 (s, 4H, CH$_2$—CH$_2$)

$^{13}$C NMR (CDCl$_3$, 75 MHz): 166.0, 161.3, 159.8, 147.3, 140.9, 137.5, 129.4, 126.0, 123.7, 121.2, 114.4, 112.4

HR-ESI-MS: m/z calcd for C$_{34}$H$_{39}$N$_4$O$_6$: 599.2870. found: 599.2882 M+H$^+$

86

Yield: 0.037 g, 0.065 mmol, 78% $R_f$: 0.1

$^1$H NMR (CD$_3$OD, 400 MHz): 7.99 (d, 2H, py-H), 7.89 (t, 2H, py-H), 7.39 (d, 2H, py-H), 7.15 (d, 2H, bn-H), 6.79 (d, 4H, bn-H), 6.61 (d, 2H, bn-H), 3.89 (s, 4H, N—CH$_2$), 3.73 (s, 6H, methoxy-CH$_3$), 3.38 (s, 4H, N—CH$_2$), 2.38 (s, 4H, CH$_2$—CH$_2$)

$^{13}$C NMR (CD$_3$OD, 75 MHz): 160.8, 159.4, 154.6, 139.6, 137.7, 130.0, 125.5, 123.6, 122.9, 116.9, 113.5, 60.9, 57.2, 55.6

HR-ESI-MS: m/z calcd for C$_{32}$H$_{33}$N$_4$O$_6$: 569.2400. found: 569.2396 M−H$^-$ Ga(86)NO$_3$ $^1$H NMR (CD$_3$OD, 400 MHz): 8.62 (t, 2H, py-H), 8.41 (d, 2H, py-H), 8.09 (d, 2H, py-H), 7.36 (t, 2H, bz-H), 7.05 (d, 2H, bz-H), 6.86 (brs, 4H, bz-H), 4.86 (d, 2H, N—CH$_2$), 4.36 (d, 2H, N—CH$_2$), 4.01 (d, 2H, N—CH$_2$), 3.78 (s, 12H, methoxy-CH$_3$), 3.59 (d, 2H, N—CH$_2$), 3.02 (dd, 4H, CH$_2$—CH$_2$)

$^{13}$C NMR (CD$_3$OD, 75 MHz): 164.7, 158.7, 147.8, 142.8, 130.0, 129.7, 128.3, 124.1, 124.0, 123.9, 117.1, 114.5, 55.8, 54.9, 54.7, 46.2

89

HR-ESI-MS: m/z calcd for $C_{32}H_{32}N_4O_6{}^{69}Ga$: 637.1578. found: 637.1566 $^{69}M^+$
$R_T$ of radiolabeled product on HPLC: 10.8 minutes
Stability versus transferrin (10 min/1 h/2 h; in %): 95/66/55
$Ga^{68}$ labeling: $10^{-6}$M ligand conc., 96.5%, 0.45 mCi/nmol
log P: −0.83

90

HR-ESI-MS: m/z calcd for $C_{34}H_{37}N_4O_8$: 629.2611. found: 629.2615 M−H⁻

$Ga(88)NO_3$ $^1$H NMR (CD$_3$OD, 400 MHz): 8.69 (t, 2H, py-H), 8.49 (d, 2H, py-H), 8.20 (d, 2H, py-H), 6.61 (brs, 6H, bz-H), 4.98 (d, 2H, N—CH$_2$), 4.37 (d, 2H, N—CH$_2$), 3.98 (d, 2H, N—CH$_2$), 3.81 (s, 12H, methoxy-CH$_3$), 3.67 (d, 2H, N—CH$_2$), 3.18 (dd, 4H, CH$_2$—CH$_2$)

$^{13}$C NMR (CD$_3$OD, 75 MHz): 165.3, 162.9, 152.5, 147.9, 145.6, 132.8, 129.8, 125.3, 111.2, 110.9, 102.3, 58.1, 56.8, 56.1, 47.9

HR-ESI-MS: m/z calcd for $C_{34}H_{36}N_4O_8{}^{69}Ga$: 697.1789. found: 697.1803 69M⁺

$R_T$ of radiolabeled product on HPLC: 11.6 minutes
Stability versus transferrin (10 min/1 h/2 h; in %): 76/59/52
$Ga^{68}$ labeling: $10^{-6}$ M ligand conc., 95%, 0.45 mCi/nmol
log P: −0.32

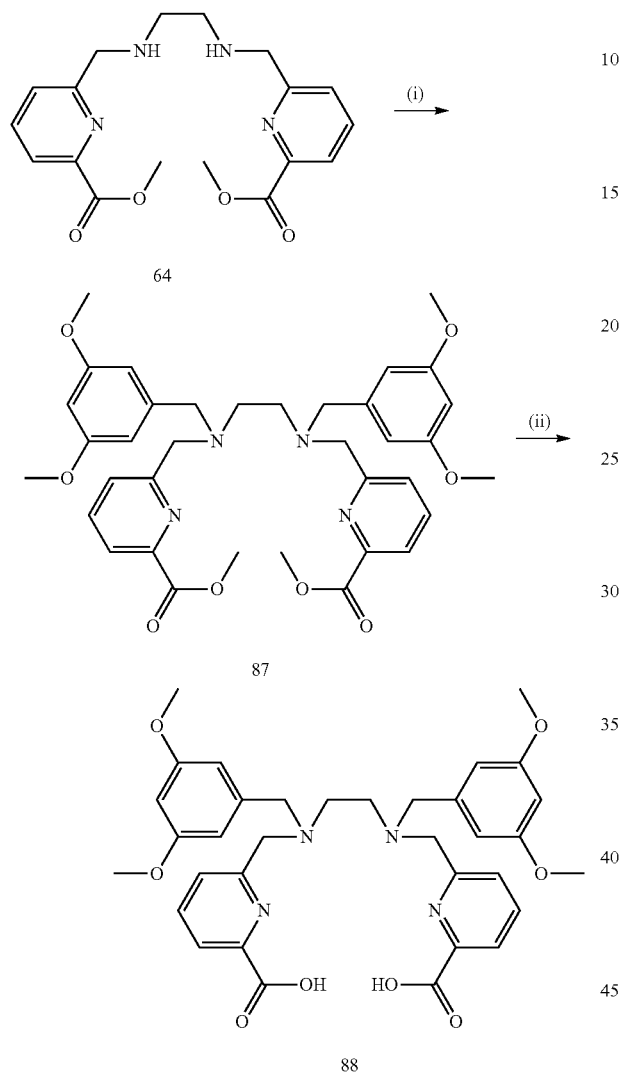
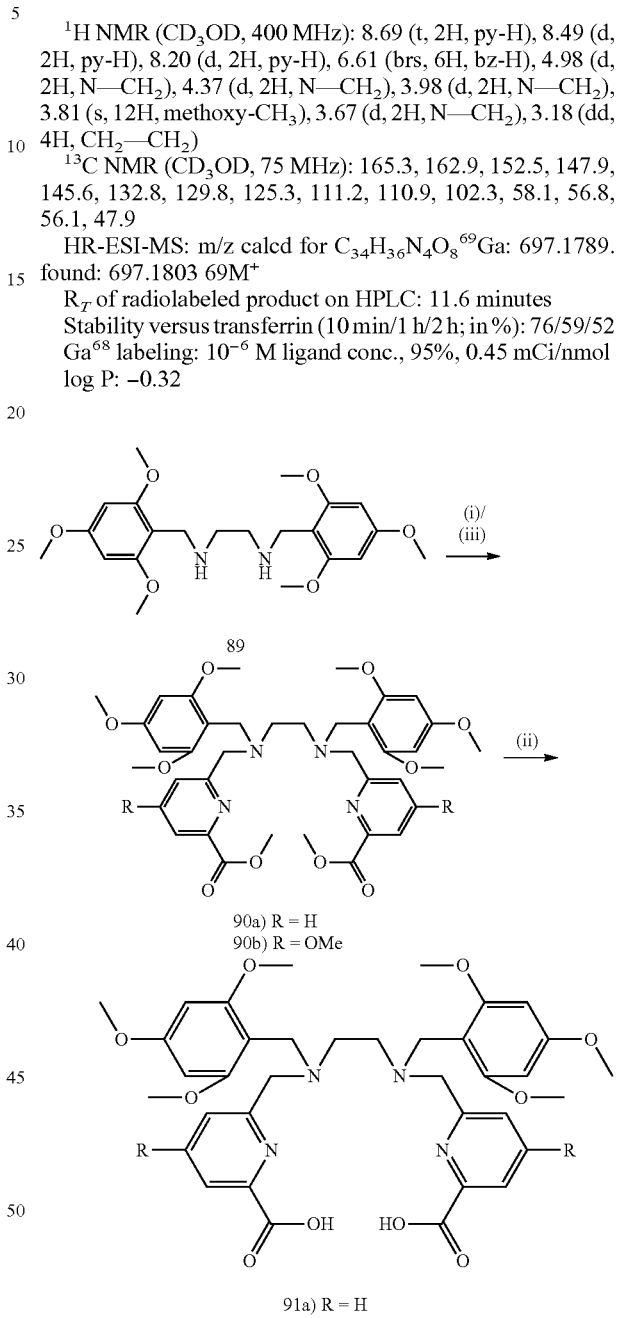

87
Yield: 0.051 g, 0.077 mmol, 56% $R_f$: 0.45
$^1$H NMR (CDCl$_3$, 400 MHz): 7.96 (t, 2H, py-H), 7.70 (m, 4H, py-H), 6.46 (s, 4H, bn-H), 6.30 (s, 2H, bn-H), 3.97 (s, 6H, CH$_3$), 3.83 (s, 4H, N—CH$_2$), 3.73 (s, 12H, methoxy-CH$_3$), 3.53 (s, 4H, N—CH$_2$), 2.69 (s, 4H, CH$_2$—CH$_2$)
$^{13}$C NMR (CDCl$_3$, 75 MHz): 165.9, 161.2, 160.9, 147.3, 141.8, 137.4, 126.0, 123.6, 106.6, 98.9, 60.7, 59.4, 52.9, 52.4
HR-ESI-MS: m/z calcd for $C_{36}H_{43}N_4O_8$: 659.3081. found: 659.3068 M+H⁺

88
Yield: 0.042 g, 0.063 mmol, 83% $R_f$: 0.15
$^1$H NMR (CD$_3$OD, 400 MHz): 7.99 (d, 2H, py-H), 7.88 (t, 4H, py-H), 7.41 (d, 4H, py-H), 6.35 (s, 2H, bn-H), 6.321 (s, 4H, bn-H), 3.89 (s, 4H, N—CH$_2$), 3.69 (s, 12H, methoxy-CH$_3$), 3.34 (s, 4H, N—CH$_2$), 2.36 (s, 4H, CH$_2$—CH$_2$)
$^{13}$C NMR (CD$_3$OD, 75 MHz): 162.2, 159.7, 154.8, 139.8, 138.8, 125.7, 123.1, 109.4, 100.1, 61.1, 56.8, 55.8

90a)
Yield: 0.079 g, 0.11 mmol, 55% $R_f$: 0.4
$^1$H NMR (CDCl$_3$, 400 MHz): 8.27 (d, 2H, py-H), 7.99 (d, 2H, py-H), 7.86 (t, 2H, py-H), 6.02 (s, 4H, bn-H), 4.31 (s, 4H, N—CH$_2$), 3.96 (s, 6H, CH$_3$), 3.94 (s, 4H, N—CH$_2$), 3.78 (s, 6H, p-methoxy-CH$_3$), 3.68 (s, 12H, o-methoxy-CH$_3$), 3.19 (s, 4H, CH$_2$—CH$_2$)
$^{13}$C NMR (CDCl$_3$, 75 MHz): 165.2, 161.9, 159.9, 146.8, 137.9, 127.9, 124.2, 90.2, 55.5, 55.3, 52.7, 45.5
HR-ESI-MS: m/z calcd for $C_{38}H_{47}N_4O_{10}$: 719.3292. found: 719.3303 M+H⁺

91a)

Yield: 0.061 g, 0.088 mmol, 80% $R_f$: 0.2

$^1$H NMR (CD$_3$OD, 400 MHz): 7.95 (d, 2H, py-H), 7.84 (t, 2H, py-H), 7.30 (t, 2H, py-H), 6.12 (s, 4H, bn-H), 3.93 (s, br, 4H, N—CH$_2$), 3.62 (s, 6H, p-methoxy-CH$_3$), 3.63 (s, 12H, o-methoxy-CH$_3$), 3.41 (s, 4H, N—CH$_2$), 2.19 (s, 4H, CH$_2$—CH$_2$)

$^{13}$C NMR (CD$_3$OD, 75 MHz): 172.6, 162.4, 161.7, 160.9, 154.7, 139.5, 125.2, 122.6, 105.7, 91.5, 61.9, 55.9, 55.8, 48.7, 43.6

HR-ESI-MS: m/z calcd for C$_{36}$H$_{41}$N$_4$O$_{10}$: 689.2823. found: 689.2812 M+H$^+$ Ga(91a)NO$_3$ $^1$H NMR (CD$_3$OD, 400 MHz): 8.68 (t, 2H, py-H), 8.48 (d, 2H, py-H), 8.18 (d, 2H, py-H), 6.31 (brs, 4H, bz-H), 4.92 (d, 2H, N—CH$_2$), 4.45 (d, 2H, N—CH$_2$), 4.07 (d, 2H, N—CH$_2$), 3.85 (s, 6H, methoxy-CH$_3$), 3.79 (s, 12H, methoxy-CH$_3$), 3.46 (d, 2H, N—CH$_2$), 3.84 (dd, 4H, CH$_2$—CH$_2$)

$^{13}$C NMR (CD$_3$OD, 75 MHz): 164.8, 162.0, 153.2, 148.1, 145.9, 129.7, 125.2, 100.2, 92.2, 57.9, 56.5, 56.2, 45.5

HR-ESI-MS: m/z calcd for C$_{36}$H$_{40}$N$_4$O$_{10}$$^{69}$Ga: 757.2000. found: 757.2005 $^{69}$M$^+$ $R_T$ of radiolabeled product on HPLC: 11.8 minutes Stability versus transferrin (10 min/1 h/2 h; in %): 86/85/82

Ga$^{68}$ labeling: 10$^{-6}$ M ligand conc., 94%, 0.45 mCi/nmol log P: −0.03

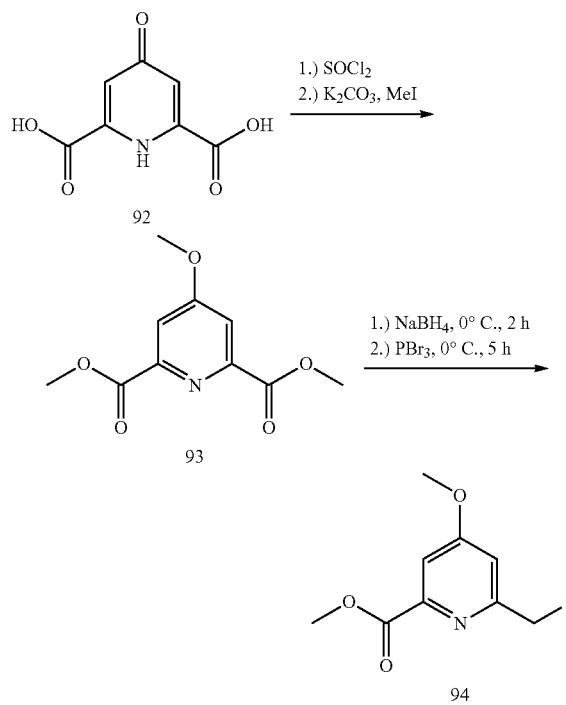

94 was synthesized in 4 steps. The first two steps include a two-step methylation of the two carboxylates and the alcohol according to reference[52], followed by a standard partial reduction according to the literature[53], followed by bromination of the alcohol[54] to afford 94.

Yield: 31% (over-all yield)

$^1$H NMR (CDCl$_3$, 400 MHz): 7.46 (d, 1H, py-H), 7.06 (d, 1H, py-H), 4.73 (s, 2H, CH$_2$), 3.88 (s, 3H, CH$_3$), 3.82 (s, 3H, CH$_3$)

$^{13}$C NMR (CDCl$_3$, 75 MHz): 167.4, 165.4, 158.6, 149.3, 112.81, 110.9, 55.86, 53.15, 33.5

HR-ESI-MS: m/z calcd for C$_9$H$_{10}$NO$_3$$^{79}$BrNa: 281.9742. found: 281.9739 M+Na$^+$ Elemental Analysis: N, 5.31; C, 41.7; H, 3.88 (calcd. N, 5.89; C, 41.56; H, 3.88)

90b)

Yield: 0.311 g, 0.4 mmol, 70% $R_f$: 0.4

$^1$H NMR (CDCl$_3$, 400 MHz): 7.32 (s, 4H, py), 5.89 (s, 4H, bn-H), 4.08 (s, 4H, N—CH$_2$), 3.83 (s, 4H, N—CH$_2$), 3.77 (s, 6H, py-methoxy-CH$_3$), 3.64 (s, 6H, p-bz-methoxy-CH$_3$) 3.55 (s, 12H, carboxyl-methoxy-CH$_3$), 3.25 (s, 12H, o-bz-methoxy-CH$_3$), 3.03 (s, 4H, CH$_2$—CH$_2$)

$^{13}$C NMR (CDCl$_3$, 75 MHz): 167.3, 165.3, 162.3, 160.1, 157.9, 148.4, 112.9, 111.3, 90.5, 58.3, 56.3, 55.7, 55.5, 52.9, 50.0, 49.2, 45.9

HR-ESI-MS: m/z calcd for C$_{40}$H$_{51}$N$_4$O$_{12}$: 779.3503. found: 779.3493 M+H$^+$ 91b)

Yield: 0.061 g, 0.088 mmol, 87% $R_f$: 0.35

$^1$H NMR (CD$_3$OD, 400 MHz): 7.50 (d, 2H, py), 6.84 (d, 2H, py-H), 6.13 (s, 4H, bn-H), 3.89 (s, 6H, py-methoxy-CH$_3$), 3.77 (s, 6H, p-bz-methoxy-CH$_3$) 3.61 (s, 12H, o-bz-methoxy-CH$_3$), 3.41 (s, 4H, N—CH$_2$), 3.34 (s, 4H, N—CH$_2$), 2.10 (s, 4H, CH$_2$—CH$_2$)

$^{13}$C NMR (CD$_3$OD, 75 MHz): 172.4, 169.6, 162.7, 161.7, 156.7, 110.9, 108.5, 106.0, 91.5, 65.1, 55.9, 43.8

HR-ESI-MS: m/z calcd for C$_{38}$H$_{46}$N$_4$O$_{12}$$^7$Li: 757.3272. found: 757.3260 M+H$^+$ Ga(91b)NO$_3$ $^1$H NMR (CD$_3$OD, 400 MHz): 7.85 (d, 2H, py), 7.62 (d, 2H, py-H), 6.27 (s, 4H, bn-H), 4.73-4.24 (dd, 4H, N—CH$_2$), 4.15 (s, 6H, py-methoxy-CH$_3$), 4.00-3.43 (dd, 4H, N—CH$_2$), 3.82 (s, 6H, p-bz-methoxy-CH$_3$), 3.76 (s, 12H, o-bz-methoxy-CH$_3$), 2.99-2.77 (dd, 4H, CH$_2$—CH$_2$)

$^{13}$C NMR (CD$_3$OD, 75 MHz): 175.6, 165.5, 164.9, 162.1, 154.6, 147.8, 113.9, 111.9, 100.4, 92.3, 58.8, 57.9, 56.6, 56.3, 49.9, 45.5

HR-ESI-MS: m/z calcd for C$_{38}$H$_{44}$N$_4$O$_{12}$$^{69}$Ga: 817.2212. found: 817.2220 $^{69}$M$^+$ $R_T$ of radiolabeled product on HPLC: 12.4 minutes Stability versus transferrin (10 min/1 h/2 h; in %): 97/96/96 log P: 0.66

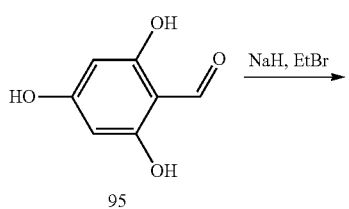

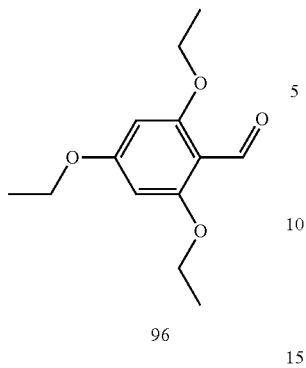

96

96 was synthesized in one step. The trihydroxide (1.88 g, 9.9 mmol) was dissolved in DMF. NaH (0.960 g, 0.024 mol, in 60% dispersion in mineral oil) was added, followed by EtBr (16.240 g, 11.05 mL, 0.149 mol). The mixture was stirred over night at room temperature. After no trialkylated product was observed, another batch of NaH (0.301 g, 0.0125 mol, in 60% dispersion in mineral oil) was added, together with more EtBr (2.05 g, 1.397 mL, 0.0188 mol). The mixture was stirred over night at 60° C. and quenched with $H_2O$ (50 mL). The crude product was extracted with DCM, and the organic phase was washed twice with saturated brine. Subsequently, the solvent was removed and the residual crude product was purified with column chromatography ($SiO_2$, 3:2 mixture of Hexane/EtOAc) to afford the clean product as a colorless solid.

Yield: 0.970 g, 3.4 mmol, 34%, $R_f$=0.21

$^1$H NMR ($CDCl_3$, 400 MHz): 10.34 (s, 1H, CO—H), 5.99 (s, 2H, aryl-H), 4.03 (q, 6H, $CH_2$), 1.39 (m, 9H, $CH_3$)

$^{13}$C NMR ($CDCl_3$, 75 MHz): 187.9, 165.5, 163.5, 109.1, 91.6, 64.6, 63.9, 14.65

HR-ESI-MS: m/z calcd for $C_{13}H_{19}O_9$: 239.1283. found: 239.1286 M+H$^+$

Elemental Analysis: N, 0.07; C, 65.37; H, 7.48 (calcd. C, 65.53; H, 7.61)

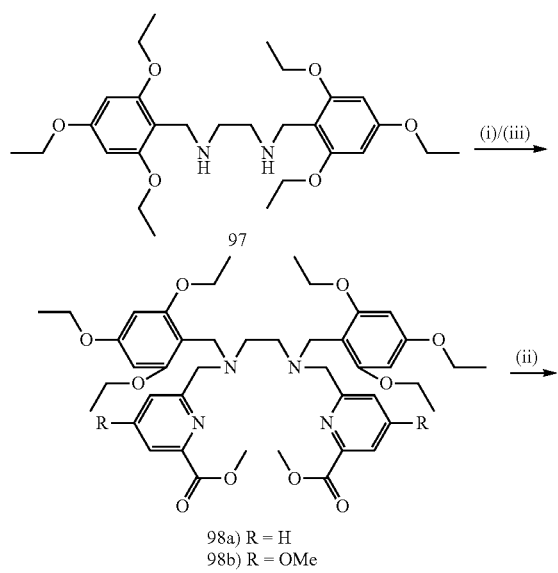

98a) R = H
98b) R = OMe

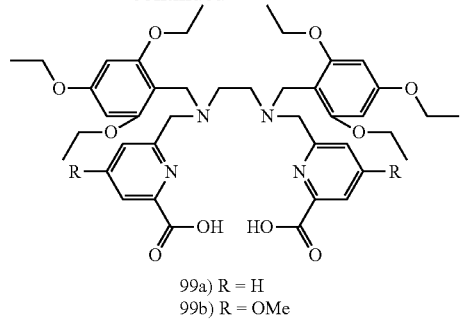

99a) R = H
99b) R = OMe $^1$H NMR ($CDCl_3$, 400 MHz): 6.01 (s, 4H, bn-H), 4.08 (s, 4H, N—$CH_2$), 3.91 (q, 12H, O—$CH_2$), 3.74 (s, 4H, $CH_2$—$CH_2$), 1.30 (t, 18H, $CH_3$)

$^{13}$C NMR ($CDCl_3$, 75 MHz): 159.9, 158.8, 107.3, 92.04, 91.8, 46.0, 40.3, 14.9

HR-ESI-MS: m/z calcd for $C_{28}H_{45}N_2O_6$: 505.3278. found: 505.3269 M+H$^+$ 98a)

Yield: 0.112 g, 0.13 mmol, 52% $R_f$: 0.2

$^1$H NMR ($CDCl_3$, 400 MHz): 8.01 (d, 2H, py-H), 7.94 (d, 2H, py-H), 7.82 (t, 2H, py-H), 5.94 (s, 4H, bn-H), 4.30 (s, 4H, N—$CH_2$), 3.94 (s, 4H, N—$CH_2$), 3.88 (m, 18H, O—$CH_3$/O—$CH_2$), 3.11 (s, 4H, $CH_2$—$CH_2$), 1.35-1.09 (m, 18H, $CH_3$)

$^{13}$C NMR ($CDCl_3$, 75 MHz): 165.4, 161.5, 159.6, 147.1, 138.4, 128.2, 124.7, 64.1, 63.7, 58.7, 53.6, 52.9, 48.9, 45.6, 14.8

HR-ESI-MS: m/z calcd for $C_{44}H_{59}N_4O_{10}$: 803.4231. found: 803.4248 M+H$^+$ 99a)

Yield: 0.091 g, 0.12 mmol, 92% $R_f$: 0.2

$^1$H NMR ($CD_3OD$, 400 MHz): 7.97 (d, 2H, py-H), 7.87 (t, 2H, py-H), 7.29 (d, 2H, py-H), 6.06 (s, 4H, bn-H), 3.98 (s, 4H, N—$CH_2$), 3.97-3.81 (q, 12H, O—$CH_2$), 3.43 (s, 4H, N—$CH_2$), 2.21 (s, 4H, $CH_2$—$CH_2$), 1.39-1.16 (m, 18H, $CH_3$)

$^{13}$C NMR ($CD_3OD$, 75 MHz): 171.2, 160.0, 159.8, 153.4, 138.2, 123.9, 121.4, 104.7, 91.3, 63.5, 63.3, 61.5, 42.7, 14.1

HR-ESI-MS: m/z calcd for $C_{42}H_{53}N_4O_{10}$: 773.3762. found: 773.3744 M+H$^+$ Ga(99a)NO$_3$ $^1$H NMR ($CD_3OD$, 400 MHz): 6.69 (t, 2H, py-H), 8.45 (d, 2H, py-H), 8.19 (d, 2H, py-H), 6.22 (s, 4H, bn-H), 4.97-4.43 (dd, 4H, N—$CH_2$), 4.09-3.43 (dd, 4H, N—$CH_2$), 4.01 (q, 12H, O—$CH_2$), 3.82, 3.29-2.84 (dd, 4H, $CH_2$—$CH_2$), 1.37-1.17 (m, 18H, $CH_3$)

$^{13}$C NMR ($CD_3OD$, 150 MHz): 163.1, 161.9, 159.4, 150.9, 146.4, 144.1, 127.4, 123.3, 98.4, 91.4, 63.7, 62.9, 56.0, 48.4, 43.8, 13.3, 13.2

HR-ESI-MS: m/z calcd for $C_{42}H_{52}N_4O_{10}$$^{69}$Ga: 841.2939. found: 841.2953 $^{69}$M$^+$ $R_T$ of radiolabeled product on HPLC: 14.6 minutes Stability versus transferrin (10 min/1 h/2 h; in %): 95/92/91

98b)

Yield: 0.116 g, 0.13 mmol, 52% $R_f$: 0.4

$^1$H NMR ($CDCl_3$, 400 MHz): 7.57 (s, 2H, py-H), 7.47 (s, 2H, py-H), 5.96 (s, 4H, bn-H), 4.24 (s, 4H, N—$CH_2$), 3.96 (s, 4H, N—$CH_2$), 3.91 (m, 18H, O—$CH_3$/O—$CH_2$), 3.07 (s, 4H, $CH_2$—$CH_2$), 1.35-1.09 (m, 18H, $CH_3$)

$^{13}$C NMR (CDCl$_3$, 75 MHz): 167.4, 165.4, 161.5, 159.6, 158.3, 148.5, 113.1, 111.9, 101.4, 91.8, 64.1, 63.8, 58.9, 56.5, 53.0, 48.9, 45.6, 14.8, 14.4

HR-ESI-MS: m/z calcd for C$_{46}$H$_{63}$N$_4$O$_{12}$: 863.4405. found: 863.4424 M+H$^+$ 99b)

Yield: 0.092 g, 0.11 mmol, 84% R$_f$: 0.35

$^1$H NMR (CD$_3$OD, 400 MHz): 7.54 (s, 2H, py-H), 6.82 (s, 2H, py-H), 6.06 (s, 4H, bn-H), 3.97-3.84 (q, 12H, O—CH$_2$), 3.89 (s, 6H, O—CH$_3$), 3.41 (s, 4H, N—CH$_2$), 2.20 (s, 4H, N—CH$_2$), 1.90 (s, 4H, CH$_2$—CH$_2$), 1.33-1.18 (m, 18H, CH$_3$)

$^{13}$C NMR (CD$_3$OD, 75 MHz): 171.0, 168.2, 161.3, 159.9, 159.8, 155.3, 109.7, 107.0, 104.8, 91.3, 63.5, 63.2, 61.7, 42.8, 29.5

HR-ESI-MS: m/z calcd for C$_{44}$H$_{57}$N$_4$O$_{12}$: 833.3973. found: 833.3979 M-H$^-$ Ga(99b)NO$_3$ $^1$H NMR (CD$_3$OD, 400 MHz): 7.87 (s, 2H, py-H), 7.68 (s, 2H, py-H), 6.22 (s, 4H, bn-H), 5.12-4.80 (dd, 4H, N—CH$_2$), 4.29-3.42 (dd, 4H, N—CH$_2$), 4.15 (s, 6H, O—CH$_3$), 4.09-3.43 (dd, 4H, N—CH$_2$), 4.03 (q, 12H, O—CH$_2$), 3.10-2.80 (dd, 4H, CH$_2$—CH$_2$), 1.37-1.25 (m, 18H, CH$_3$)

$^{13}$C NMR (CD$_3$OD, 75 MHz): 175.5, 165.2, 163.6, 154.1, 147.6, 113.6, 111.7, 93.2, 65.6, 63.2, 58.7, 57.5, 49.4, 45.4, 15.2, 15.0

HR-ESI-MS: m/z calcd for C$_{44}$H$_{56}$N$_4$O$_{12}$$^{69}$Ga: 901.3151. found: 901.3138 $^{69}$M$^+$ R$_T$ of radiolabeled product on HPLC: 15.4 minutes Stability versus transferrin (10 min/1 h/2 h; in %): 94/93/93 log P: 1.16

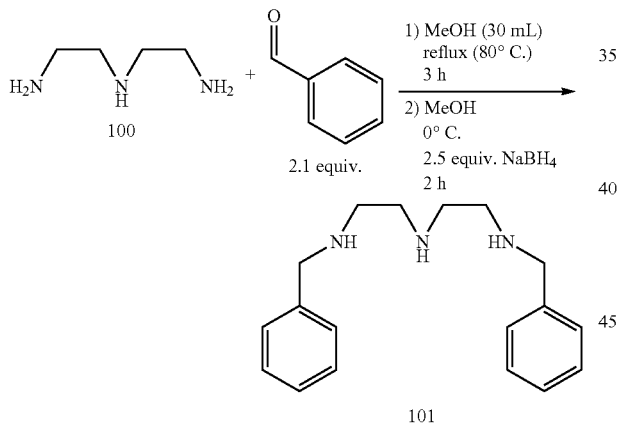

N,N'-(benzyl)diethylenetriamine (101)

Diethylenetriamine 100 (420 µL, 3.877 mmol) and benzaldehyde (830 µL, 8.142 mmol) were dissolved in methanol (30 mL) and refluxed overnight. The solvent was evaporated and then diethyl ether was added to try to precipitate the crude diimine product, but was unsuccessful. The crude diimine product (0.247 g, ~0.621 mmol) was dissolved in methanol (20 mL), cooled to 0° C. in an ice bath, and NaBH$_4$ (43 mg, 1.118 mmol) was slowly added. After 2.5 hours saturated NaHCO$_3$ (20 mL) was added. The crude product was extracted with DCM (5×25 mL). The organic extracts were combined and dried over anhydrous MgSO$_4$, filtered, and evaporated to yield crude 101 as a brown oil (0.1097 g crude, R$_f$ 0.01, 95:5 CH$_2$Cl$_2$:MeOH). 101 was used without further purification.

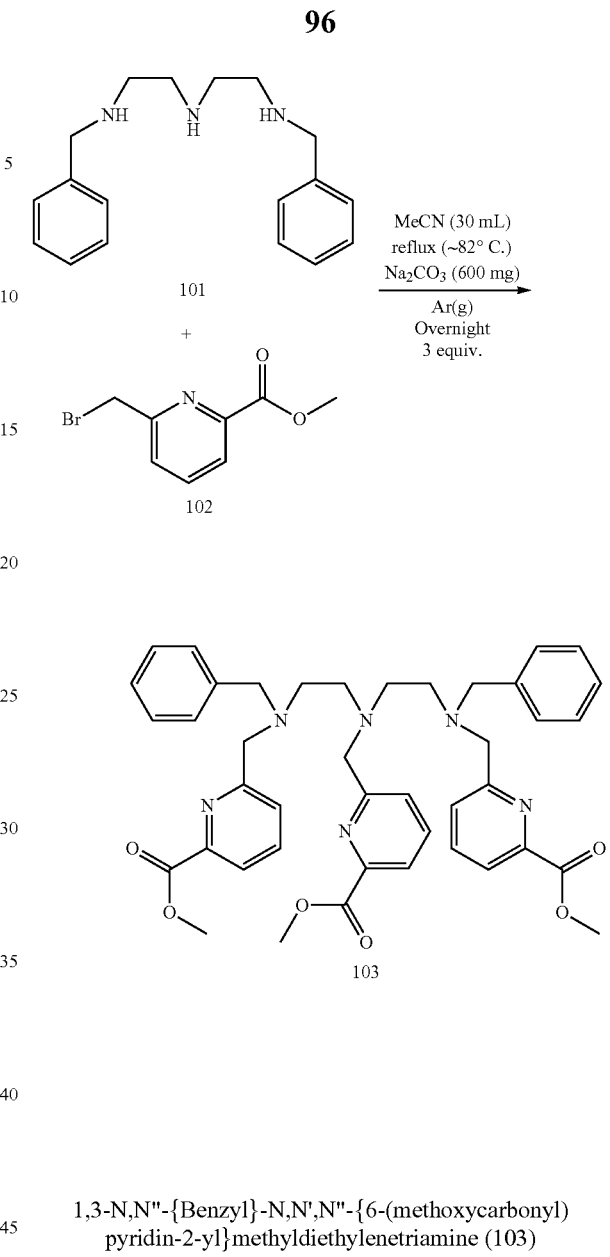

1,3-N,N'''-{Benzyl}-N,N',N''-{6-(methoxycarbonyl)pyridin-2-yl}methyldiethylenetriamine (103)

N,N''-(benzyl)diethylenetriamine (0.140 g crude, 0.434 mmol, 101) was dissolved in acetonitrile (30 mL) with Na$_2$CO$_3$ (600 mg). 6-bromomethylpyridine-2-methoxycarbonyl 102 (0.302 g, 1.304 mmol), was added, and the mixture was refluxed overnight under argon gas. Excess Na$_2$CO$_3$ was filtered and discarded, and deionized water (30 mL) was added. The crude product was subsequently extracted with chloroform (5×30 mL). The organic extracts were combined and dried over anhydrous MgSO$_4$, filtered, and then evaporated to dryness.

The crude product (0.2932 g) was purified by column chromatography twice; the first time starting the elution with CH$_2$Cl$_2$:triethylamine (95:5), and then switching to CH$_2$Cl$_2$:MeOH:triethylamine (92.5:5:2.5), and a second time with hexanes:ethyl acetate (80:20). The product still contained impurities and was used without further purification. R$_f$: 0.60, 90:10 CH$_2$Cl$_2$:MeOH+1% triethylamine). HR-ESI-MS calcd. for C$_{42}$H$_{47}$N$_6$O$_6$: 731.3557; found M+H$^+$ 731.3547.

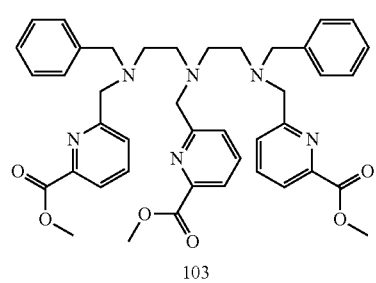

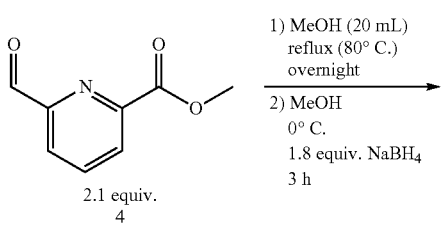

103

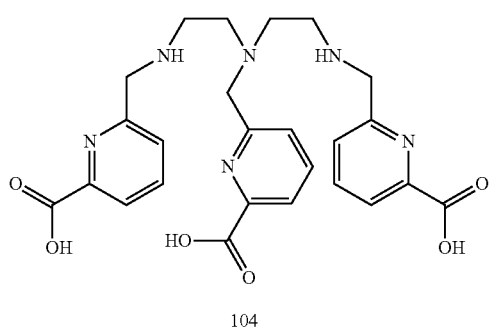

104

N,N',N''-{6-carboxy)pyridin-2-yl}methyldiethylenetriamine (104)

Crude 103 (60 mg, 0.082 mmol) was dissolved in acetic acid (50 mL), and 10 mol % Pd/C was added. The reaction flask was sealed with a rubber septum and a balloon filled with H$_2$ (g) was inserted using a needle. The reaction flask was flushed with H$_2$ (g) for 3 minutes, and allowed to stir for 30 hours at room temperature (monitored by LRMS). The reaction was filtered and the Pd/C was quenched with water. The reaction mixture was evaporated to dryness. The solid was dissolved in HCl (12 M, 30 mL) and refluxed overnight. The crude product was evaporated to dryness and purified by preparative HPLC to yield 5 as a yellow/brown oil, still containing impurities (gradient: A: 0.1% TFA buffer, pH ~2, B: CH$_3$CN. 0-100% B linear gradient 25 min). (17.3 mg, 0.034 mmol, 41%). $^1$H NMR (400 MHz, D$_2$O) δ: 8.02 (m, 1H, pyr-H), 7.88 (m, 3H, pyr-H), 7.82 (m, 2H, pyr-H), 7.71 (m, 1H, Pyr-H), 7.46 (m, 2H, Pyr-H), 4.36 (s, 4H, Pyr-CH$_2$—NH outer picolinic acid), 4.10 (s, 2H, Pyr-CH$_2$—NH inner picolinic acid), 3.44 (t, 4H, —CH$_2$— outer ethylene carbons, $^3$J=5.2 Hz), 3.20 (t, 4H, —CH$_2$— inner ethylene carbons, $^3$J=5.2 Hz). $^{13}$C NMR (100 MHz, D$_2$O) assignment crude due to impurities δ: 168.00, 166.61, 163.27, 162.92, 157.85, 151.07, 146.89, 141.01, 139.61, 127.40, 126.69, 125.12, 57.09, 52.03, 50.59, 45.60. HR-ESI-MS calcd. for C$_{25}$H$_{29}$N$_6$O$_6$: 509.2149; found M+H$^+$ 1509.2144.

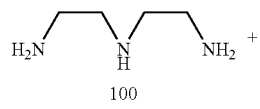

100

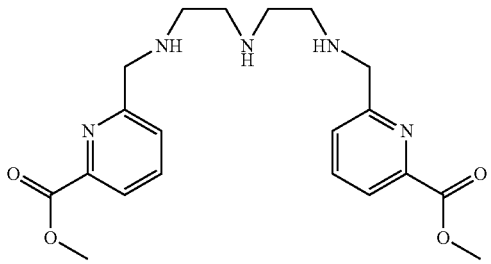

105

N,N''-{6-Methoxycarbonyl)pyridin-2-yl}methyldiethylenetriamine (105)

Diethylenetriamine (66 μL, 0.606 mmol) and methyl-6-formylpyridine-2-carboxylate (0.200 g, 1.21 mmol, 4) were dissolved in methanol (20 mL) and refluxed overnight. The solvent was evaporated and then diethyl ether was added to try to precipitate the crude diimine product, but was unsuccessful. The crude diimine product (0.247 g, ~0.621 mmol) was dissolved in methanol (20 mL), cooled to 0° C. in an ice bath, and NaBH$_4$ (43 mg, 1.118 mmol) was slowly added. After 2.5 hours saturated NaHCO$_3$ (20 mL) was added. Then the crude product was extracted with DCM (5×25 mL). The organic extracts were combined and dried over anhydrous MgSO$_4$, filtered, and evaporated to yield crude 105 as a brown oil (0.125 g crude, R$_f$: 0.01, 95:5 CH$_2$Cl$_2$:MeOH). 105 was used without further purification.

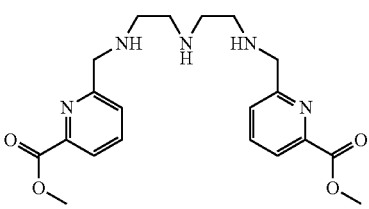

105
+
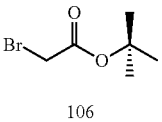

106

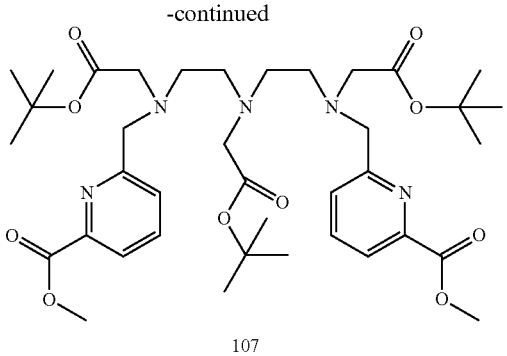

N,N',N''-{(tert-Butoxycarbonyl)methyl}-N,N''-{6-(methoxycarbonyl)pyridin-2-ylmethyl}diethylenetriamine (107)

Crude 105 (0.125 g, ~0.311 mmol) was dissolved in acetonitrile (25 mL) with $Na_2CO_3$ (500 mg). tert-Butylbromoacetate (141 μL, 0.965 mmol) was added, and the mixture was refluxed overnight under argon gas. The excess of $Na_2CO_3$ was filtered and discarded. Deionized water (30 mL) was added. The crude product was subsequently extracted with chloroform (5×30 mL). The organic extracts were combined and dried over anhydrous $MgSO_4$, filtered, and then evaporated to dryness. The crude product (0.2159 g) was purified by column chromatograph twice ($CH_2Cl_2$:MeOH 95:5) to yield crude 107 as a yellow/brown oil (17.8 mg, 0.0239 mmol, $R_f$: 0.53, $CH_2Cl_2$:MeOH 95:5). A large amount of product was lost due to difficulties in column chromatography. The crude product was used without further purification. LR-ESI-MS calcd. for $C_{38}H_{58}N_5O_{10}$: 744.42; found M+H$^+$ 744.8.

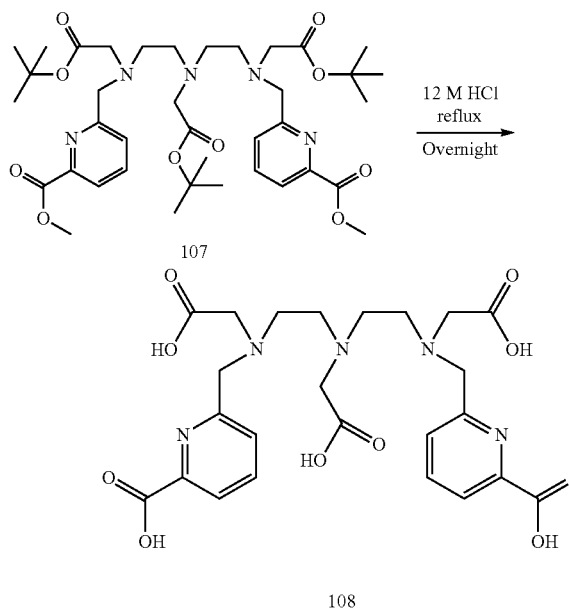

N,N',N''-{(carboxy)methyl}-N,N''-{6-(carboxy)pyridin-2-ylmethyl}diethylenetriamine (108)

Crude 107 (17 mg, 0.0228 mmol) was dissolved in concentrated HCl (20 mL, 12 M) and refluxed overnight. The reaction mixture was evaporated to ~1 mL in an attempt to precipitate the HCl saltproduct; however, this was unsuccessful. The crude deprotected product was evaporated to dryness and then purified by preparative HPLC to yield 6 as an impure yellow/brown oil (gradient: A: 0.1% TFA buffer, pH ~2, B: $CH_3CN$. 0-100% B linear gradient 25 min). (2.4 mg, 0.00438 mmol, 19%). $^1$H NMR (600 MHz, $D_2O$) δ: 8.10 (t, 2H, pyr-H, $^3J$=7.6 Hz), 8.02 (d, 2H, pyr-H, $^3J$=7.6 Hz), 7.70 (d, 2H, pyr-H, $^3J$=7.7 Hz), 4.43 (s, 4H, Pyr-$CH_2$—NH), 3.66 (s, 4H, —CO—$CH_2$—N outer acetic acid), 3.57 (s, 2H, —CO—$CH_2$—N inner acetic acid), 3.33 (m, 4H, —$CH_2$— inner ethylene carbons), 3.25 (m, 4H, —$CH_2$— outer ethylene carbons). $^{13}$C NMR (150 MHz, $D_2O$) δ: 171.73, 171.16, 165.70, 150.51, 146.24, 141.93, 127.55, 124.97, 56.84, 55.23, 54.24, 50.79, 59.79. HR-ESI-MS calcd. for $C_{24}H_{30}N_5O_{10}$: 548.1993; found M+H$^+$ 548.1986.

All publications, patents and patent applications referred to herein are incorporated by reference in their entirety to the same extent as if each individual publication, patent or patent application was specifically and individually indicated to be incorporated by reference in its entirety.

REFERENCES

[1] M. Woods, Z. Kovacs, A. D. Sherry, 2002, "Targeted Complexes of Lanthanide(III) Ions as Therapeutic and Diagnostic Pharmaceuticals" *J. Supramol. Chem.*, 2, 1-15.

[2] W. A. Volkert, T. J. Hoffman, 1999, "Therapeutic Radiopharmaceuticals" *Chem. Rev.* 99, 2269.

[3] P. Caravan, J. J. Ellison, T. J. McMurry, and R. B. Lauffer, 1999, "Gadolinium(III) Chelates as MRI Contrast Agents: Structure, Dynamics, and Applications" *Chem. Rev.* 99, 2293.

[4] G. M. Lanza, R. Lamerichs, S. Caruthers, S. A. Wickline, 2003, "Molecular Imaging in MR with Targeted Paramagnetic nanoparticles", MEDICAMUNDI 47, 34.

[5] S. Liu, D. S. Edwards, 2001, "Bifunctional Chelators for Therapeutic Lanthanide Radiopharmaceuticals" *Bioconjugate Chemistry*, 12, 7.

[6] Y. Bretonniere, M. Mazzanti, J. Pecaut, F. A. Dunand, and A. E. Merbach, 2001, "Solid-state and solution properties of the lanthanide complexes of a new heptadentate tripodal ligand: A route to gadolinium complexes with an improved relaxation efficiency" *Inorg. Chem.*, 40, 6737.

[7] Y. Bretonniere, M. Mazzanti, J. Pecaut, F. A. Dunand, and A. E. Merbach, 2001a, "A new heptadentate tripodal ligand leading to a gadolinium complex with an improved relaxation efficiency" *Chem. Commun.*, 621.

[8] A. Borel, S. Laus, A. Ozarowski, C. Gateau, A. Nonat, M. Mazzanti, L. Helm, 2007, "Multiple-frequency EPR spectra of two aqueous Gd$^{3-}$ polyamino polypyridine carboxylate complexes: A study of high field effects" *J. Phys. Chem. A*, 111, 5399.

[9] Q. Huang, B. Zhai, 2007, "Crystal structure, thermal and magnetic studies of a dinuclear Mn(II) complex with decadentate picolinate based ligand" *J. Coord. Chem.*, 60, No. 20, 2257.

[10] E. Balogh, M. Mato-Iglesias, C. Platas-Iglesias, E. Toth, K. Djanashvili, J. A. Peters, A. de Blas, T. Rodriguez-Blas, 2006, Pyridine- and phosphonate-containing ligands for stable Ln complexation. Extremely fast water exchange on the Gd$^{III}$ chelates" *Inorg. Chem.*, 45, 8719.

[11] M. Mato-Iglesias, E. Balogh, C. Platas-Iglesias, E. Toth, A. de Blas, T. R. Blas, 2006, "Pyridine and phosphonate containing ligands for stable lanthanide complexation. An experimental and theoretical study to assess the solution structure" *Dalton Trans.*, 5404.

[12] N. Chatterton, Y. Bretonniere, J. Pecaut, and M. Mazzanti, 2005, "An efficient design for the rigid assembly of four bidentate chromophores in water-soluble highly luminescent lanthanide complexes" *Angew. Chem. Int. Ed.*, 44, 7595.

[13] N. Chatterton, C. Gateau, M. Mazzanti, J. Pecaut, A. Borel, L. Helm, A. Merbach, 2005a, "The effect of pyridinecarboxylate chelating groups on the stability and electronic relaxation of gadolinium complexes" *Dalton Trans.*, 1129.

[14] M. Mato-Iglesias, C. Platas-Iglesias, K. Djanashvili, J. A. Peters, E. Toth, E. Balogh, R. N. Muller, L. Vander Elst, A. de Blas, T. Rodriguez-Blas, 2005, "The highest water exchange rate ever measured for a Gd(III) chelate" *Chem. Commun.*, 4729.

[15] E. Balogh, M. Mato-Iglesias, C. Platas-Iglesias, E. Toth, K. Djanashvili, J. A. Peters, A. de Blas, T. Rodriguez-Blas, 2006, Pyridine- and phosphonate-containing ligands for stable Ln complexation. Extremely fast water exchange on the $Gd^{III}$ chelates" *Inorg. Chem.*, 45, 8719.

[16] M. Mato-Iglesias, E. Balogh, C. Platas-Iglesias, E. Toth, A. de Blas, T. R. Blas, 2006, "Pyridine and phosphonate containing ligands for stable lanthanide complexation. An experimental and theoretical study to assess the solution structure" *Dalton Trans.*, 5404.

[17] A. Borel, S. Laus, A. Ozarowski, C. Gateau, A. Nonat, M. Mazzanti, L. Helm, 2007, "Multiple-frequency EPR spectra of two aqueous $Gd^{3+}$ polyamino polypyridine carboxylate complexes: A study of high field effects" *J. Phys. Chem. A*, 111, 5399.

[18] A. Borel, H. Kang, C. Gateau, M. Mazzanti, R. B. Clarkson, R. L. Belford, 2006, "Variable temperature and EPR frequency study of two aqueous Gd(III) complexes with unprecedented sharp lines" *J. Phys. Chem. A*, 110, 12434.

[19] P. H. Fries, C. Gateau, M. Mazzanti, 2005, "Practical route to relative diffusion coefficients and electronic relaxation rates of paramagnetic metal complexes in solution by model-independent outer-sphere NMRD. Potentiality for MRI contrast agents" *J. Am. Chem. Soc.*, 126, 15801.

[20] C. Gateau, M. Mazzanti, J. Pecaut, F. A., Dunand, L. Helm, 2003, "Solid-state and solution properties of the lanthanide complexes of a new nonadentate tripodal ligand derived from 1,4,6-triazacyclononane" *Dalton Trans.*, 2428.

[21] A. Nonat, C. Gateau, P. H. Fries, M. Mazzanti, 2006, "Lanthanide complexes of a picolinate ligand derived from 1,4,7-triazacyclononane with potential application in magnetic resonance imaging and time-resolved luminescence imaging" *Chem. Eur. J.*, 12, 7133.

[22] M. Mazzanti, U.S. Pat. Appl. Publ. 2008/0227962, "Method for obtaining highly luminescent lanthanide complexes".

[23] C. Gateau, M. Mazzanti, A. Nonat, PCT Int. Appl. WO 2007/083036, "Novel lanthanide ligands and complexes, and use thereof as contrast agents"

[24] R. Ferreiros-Martinez, D. Esteban-Gomez, C. Platas-Iglesias, A. de Blas, T. Rodriguez-Blas, 2008, "Zn(II), Cd(II) and Pb(II) complexation with pyridinecarboxylate containing ligands" *Dalton Trans.*, 5754.

[25] Krohn, K. A.; Link, J. M.; Mason, R. P., *J. Nucl. Med.* 2008 49 Suppl 2:129S-48S.

[26] Ferreiros-Martinez, R.; Esteban-Gomez, D.; Platas-Iglesias, C.; de Blas, A.; Rodriguez-Blas, T., *Dalton Trans.* 2008, 5754-5758.

[27] Velikyan, I.; Maecke, H.; Langstrom, B., *Bioconjugate Chem.* 2008, 19, 569-573.

[28] Meyer, G. J.; Maecke, H. R.; Schuhmacher, J.; Knapp, W. H.; Hofmann, M., *Eur. J. Nucl. Med. Mol. Imaging* 2004, 31, 1097-1104.

[29] Velikyan, I.; Beyer, G. J.; Langstrom, B., *Bioconjugate Chem.* 2004, 15, 554-560.

[30] Harris, W. R.; Pecoraro, V. L., *Biochemistry* 1983, 22, 292-299.

[31] Ferreira, C. L.; Lamsa, E.; Woods, M.; Duan, Y.; Fernando, P.; Bensimon, C.; Kordos, M.; Guenther, K.; Jurek, P.; Kiefer, G. E., *Bioconjugate Chem.* 2010, 21, (3), 531-536.

[32] Bottari, E.; Anderegg, G., *Helv. Chim. Acta* 1967, 50, 2349-2356.

[33] Clarke, E. T.; Martell, A. E., *Inorg. Chim. Acta* 1991, 190, 37-46.

[34] Clarke, E. T.; Martell, A. E., *Inorg. Chim. Acta* 1991, 181, 273-280.

[35] Andre, J. P.; Maecke, H. R.; Zehnder, M.; Macko, L.; Akyel, K. G. *Chem. Commun.* 1998, 12, 1301-1302

[36] Heppeler, A.; Froidevaux, S.; Maecke, H. R.; Jermann, E.; Béhé, M.; Powell, P.; Hennig, M., *Chem. Eur. J.* 1999, 5, 1016-1023.

[37] McMurry, T. J.; Brechbiel, M.; Kumar, K.; Gansow, O. A., *Bioconjugate Chem.* 1992, 3, 108-117.

[38] Wei, L.; Ye, Y.; Wadas, T. J.; Lewis, J. S.; Welch, M. J.; Achilefu, S.; Anderson, C. J., *Nucl. Med. Biol.* 2009, 36, 277-285.

[39] Platas-Iglesias, C.; Marto-Iglesias, M.; Djanashvili, K.; Muller, R. N.; Vander Elst, L.; Peters, J. A.; de Blas, A.; Rodrigues-Blas, T., *Chem. Eur. J.* 2004, 3579, 3590.

[40] Ali, M. S.; Quadri, S. Y., *Bioconjugate Chem.* 1996, 7, 576-583.

[41] Sephton, R. G.; Hodgson, G. S.; De Abrew, S.; Harris, A. W., *J. Nuc. Med* 1978, 19, (8), 930-935.

[42] Malyshev, K. V.; Smirnov, V. V. *Radiokhimiya* 1975, 17, 137-140

[43] C. Platas-Iglesias, M. Marto-Iglesias, K. Djanashvili, R. N. Muller, L. Vander Elst, J. A. Peters, A. de Blas and T. Rodrigues-Blas, *Chem. Eur. J.*, 2004, 3579, 3590.

[44] X. Zeng, D. Coquiere, A. Alenda, E. Gather, T. Prange, Y. Li, O. Reinaud and I. Jabin, *Chem. Eur. J.*, 2006, 12, 6393.

[45] Andrianina-Ralambomanana, D.; Dorothee, R.-R.; Clement, R. A.; Maugein, J.; Pelinski, L., *Bioorg. Med. Chem.* 2008, 16, (21), 9546-9553.; Menage, S.; Galey, J.-B.; Dumats, J.; Hussler, G.; Seite, M.; Luneau, I. G.; Chottard, G.; Fontecave, M., *J. Am. Chem. Soc.* 1998, 120, (13370-13382).

[46] D. S. Wilbur, D. K. Hamlin, R. L. Vesella, J. E. Stray, K. R. Buhler, P. S. Stayton, L. A. Klumb, P. M. Pathare and S. A. Weerawarna, *Bioconjugate Chem.*, 1996, 7, 689.; M. S. Ali and S. Y. Quadri, *Bioconjugate Chem.*, 1996, 7, 576.

[47] Gran, G., *Analyst* 1952, 77, 661-671.

[48] Baes, C. F.; Mesmer, R. E., Wiley-Interscience: New York, 1976.

[49] Altomare, A.; Burla, M. C.; Camalli, M.; Cascarano, G. L.; Giacovazzo, C.; Guagliardi, A.; Moliterni, A. G. G.; Polidori, G.; Spagna, R., *J. Appl. Crystallogr.* 1999, 32, (1), 115-119.

[50] Sheldrick, G. M. *SHELXL97-2: Program for the Refinement of Crystal Structures*, University Göttingen, 1998.

[51] Sluis, P. v. d.; Spek, A. L., *Acta Crystallogr., Sect A* 1990, A46, 194-201.

[52] Relegatti, *Chem. Commun.* 2008.

[53] Platas-Iglesias, C.; Marto-Iglesias, M.; Djanashvili, K.; Muller, R. N.; Vander Elst, L.; Peters, J. A.; de Blas, A.; Rodrigues-Blas, T., *Chem. Eur. J.* 2004, 3579-3590.

[54] Kwon, T. H., *J. Am. Chem. Soc.* 2008, 130, 3726.

What is claimed is:

1. A bifunctional chelating agent of the formula (I):

$$R^1-N(Q^1)-M-N(Q^2)-R^{1'} \quad (I)$$

wherein:

-M- is

[structures shown]

$Q^1$, $Q^2$ and $Q^4$ are independently H or R;

$Q^5$ is H, R or $R^{1''}$;

$Q^6$ is H or $R^{1''}$;

$Q^7$ is H or R;

$A^1$ and $A^2$ form together with the atoms to which they are attached a $C_6$-$C_{10}$-aryl, $C_6$—$C_{1-10}$-heteroaryl, $C_3$-$C_5$-cycloalkyl, $C_7$-$C_{10}$-cycloalkyl or $C_3$-$C_{10}$-heterocyclyl group;

R is —C(O)-L,

[structure: —(CH$_2$)$_r$—C(Q$^3$)(H)—(CH$_2$)$_n$—(X,Y)$_m$—L]

—(CHR$^2$)$_p$COR$^3$ or —(CHR$^2$)$_p$PO$_2$R$^4$R$^5$;

$Q^3$ is H, —(CHR$^2$)$_w$COR$^3$ or —(CHR$^2$)$_w$PO$_2$R$^4$R$^5$;

$R^1$, $R^{1''}$ and $R^{1'''}$ are independently

[structures: substituted pyridine with Z$^1$, Z$^2$, R$^6$ and —C(O)OH; 8-hydroxyquinoline; quinoline-2-carboxylic acid]

each $R^2$ is independently hydrogen; $C_1$-$C_4$ alkyl or ($C_1$-$C_2$alkyl)phenyl; each $R^3$, $R^4$ and $R^5$ are independently OH, an —O-protecting group or a leaving group;

$R^6$ is H; OH; an alkyl-LG or alkoxy-LG, wherein LG is a leaving group; a boronate ester or a leaving group;

X and Y are each independently hydrogen or may be taken with an adjacent X and Y to form an additional carbon—carbon bond;

$Z^1$ and $Z^2$ are independently CH or N;

m is an integer from 0 to 10 inclusive;

n is 0 or 1;

p is 1 or 2;

r is 0 or 1;

w is 0 or 1;

z is 1 or 2;

L is a linker/spacer group covalently bonded to, and replacing one hydrogen atom of the carbon atom to which it is joined, said linker/spacer group being represented by the formula (II):

$$R^8-(R^7)(R^9)Cyc-(CH_2)_t- \quad (II)$$

wherein:

s is an integer of 0 or 1;

t is an integer of 0 to 20 inclusive;

$R^7$, $R^8$ and $R^9$ are independently H; an electrophilic, nucleophilic or electron-rich moiety that allows for covalent attachment to a carrier comprising a biotargeting group, a lipophilic moiety or a biosensor; a protected form or a precursor of the electrophilic, nucleophilic or electron-rich moiety; or a synthetic linker having an electrophilic, nucleophilic or electron-rich moiety that allows for covalent attachment to the carrier comprising a biotargeting group, a lipophilic moiety or a biosensor, or a protected form or a precursor of the electrophilic, nucleophilic or electron-rich moiety of the synthetic linker, and Cyc represents a cyclic aliphatic moiety, aromatic moiety, aliphatic heterocyclic moiety, or aromatic heterocyclic moiety, each of said moieties optionally substituted with one or more groups, which do not interfere with binding to a carrier comprising a biotargeting group, a lipophilic moiety or a biosensor;

or a pharmaceutically acceptable salt thereof, provided that the chelating agent is not 6,6',6'',6'''-((ethane-1,2-diylbis(azanetriyl))tetrakis(methylene))tetrapicolinic acid, 6,6'-((ethane-1,2-diylbis((phosphonomethyl)azanediyl))bis(methylene))dipicolinic acid, 6,6'-((ethane-1,2-diylbis((carboxymethyl)azanediyl))bis(methylene))dipicolinic acid or 6,6'-((ethane-1,2-diylbis((pyridin-2-ylmethyl)azanediyl))bis(methylene))dipicolinic acid, and provided that the bifunctional chelating agent comprises at least one covalently attached moiety that allows for covalent attachment to the carrier comprising a biotargeting group, a lipophilic moiety or a biosensor.

2. The bifunctional chelating agent according to claim 1, wherein the bifunctional chelating agent is of formula (Ia):

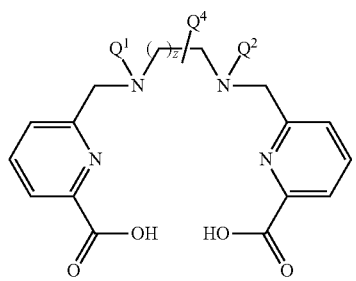

(Ia)

wherein $Q^1$, $Q^2$, $Q^4$ and z are as defined in claim 1.

3. The bifunctional chelating agent according to claim 1, wherein $Q^1$ and $Q^2$

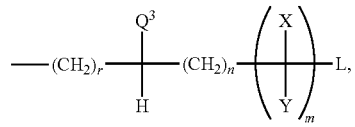

are each H and $Q^4$ is wherein L, X, Y, $Q^3$, m, n and r are as defined in claim 1.

4. The bifunctional chelating agent according to claim 3, wherein $Q^1$ and $Q^2$ are each H and $Q^4$ is

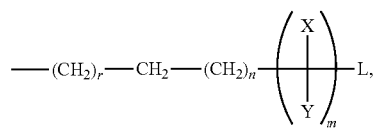

wherein L, X, Y, m, n and r are as defined in claim 1.

5. The bifunctional chelating agent according to claim 4, wherein $Q^1$ and $Q^2$ are each H and $Q^4$ is

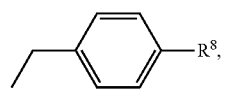

wherein $R^8$ is as defined in claim 1.

6. The bifunctional chelating agent according to claim 1, wherein at least one of $Q^1$ and $Q^2$ is

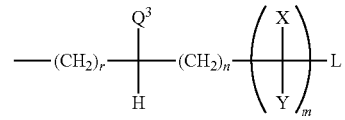

and $Q^4$ is H, wherein L, X, Y, $Q^3$, m, n and r are as defined in claim 1.

7. The bifunctional chelating agent according to claim 6, wherein at least one of $Q^1$ and $Q^2$ is

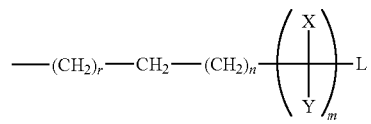

and $Q^4$ is H, wherein L, X, Y, m, n and r are as defined in claim 1.

8. The bifunctional chelating agent according to claim 7, wherein at least one of $Q^1$ and $Q^2$ is

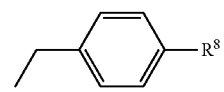

and $Q^4$ is H, wherein $R^8$ is as defined in claim 1.

9. The bifunctional chelating agent according to claim 1, wherein at least one of $Q^1$ and $Q^2$ is —$(CHR^2)_pCOR^3$ and $Q^4$ is H, wherein $R^3$ and p are as defined in claim 1.

10. The bifunctional chelating agent according to claim 1, wherein at least one of $Q^1$ and $Q^2$ is —$(CHR^2)_pCOR^3$ and $Q^4$ is H, wherein $R^3$ is a leaving group and p is as defined in claim 1.

11. The bifunctional chelating agent according to claim 1, wherein at least one of $Q^1$ and $Q^2$ is —$CH_2COR^3$ and $Q^4$ is H, wherein $R^3$ is as defined in claim 1.

12. The bifunctional chelating agent according to claim 1, wherein at least one of $Q^1$ and $Q^2$ is —$CH_2COR^3$ and $Q^4$ is H, wherein $R^3$ is a leaving group.

13. The bifunctional chelating agent according to claim 1, wherein at least one of $Q^1$ and $Q^2$ is —$CH_2C\equiv CH$ and $Q^4$ is H.

14. The bifunctional chelating agent according to claim 1, wherein $Q^1$ and $Q^2$ are —$(CHR^2)_pCOR^3$ and $Q^4$ is R, wherein $R^2$, $R^3$, and R are as defined in claim 1.

15. The bifunctional chelating agent according to claim 1, wherein $R^6$ is $NO_2$, $NH_2$, isothiocyanato, semicarbazido, thiosemicarbazido, maleimido, bromoacetamido or carboxyl.

16. A complex comprising the bifunctional chelating agent defined in claim 1 or a pharmaceutically acceptable salt thereof, and an ion of a stable or radioactive form of a metal selected from a group consisting of Ga, In, Tl, La, Ce, Pr, Nd, Pm, Sm, Eu, Gd, Tb, Dy, Ho, Er, Tm, Yb, Lu, Sc, Y, Ti, Zr, Cr, Mn, Tc, Re, Fe, Ru, Co, Rh, Ir, Ni, Pd, Pt, Cu, Zn, Cd, Hg, Al, Ge, Sn, Pb, Sb, Bi, Te, Po, Mg, Ca, Sr, Ba, Ra, Ac, Th and U.

17. The complex according to claim 16, wherein the ion is an ion of a radioactive metal selected from a group consisting of $^{66}$Ga, $^{67}$Ga, $^{68}$, $^{111}$In, $^{201}$Tl, $^{142}$Pr, $^{149}$Pm, $^{153}$Sm, $^{153}$Gd, $^{159}$Gd, $^{166}$Ho, $^{175}$Yb, $^{177}$Lu, $^{47}$Sc, $^{90}$Y, $^{89}$Zr, $^{51}$Cr, $^{99m}$Tc, $^{188}$Re, $^{186}$Re, $^{57}$Co, $^{101m}$Rh, $^{62}$Cu, $^{64}$Cu, $^{67}$Cu, $^{117m}$Sn, $^{203}$Pb, $^{212}$Pb, $^{212}$Bi, $^{213}$Bi, $^{223}$Ra, and $^{225}$Ac.

* * * * *